US012569452B2

(12) United States Patent  
Günther et al.

(10) Patent No.: US 12,569,452 B2  
(45) Date of Patent: **\*Mar. 10, 2026**

(54) OPHTHALMIC COMPOSITIONS COMPRISING F6H8

(71) Applicant: NOVALIQ GMBH, Heidelberg (DE)

(72) Inventors: Bernhard Günther, Dossenheim (DE); Frank Löscher, Schriesheim (DE); Hartmut Voss, Schriesheim (DE); Sonja Krösser, Heidelberg (DE); Kirsten Eickhoff, Heidelberg (DE); Daniela Willen, Oberzent (DE); Markus Beier, Weinheim (DE); Thomas Schlüter, Heidelberg (DE)

(73) Assignee: NOVALIQ GMBH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/439,258

(22) Filed: Feb. 12, 2024

(65) Prior Publication Data

US 2024/0245625 A1     Jul. 25, 2024

Related U.S. Application Data

(63) Continuation of application No. 16/753,701, filed as application No. PCT/EP2018/076908 on Oct. 3, 2018, now Pat. No. 11,896,559.

(60) Provisional application No. 62/568,138, filed on Oct. 4, 2017.

(51) Int. Cl.  
*A61K 31/02*         (2006.01)  
*A61K 9/00*          (2006.01)  
*A61P 27/04*         (2006.01)

(52) U.S. Cl.  
CPC ............ *A61K 31/02* (2013.01); *A61K 9/0048* (2013.01); *A61P 27/04* (2018.01)

(58) Field of Classification Search  
CPC ........ A61K 31/02; A61K 9/0048; A61P 27/02  
See application file for complete search history.

(56) References Cited

U.S. PATENT DOCUMENTS

| | | |
|---|---|---|
| 2,616,927 A | 11/1952 | Kauck et al. |
| 4,452,818 A | 6/1984 | Haidt |
| 4,649,047 A | 3/1987 | Kaswan |
| 5,077,036 A | 12/1991 | Long |
| 5,126,127 A | 6/1992 | Bhagwat et al. |
| 5,152,997 A | 10/1992 | Ebert et al. |
| 5,254,338 A | 10/1993 | Sakai et al. |
| 5,326,566 A | 7/1994 | Parab |
| 5,336,175 A | 8/1994 | Mames |
| 5,340,567 A | 8/1994 | Cole et al. |
| 5,370,313 A | 12/1994 | Beard |
| 5,518,731 A | 5/1996 | Meadows |
| 5,578,020 A | 11/1996 | Mosley |
| 5,667,809 A | 9/1997 | Trevino et al. |

| | | |
|---|---|---|
| 5,849,291 A | 12/1998 | Kessler |
| 5,851,544 A | 12/1998 | Penska et al. |
| 5,874,469 A | 2/1999 | Maniar et al. |
| 5,874,481 A | 2/1999 | Weers et al. |
| 5,904,933 A | 5/1999 | Riess et al. |
| 5,980,936 A | 11/1999 | Krafft et al. |
| 5,981,607 A | 11/1999 | Ding et al. |
| 6,042,845 A | 3/2000 | Sun et al. |
| 6,060,085 A | 5/2000 | Osborne |
| 6,113,919 A | 9/2000 | Reiss et al. |
| 6,140,374 A | 10/2000 | May et al. |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,105 B1 | 7/2001 | Johnstone |
| 6,262,126 B1 | 7/2001 | Meinert |
| 6,264,990 B1 | 7/2001 | Knepp et al. |
| 6,294,563 B1 | 9/2001 | Garst |
| 6,335,335 B2 | 1/2002 | Higashiyama et al. |
| 6,372,243 B2 | 4/2002 | Kobuch |
| 6,391,879 B1 | 5/2002 | Reeves |
| 6,399,087 B1 | 6/2002 | Zhang et al. |
| 6,458,376 B1 | 10/2002 | Meadows |
| 6,486,212 B2 | 11/2002 | Meinert |
| 6,489,367 B1 | 12/2002 | Meinert |
| 6,528,086 B2 | 3/2003 | Zhang |
| 6,576,663 B2 | 6/2003 | Klimko |
| 6,730,328 B2 | 5/2004 | Maskiewicz et al. |
| 7,001,607 B1 | 2/2006 | Menz et al. |

(Continued)

FOREIGN PATENT DOCUMENTS

| | | |
|---|---|---|
| CA | 3021394 | 12/2021 |
| CN | 200977281 Y | 11/2007 |

(Continued)

OTHER PUBLICATIONS

"EvoTears, Product Description" Accessed Online: Dec. 21, 2023. https://evotears.com/at/das-produkt/ (Year: 2017).  
"Ocular Surface Disease Index (OSDI)", Dec. 1, 2003, pp. 1-2, Retrieved from the Internet: URL: http://www.supereyecare.com/resources/OSDI.pdf.

(Continued)

*Primary Examiner* — Kortney L. Klinkel  
*Assistant Examiner* — Richard Grant Peckham  
(74) *Attorney, Agent, or Firm* — Hoxie & Associates LLC

(57)                    ABSTRACT

The present disclosure provides methods of treatment using ophthalmic compositions comprising semifluorinated alkanes for keratoconjunctivitis sicca and/or Meibomian gland dysfunction, which methods provide for the enrichment of an ophthalmic tissue in the semifluorinated alkane, and optionally methods of delayed release of the semifluorinated alkane from the enriched ophthalmic tissue to the surface of the cornea and/or conjunctiva, and/or to the Meibomian gland.

21 Claims, 3 Drawing Sheets

(56) References Cited

U.S. PATENT DOCUMENTS

| | | | |
|---|---|---|---|
| 7,026,359 | B1 | 4/2006 | Gross et al. |
| 7,041,705 | B2 | 5/2006 | Mishra et al. |
| 7,063,241 | B2 | 6/2006 | Spada et al. |
| 7,074,827 | B2 | 7/2006 | Ueno |
| 7,258,869 | B1 | 8/2007 | Berry et al. |
| 7,283,239 | B2 | 10/2007 | Nonogaki et al. |
| 7,335,379 | B2 | 2/2008 | Carrara et al. |
| 7,608,261 | B2 | 10/2009 | Furfine et al. |
| 7,687,455 | B2 | 3/2010 | Bonnet et al. |
| 7,732,415 | B2 | 6/2010 | Dawson et al. |
| 7,740,875 | B2 | 6/2010 | Dechow |
| 7,776,349 | B2 | 8/2010 | Dechow |
| 8,029,977 | B2 | 10/2011 | Meinert et al. |
| 8,222,292 | B2 | 7/2012 | Goskonda et al. |
| 8,309,120 | B2 | 11/2012 | Koch et al. |
| 8,328,775 | B2 | 12/2012 | Gokhale et al. |
| 8,338,479 | B2 | 12/2012 | Chang et al. |
| 8,343,945 | B2 | 1/2013 | Tamarkin et al. |
| 8,470,873 | B2 | 6/2013 | Chen |
| 8,492,334 | B2 | 7/2013 | Lavik et al. |
| 8,501,800 | B2 | 8/2013 | Bowman et al. |
| 8,614,178 | B2 | 12/2013 | Theisinger et al. |
| 8,669,241 | B2 | 3/2014 | Matsumura et al. |
| 8,758,826 | B2 | 6/2014 | Bevier |
| 8,759,281 | B2 | 6/2014 | Bonnet et al. |
| 8,759,404 | B2 | 6/2014 | Daftary et al. |
| 8,772,337 | B2 | 7/2014 | Pilotaz et al. |
| 8,796,340 | B2 | 8/2014 | Theisinger et al. |
| 8,865,131 | B2 | 10/2014 | Hagedorn et al. |
| 8,916,157 | B2 | 12/2014 | Krause et al. |
| 8,957,110 | B2 | 2/2015 | Aleo et al. |
| 8,986,738 | B2 | 3/2015 | Meinert |
| 9,000,048 | B2 | 4/2015 | Mecozzi et al. |
| 9,005,626 | B2 | 4/2015 | Seigfried |
| 9,012,503 | B2 | 4/2015 | Tabuchi et al. |
| 9,023,898 | B2 | 5/2015 | Wong et al. |
| 9,062,275 | B2 | 6/2015 | Lopez |
| 9,149,484 | B2 | 10/2015 | Warner et al. |
| 9,186,305 | B1 | 11/2015 | Suzuki |
| 9,241,900 | B2 | 1/2016 | Wilson |
| 9,265,809 | B2 | 2/2016 | Johnson |
| 9,278,120 | B2 | 3/2016 | Cruzat et al. |
| 9,308,262 | B2 | 4/2016 | Günther et al. |
| 9,446,026 | B2 | 9/2016 | Bingaman et al. |
| 9,549,906 | B2 | 1/2017 | Lynch et al. |
| 9,630,941 | B2 | 4/2017 | Elsohly et al. |
| 9,757,459 | B2 | 9/2017 | Günther et al. |
| 9,757,460 | B2 | 9/2017 | Günther et al. |
| 9,770,508 | B2 | 9/2017 | Günther et al. |
| 9,814,695 | B2 | 11/2017 | Anastassov et al. |
| 9,844,530 | B1 | 12/2017 | Anastassov et al. |
| 9,878,000 | B2 | 1/2018 | Gu et al. |
| 9,968,678 | B2 | 5/2018 | Theisinger et al. |
| 9,982,032 | B2 | 5/2018 | Park et al. |
| 10,004,714 | B2 | 6/2018 | Zhu et al. |
| 10,045,996 | B2 | 8/2018 | Theisinger et al. |
| 10,045,997 | B2 | 8/2018 | Chen et al. |
| 10,058,615 | B2 | 8/2018 | Günther et al. |
| 10,064,944 | B2 | 9/2018 | Wilson |
| 10,123,904 | B2 | 11/2018 | Chauhan et al. |
| 10,130,707 | B2 | 11/2018 | Günther et al. |
| 10,273,298 | B2 | 4/2019 | Günther et al. |
| 10,286,035 | B2 | 5/2019 | Gavaris |
| 10,369,117 | B2 | 8/2019 | Günther et al. |
| 10,449,164 | B2 | 10/2019 | Günther et al. |
| 10,507,132 | B2 | 12/2019 | Graf et al. |
| 10,525,062 | B2 | 1/2020 | Theisinger et al. |
| 10,543,121 | B2 | 1/2020 | Labombarbe et al. |
| 10,555,953 | B2 | 2/2020 | Theisinger et al. |
| 10,576,154 | B2 | 3/2020 | Günther et al. |
| 10,668,010 | B2 | 6/2020 | Ficko |
| 10,682,315 | B2 | 6/2020 | Scherer et al. |
| 10,813,976 | B2 | 10/2020 | Loscher et al. |
| 10,813,999 | B2 | 10/2020 | Günther et al. |
| 10,925,927 | B2 | 2/2021 | Brockmeyer et al. |
| 11,135,266 | B2 | 10/2021 | Kerwin et al. |
| 11,154,513 | B2 | 10/2021 | Scherer et al. |
| 11,160,865 | B2 | 11/2021 | Theisinger et al. |
| 11,241,497 | B2 | 2/2022 | Reza et al. |
| 11,273,174 | B2 | 3/2022 | Löscher et al. |
| 11,278,503 | B2 | 3/2022 | Günther et al. |
| 11,285,163 | B2 | 3/2022 | Shah et al. |
| 11,324,757 | B2 | 5/2022 | Theisinger et al. |
| 11,357,738 | B2 | 6/2022 | Scherer et al. |
| 11,400,132 | B2 | 8/2022 | Löscher et al. |
| 11,413,323 | B2 | 8/2022 | Leo et al. |
| 11,457,626 | B2 | 10/2022 | Dyer |
| 11,576,893 | B2 | 2/2023 | Löscher et al. |
| 11,583,513 | B2 | 2/2023 | Günther et al. |
| 11,684,589 | B2 | 6/2023 | Günther et al. |
| 11,723,861 | B2 | 8/2023 | Günther et al. |
| 11,730,794 | B2 | 8/2023 | Yancopoulos |
| 11,844,836 | B2 | 12/2023 | Günther et al. |
| 11,896,559 | B2 | 2/2024 | Günther et al. |
| 11,987,623 | B2 | 5/2024 | Günther et al. |
| 12,005,033 | B2 | 6/2024 | Günther et al. |
| RE50,060 | E | 7/2024 | Graf et al. |
| 12,029,757 | B2 | 7/2024 | Löscher et al. |
| 12,059,449 | B2 | 8/2024 | Leo et al. |
| 12,128,010 | B2 | 10/2024 | Scherer et al. |
| 12,150,955 | B2 | 11/2024 | Löscher et al. |
| 12,226,422 | B2 | 2/2025 | Löscher et al. |
| 2002/0004063 | A1 | 1/2002 | Zhang |
| 2002/0006442 | A1 | 1/2002 | Mishra et al. |
| 2002/0128527 | A1 | 9/2002 | Meinert |
| 2002/0137793 | A1 | 9/2002 | Klimko |
| 2003/0018044 | A1 | 1/2003 | Peymar |
| 2003/0027833 | A1 | 2/2003 | Cleary et al. |
| 2003/0170194 | A1 | 9/2003 | Piotrowiak |
| 2004/0044045 | A1 | 3/2004 | Burk |
| 2004/0082660 | A1 | 4/2004 | Ueno |
| 2004/0101551 | A1 | 5/2004 | Selzer |
| 2004/0265362 | A1 | 12/2004 | Susilo |
| 2004/0266702 | A1 | 12/2004 | Dawson et al. |
| 2005/0075407 | A1 | 4/2005 | Tamarkin et al. |
| 2005/0079210 | A1 | 4/2005 | Gupta |
| 2005/0084553 | A1 | 4/2005 | Moon et al. |
| 2005/0175541 | A1 | 8/2005 | Lanza et al. |
| 2005/0274744 | A1 | 12/2005 | Spada et al. |
| 2005/0288196 | A1 | 12/2005 | Horn |
| 2006/0009522 | A1 | 1/2006 | Reza et al. |
| 2006/0078580 | A1 | 4/2006 | Dechow |
| 2006/0153905 | A1 | 7/2006 | Carrara et al. |
| 2007/0238732 | A1 | 10/2007 | Graham et al. |
| 2008/0019926 | A1 | 1/2008 | Krafft et al. |
| 2008/0039807 | A1 | 2/2008 | Pine |
| 2008/0050335 | A1 | 2/2008 | Faour et al. |
| 2008/0089923 | A1 | 4/2008 | Burkstrand et al. |
| 2008/0112895 | A1 | 5/2008 | Kottayil et al. |
| 2008/0153909 | A1 | 6/2008 | Dana et al. |
| 2008/0207537 | A1 | 8/2008 | Turner et al. |
| 2008/0234389 | A1 | 9/2008 | Mecozzi et al. |
| 2008/0254106 | A1 | 10/2008 | Bell |
| 2008/0260656 | A1 | 10/2008 | Mallard |
| 2009/0136430 | A1 | 5/2009 | Dugger |
| 2009/0149546 | A1 | 6/2009 | Chang et al. |
| 2009/0169601 | A1 | 7/2009 | Koch et al. |
| 2010/0006600 | A1 | 1/2010 | Dascanio |
| 2010/0008996 | A1 | 1/2010 | Meinert |
| 2010/0016814 | A1 | 1/2010 | Gokhale et al. |
| 2010/0137252 | A1 | 6/2010 | Matsumura et al. |
| 2010/0189765 | A1 | 7/2010 | Erickson et al. |
| 2010/0226997 | A1 | 9/2010 | Bowman et al. |
| 2010/0274215 | A1 | 10/2010 | Wong et al. |
| 2010/0310476 | A1 | 12/2010 | Tamarkin et al. |
| 2011/0223208 | A1 | 9/2011 | Hill et al. |
| 2011/0269704 | A1 | 11/2011 | Seigfried |
| 2012/0010280 | A1 | 1/2012 | Aleo et al. |
| 2012/0053242 | A1 | 3/2012 | Cela Lopez |
| 2012/0095097 | A1 | 4/2012 | Tabuchi et al. |
| 2012/0100183 | A1 | 4/2012 | Schlessinger et al. |
| 2012/0219640 | A1 | 8/2012 | Wright |
| 2012/0238639 | A1 | 9/2012 | Theisinger et al. |
| 2012/0244177 | A1 | 9/2012 | Theisinger et al. |

(56) References Cited

U.S. PATENT DOCUMENTS

| | | |
|---|---|---|
| 2013/0011484 A1 | 1/2013 | Bevier |
| 2013/0046014 A1 | 2/2013 | Theisinger et al. |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2013/0309226 A1 | 11/2013 | Armstrong et al. |
| 2013/0336557 A1 | 12/2013 | Cruzat et al. |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0186350 A1 | 7/2014 | Ghosh et al. |
| 2014/0303219 A1 | 10/2014 | Bingaman et al. |
| 2014/0369993 A1 | 12/2014 | Günther et al. |
| 2015/0045282 A1 | 2/2015 | Elsohly et al. |
| 2015/0099019 A1 | 4/2015 | Johnson |
| 2015/0174096 A1 | 6/2015 | Bottger et al. |
| 2015/0224064 A1 | 8/2015 | Günther et al. |
| 2015/0238605 A1 | 8/2015 | Günther et al. |
| 2015/0258040 A1 | 9/2015 | Lynch et al. |
| 2016/0000941 A1 | 1/2016 | Keller et al. |
| 2016/0101178 A1 | 4/2016 | Wilson |
| 2016/0159902 A1 | 6/2016 | Günther et al. |
| 2016/0184259 A1 | 6/2016 | Anastassov et al. |
| 2016/0243189 A1 | 8/2016 | Gu et al. |
| 2016/0303031 A1 | 10/2016 | El Achkar et al. |
| 2017/0020726 A1 | 1/2017 | Labombarbe et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2017/0216204 A1 | 8/2017 | Theisinger et al. |
| 2017/0348285 A1 | 12/2017 | Hellstrom |
| 2018/0360908 A1 | 12/2018 | Beier et al. |
| 2019/0256591 A1 | 8/2019 | Günther et al. |
| 2019/0274970 A1 | 9/2019 | Günther et al. |
| 2019/0328717 A1 | 10/2019 | Günther et al. |
| 2019/0343793 A1 | 11/2019 | Günther et al. |
| 2020/0060987 A1 | 2/2020 | Günther et al. |
| 2020/0188318 A1 | 6/2020 | Günther et al. |
| 2020/0206241 A1 | 7/2020 | Theisinger et al. |
| 2020/0246463 A1 | 8/2020 | Günther et al. |
| 2020/0338015 A1 | 10/2020 | Scherer et al. |
| 2021/0069014 A1 | 3/2021 | Löscher et al. |
| 2021/0121471 A1 | 4/2021 | Löscher et al. |
| 2021/0228595 A1 | 7/2021 | Löscher et al. |
| 2021/0236591 A1 | 8/2021 | Leo et al. |
| 2021/0315832 A1 | 10/2021 | Scherer et al. |
| 2021/0340248 A1 | 11/2021 | Günther et al. |
| 2021/0346313 A1 | 11/2021 | Beier et al. |
| 2022/0008397 A1 | 1/2022 | Xu et al. |
| 2022/0031844 A1 | 2/2022 | Mauden et al. |
| 2022/0079925 A1 | 3/2022 | Günther et al. |
| 2022/0143137 A1 | 5/2022 | Witt et al. |
| 2022/0152096 A1 | 5/2022 | Löscher et al. |
| 2022/0226426 A1 | 7/2022 | Löscher et al. |
| 2022/0226427 A1 | 7/2022 | Leo et al. |
| 2022/0354786 A1 | 11/2022 | Friess et al. |
| 2022/0354926 A1 | 11/2022 | Löscher et al. |
| 2022/0362382 A1 | 11/2022 | Löscher et al. |
| 2022/0370377 A1 | 11/2022 | Scherer et al. |
| 2023/0043641 A1 | 2/2023 | Beier et al. |
| 2023/0139672 A1 | 5/2023 | Theisinger et al. |
| 2023/0181679 A1 | 6/2023 | Haisser et al. |
| 2023/0330056 A1 | 10/2023 | Günther et al. |
| 2023/0398065 A1 | 12/2023 | Günther et al. |

FOREIGN PATENT DOCUMENTS

| | | |
|---|---|---|
| CN | 202136470 U | 2/2012 |
| CN | 203524843 U | 4/2014 |
| EP | 0 089 815 A1 | 9/1983 |
| EP | 0 593 552 A1 | 4/1994 |
| EP | 0 670 159 A1 | 9/1995 |
| EP | 0 965 329 A1 | 12/1999 |
| EP | 0 965 334 A1 | 12/1999 |
| EP | 0 939 655 A1 | 6/2002 |
| EP | 1 152 749 A2 | 4/2006 |
| EP | 2 110 126 A1 | 10/2009 |
| EP | 2 332 525 A1 | 6/2011 |
| EP | 2 335 735 A1 | 6/2011 |
| EP | 2 462 921 A1 | 6/2012 |
| EP | 2 708 228 A1 | 3/2014 |
| EP | 2 730 291 A1 | 5/2014 |
| JP | S6452722 A | 2/1989 |
| JP | H0764702 B2 | 7/1995 |
| JP | 2000/511157 A | 8/2000 |
| JP | 2001/158734 A | 6/2001 |
| JP | 2008/505177 A | 2/2008 |
| JP | 2011/006348 A | 1/2011 |
| JP | 2011/024841 A | 2/2011 |
| WO | WO-93/000991 A1 | 1/1993 |
| WO | WO-95/033447 A1 | 12/1995 |
| WO | WO-96/040052 A1 | 12/1996 |
| WO | WO-97/012852 A1 | 4/1997 |
| WO | WO-98/005301 A1 | 12/1998 |
| WO | WO-00/010531 A1 | 3/2000 |
| WO | WO-00/024376 A1 | 5/2000 |
| WO | WO-00/054588 A1 | 9/2000 |
| WO | WO-2002/049631 | 6/2002 |
| WO | WO-2003/099258 | 12/2003 |
| WO | WO-2005/018530 | 3/2005 |
| WO | WO-2005/099718 | 10/2005 |
| WO | WO-2005/099752 | 10/2005 |
| WO | WO-2005/123035 | 12/2005 |
| WO | WO-2006/007510 | 1/2006 |
| WO | WO-2006/042059 | 4/2006 |
| WO | WO-2006/048242 | 5/2006 |
| WO | WO-2007/008666 | 1/2007 |
| WO | WO-2007/052288 | 5/2007 |
| WO | WO-2008/060359 | 5/2008 |
| WO | WO-2009/013435 | 1/2009 |
| WO | WO-2009/065565 | 5/2009 |
| WO | WO-2010/062394 | 6/2010 |
| WO | WO-2010/146536 | 12/2010 |
| WO | WO-2011/009436 | 1/2011 |
| WO | WO-2011/073134 | 6/2011 |
| WO | WO-2011/113855 | 9/2011 |
| WO | WO-2011/151079 | 12/2011 |
| WO | WO-2012/052418 | 4/2012 |
| WO | WO-2012/062834 | 5/2012 |
| WO | WO-2012/093113 | 7/2012 |
| WO | WO-2012/121754 | 9/2012 |
| WO | WO-2012/160179 | 11/2012 |
| WO | WO-2012/160180 | 11/2012 |
| WO | WO-2013/110621 | 8/2013 |
| WO | WO-2014/041055 | 3/2014 |
| WO | WO-2014/041071 | 3/2014 |
| WO | WO-2014/154531 | 10/2014 |
| WO | WO-2015/011199 | 1/2015 |
| WO | WO-2016/025560 | 2/2016 |
| WO | WO 2016/082644 A1 | 6/2016 |
| WO | WO-2017/055453 | 4/2017 |
| WO | WO-2017/220625 | 12/2017 |
| WO | WO-2018/060282 | 4/2018 |
| WO | WO-2018/114557 | 6/2018 |
| WO | WO-2018/115097 | 6/2018 |
| WO | 2020/074697 A1 | 4/2020 |

OTHER PUBLICATIONS

"Topical drug dosage forms for eye conditions," The Pharmaceutical Journal, (Pharmaceutical Press, May 31, 2017), available at https://pharmaceutical-journal.com/article/ld/topical-drug-dosage-forms-for-eye-conditions.

"Xerophthalmia," Eye Clinic, 4 pages, archived Dec. 30, 2014.

Agarwal et al., "Modern Approaches to the Ocular Delivery of Cyclosporine A," Drug Discovery Today, vol. 21, No. 6, pp. 977-988, (2016); doi: 10.1016/j.drudis.2016.04.002.

Ahmed, S. et al., "Ocular Drug Delivery: a Comprehensive Review," AAPS PharmSciTech, vol. 24, No. 66, pp. 1-29, (2023).

Ann Marie Griff, O.D., & Ann Pietrangelo, "Everything you need to know about keratoconjunctivitis," Healthline.com, Nov. 22, 2019, downloaded from https://www.healthline.com/health/keratoconjunctivitis.

(56)  References Cited

OTHER PUBLICATIONS

Benezra, D. et al., "Cyclosporine eyedrops for the treatment of severe vernal keratoconjunctivitis," American Journal of Ophthalmology, vol. 101, pp. 278-282, (1986).

Bron, A. et al., "Grading of Corneal and Conjunctival Staining in the Context of Other Dry Eye Tests," Cornea, vol. 22, No. 7, pp. 640-650, (2003).

Dutescu, R. et al., "Semifluorinated alkanes as a liquid drug carrier system for topical ocular drug delivery," European Journal of Pharmaceutics and Biopharmaceutics, vol. 88, No. 1, pp. 123-128, (2014).

Eva M. del Amo, "Topical ophthalmic administration: Can a drug instilled onto the ocular surface exert an effect at the back of the eye?" Frontiers in Drug Discovery 2:954771 (Sep. 8, 2022), available at https://www.frontiersin.org/articles/10.3389/fddev.2022.954771/full.

Günther, B., "Breaking the Vicious Circle of Dry Eye Disease," OIS@ SECO, Feb. 21, 2019, pp. 1-14, New Orleans, URL: https://ois.net/wp-content/uploads/2019/02/DryEye-Novaliq.pdf.

Keratoconjunctivitis, Cleveland Clinic, last updated Jul. 8, 2022, downloaded from https://my.clevelandclinic.org/health/diseases/23551-keratoconjunctivitis.

Kumar, S. et al., "Reduction in drop size of ophthalmic topical drop preparations and the impact of treatment," J. Adv. Pharm. Tech. Res., vol. 2, No. 3, (2011).

Li, Y. et al., "Limited Scleroderma (Crest Syndrome) is Associated with Worse Xerostomia and Xerophthalmia in Patients Being Evaluated for Primary Sjogren's Syndrome," Scientific Abstracts; FRI0432, pp. 583-584, (2015).

Miller, K. et al., "Minimal Clinically Important Difference for the Ocular Surface Disease Index," Socioeconomics and Health Services, Arch Ophthalmol, vol. 128, No. 1, pp. 94-101, (2010).

Moscovici, B. et al., "Clinical treatment of dry eye using 0.03% tacrolimus eye drops," Cornea, vol. 31, No. 8, pp. 945-949, (2012).

Murphy, C. et al., "Cyclosporine vs Tacrolimus Therapy for Posterior and Intermediate Uveitis," Arch Ophthalmol., vol. 123, pp. 634-641, (2005).

Qiao, J. et al., "Emerging treatment options for meibomian gland dysfunction," Clinical Ophthalmology, vol. 7, pp. 1797-1803, (2013).

RESTASIS® Prescribing Information, available at https://www.accessdata.fda.gov/drugsatfda_docs/label/2012/050790s020lbl.pdf (Nov. 2012) (last accessed Feb. 28, 2023).

Sheppard, J. et al., "A Water-free 0.1% Cyclosporine A Solution for Treatment of Dry Eye Disease: Results of the Randomized Phase 2B/3 ESSENCE Study," Cornea, vol. 40, No. 10, pp. 1290-1297, (2021).

Steven, P. et al., "Semifluorinated Alkane Eye Drops for Treatment of Dry Eye Disease—A Prospective, Multicenter Noninterventional Study," Investigative Ophthalmology & Visual Science, vol. 56, p. 4493, (2015), Abstract Only.

Torkildsen, G. et al., "A Clinical Phase 2 Study to Assess Safety, Efficacy, and Tolerability of CyclASol for the Treatment of Dry Eye Disease," Poster Presentation at American Academy of Ophthalmology (AAO), New Orleans, (2017).

Agarwal, P. et al., "Semifluorinated alkane based systems for enhanced corneal penetration of poorly soluble drugs," International Journal of Pharmaceutics, vol. 538, No. 1-2, pp. 119-129, (2018).

Ganka, A., "Definition and Diagnostic Criteria for Meibomian Gland Dysfunction," Journal of Ophthalmology, vol. 27, No. 5, pp. 627-631, 6 pages, (2010), abstract only.

Pensyl, D., "Chapter 14: Preparations for Dry Eye and Ocular Surface Disease," Clinical Ocular Pharmacology, Fifth Edition, pp. 263-278, 18 pages, (2008).

Santvliet, L. et al., "Determinants of Eye Drop Size," Survey of Ophthalmology, vol. 49, No. 2, pp. 197-213, (2004).

Schmitt, M., "Chapter 10: Design and Development of Ocular Formulations for Preclinical and Clinical Trials," Innovative Dosage Forms: Design and Development at Early Stage, pp. 331-365, 35 pages, (2020).

Zeev, M. et al., "Diagnosis of dry eye disease and emerging technologies," Clinical Ophthalmology, vol. 8, pp. 581-590, 11 pages, (2014).

"Novaliq GmbH Begins Phase II Clinical Trial of Cyclasol for the Treatment of Moderate to Severe Dry Eye Disease," (online), 5 pages, (2016); retrieved on Jan. 8, 2021 from the Internet: https://www.biospace.com/article/releases/novaliq-gmbh-begins-phase-ii-clinical-trial-of-cyclasol-for-the-treatment-of-moderate-to-severe-dry-eye-disease-/.

"What is retinal vitrectomy?", Presented by: Medical Online, Obesity and Diabetes Mellitus, vol. 4, No. 2, pp. 284-286, (2005).

"EvoTears—Gebrauchsanweisung," May 2015, retrieved from the Internet, date retrieved: Jun. 26, 2018, 2 pages, URL: http://video.apo-rot.de/docs/11213615.pdf.

"Novaliq Announces Positive Topline Results of Phase 2 Clinical Trial Evaluating CyclASol® in Adults with Moderate to Severe Dry Eye Disease," Businesswire, Jan. 5, 2017, URL: <https://www.businesswire.com/news/home/20170105005211/en/Novaliq-Announces-Positive-Topline-Results-Phase-2>.

"Novaliq begins Phase 2 trial of Cyclasol for dry eye disease," Optometry Times, vol. 8, No. 3, (2016), p. 24.

"Semifluorinated alkane technology brings advantages for topical therapy," Ophthalmology Times, 2016, pp. 1-2.

Agrahari, et al., "A comprehensive insight on ocular pharmacokinetics," Drug Delivery and Translational Research, vol. 6, No. 6, pp. 735-754, (2016).

Ahmed, I. et al., "Disposition of Timolol and Inulin in the Rabbit Eye Following Corneal Versus Non-Corneal Absorption," International Journal of Pharmaceutics, vol. 38, pp. 9-21, (1987).

Baerdemaeker, L. et al., "Pharmacokinetics in Obese Patients," Continuing Education in Anaesthesia, Critical Care & Pain, vol. 4, pp. 152-155, (2004).

Bardin et al., "Long-Range Nanometer-Scale Organization of Semifluorinated Alkane Monolayers at the Air/Water Interface," Langmuir, vol. 27, pp. 13497-13505, (2011).

Bertilla et al., "Semifluorinated Alkanes as Stabilizing Agents of Fluorocarbon Emulsions," Springer, vol. 12, 24 pages, (2005).

Blackie et al., "Getting to the Root Cause of Dry Eye", Review of Optometry, pp. 1-12, (2012).

Broniatowski, M. et al., "Langmuir Monolayers Characteristic of (Perfluorodecyl)-Alkanes," Journal of Physical Chemistry B, vol. 108, pp. 13403-13411, (2004).

Chao, W. et al., "Report of the Inaugural Meeting of the TFOS i2 = initiating innovation Series: Targeting the Unmet Need for Dry Eye Treatment," (London, United Kingdom, Mar. 21, 2015) Accepted Manuscript, Accepted Date: Nov. 11, 2015, 94 pages.

Chemical Book, 5-Fluorouracil, available at <http://www.chemicalbook.com/ChemicalProductProperty_EN_CB8162744.htm>, 1 page, accessed Mar. 7, 2014.

Chhadva et al., "Meibomian Gland Disease The Role of Gland Dysfunction in Drye Eye Disease," Ophthalmology, vol. 124, No. 11 Supplement, pp. S20-S26, (2017).

Costa Gomes et al., "Solubility of dioxygen in seven fluorinated liquids," Journal of Fluorine Chemistry, vol. 125, pp. 1325-1329, (2004).

Davies, N., "Biopharmaceutical Considerations in Topical Ocular Drug Delivery," Clinical and Experimental Pharmacology and Physiology, vol. 27, pp. 558-562, (2000).

Dembinski, R. et al., "Semi-fluorinated Alkanes as Carriers for Drug Targeting in Acute Respiratory Failure," Experimental Lung Research, vol. 36, pp. 499-507, (2010).

Deschamps, J. et al., "Solubility of oxygen, carbon dioxide and water in semifluorinated alkanes and in perfluorooctylbromide by molecular simulation", Journal of Fluorine Chemistry, Elsevier, vol. 125, No. 3, (2004).

Dias et al., "Solubility of oxygen in liquid perfluorocarbons," Fluid Phase Equilibria, vol. 222-223, pp. 325-330, (2004).

Dutescu et al., "Semifluorinated alkanes as a liquid drug carrier system for topical ocular drug delivery," European Journal of Pharmaceutics and Biopharmaceutics, vol. 88, No. 1, pp. 123-128, (2014), (Abstract Only).

Elkeeb, R. et al., "Transungual Drug Delivery: Current Status," International Journal of Pharmaceutics, vol. 384, pp. 1-8, (2010).

(56)                    References Cited

OTHER PUBLICATIONS

English-language machine translation of EP0670159 (A1) issued in U.S. Appl. No. 14/122,025 on Apr. 1, 2015, 10 pages.
Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages.
Gayton, J., "Etiology, Prevalence, and Treatment of Dry Eye Disease," Clinical Ophthalmology, vol. 3, pp. 405-412, (2009).
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., vol. 255, No. 4, pp. 767-775, (2017).
Gehlsen, U., et al., "Omega-3 Fatty Acids Using F6H8-Carrier as Topical Therapy in Experimental Dry-Eye Disease," Investigative Ophthalmology & Visual Science, vol. 57, pp. 417, (2016), (Abstract Only).
Gehlsen. U., et al., "Cyclosporine A using F4H5 as liquid drug carrier is effective in treating experimental dry-eye disease," Investigative Ophthalmology & Visual Science, vol. 56, No. 319, (2015), (Abstract Only).
Gerdenitsch, "Emulsions—established and promising drug carriers for parenteral adminstration", retrieved from internet: http:/ipimediaworld.com/wp- content/uploads/2012/05/Pages-from-IPI-Volume-2-Issue- I - I I .pdf. Date Accessed: Jul. 20, 2016.
German, E.J., et al., "Reality of drop size from multi-dose eye drop bottles: is it cause for concern?" Eye, vol. 13, pp. 93-100, (1999).
Griffin, W., "Classification of Surface-Active Agents by 'HLB'," Journal of the Society of Cosmetic Chemists, vol. 1, pp. 311-326, (1949).
Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).
Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf (retrieved on Oct. 10, 2011).
Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, vol. 239, No. 5, pp. 373-381, (2001).
Holm, R. et al., "A novel excipient, 1-perfluorohexyloctane shows limited utility for the oral delivery of poorly water-soluble drugs," European Journal of Pharmaceutical Sciences, vol. 42, pp. 416-422, (2011).
International Preliminary Report on Patentability dated Apr. 2, 2019, for International Application No. PCT/EP2017/074545, 7 pages.
International Preliminary Report on Patentability dated Dec. 25, 2018, for International Application No. PCT/EP2017/065163, 6 pages.
International Preliminary Report on Patentability dated Jan. 26, 2016, for International Application No. PCT/EP2014/065840, 11 pages.
International Preliminary Report on Patentability dated Jun. 25, 2019, for International Application No. PCT/EP2017/082739, 7 pages.
International Preliminary Report on Patentability dated Mar. 26, 2019, for International Application No. PCT/EP2017/073697, 7 pages.
International Preliminary Report on Patentability dated Mar. 26, 2019, for International Application No. PCT/EP2017/074079, 7 pages.
International Preliminary Report on Patentability for International Application No. PCT/EP2011/068141 dated Apr. 23, 2013, 4 pages.
International Preliminary Report on Patentability for International Application No. PCT/EP2011/069795 dated May 14, 2013, 8 pages.
International Preliminary Report on Patentability for International Application No. PCT/EP2012/050043 dated Jul. 10, 2013, 5 pages.

International Preliminary Report on Patentability for International Application No. PCT/EP2012/059787 dated Nov. 26, 2013, 9 pages.
International Preliminary Report on Patentability for International Application No. PCT/EP2012/059788 dated Nov. 26, 2013, 8 pages.
International Preliminary Report on Patentability for International Application No. PCT/EP2013/051163 dated Jul. 29, 2014, 7 pages.
International Preliminary Report on Patentability for International Application No. PCT/EP2013/068882 dated Mar. 17, 2015, 5 pages.
International Preliminary Report on Patentability for International Application No. PCT/EP2013/068909 dated Mar. 17, 2015, 7 pages.
International Preliminary Report on Patentability issued Sep. 18, 2012, for International Patent Application PCT/EP2011/053949, 9 Pages.
International Search Report and Written Opinion for International Application No. PCT/EP2017/083770 mailed Jul. 6, 2018, 14 pages.
International Search Report and Written Opinion for International Application No. PCT/EP2018/076908 mailed Dec. 12, 2018, 11 pages.
International Search Report for International Application No. PCT/EP2011/053949 mailed Sep. 6, 2011, 5 pages.
International Search Report for International Application No. PCT/EP2011/068141 mailed Dec. 14, 2011, 2 pages.
International Search Report for International Application No. PCT/EP2011/069795 mailed Jan. 16, 2012, 3 pages.
International Search Report for International Application No. PCT/EP2012/050043 mailed Apr. 24, 2012, 2 pages.
International Search Report for International Application No. PCT/EP2012/059787 mailed Dec. 5, 2012, 4 pages.
International Search Report for International Application No. PCT/EP2012/059788 mailed Dec. 3, 2012, 4 pages.
International Search Report for International Application No. PCT/EP2013/051163 mailed Mar. 4, 2013, 4 pages.
International Search Report for International Application No. PCT/EP2013/068882 mailed Oct. 30, 2013, 4 pages.
International Search Report for International Application No. PCT/EP2013/068909 mailed Dec. 5, 2013, 4 pages.
International Search Report for International Application No. PCT/EP2014/065840 mailed Oct. 7, 2014, 4 pages.
International Search Report for International Application No. PCT/EP2016/073263 mailed Dec. 23, 2016, 3 pages.
International Search Report for International Application No. PCT/EP2017/065163, mailed Aug. 8, 2017, 3 pages.
International Search Report for International Application No. PCT/EP2017/073697 mailed Nov. 6, 2017, 4 pages.
International Search Report for International Application No. PCT/EP2017/074079 mailed Dec. 22, 2017, 4 pages.
International Search Report for International Application No. PCT/EP2017/074545 mailed Nov. 28, 2017, 3 pages.
International Search Report for International Application No. PCT/EP2017/082739 mailed Mar. 6, 2018, 3 pages.
International Search Report for International Application No. PCT/EP2017/083770 (revised version) mailed Jul. 6, 2018, 4 pages.
Ishizaki et al., "Treatment of Diabetic Retinopathy", Forum: Complication, Practice, vol. 26, No. 5, pp. 474-476, (2009).
JP 2000511157 A, English Machine Translation of the Abstract, Description, and Claims, Espacenet, Date Accessed: Feb. 10, 2016.
JPH0764702b2, Kanebo Ltd, "Cosmetic of Polyphasic Emulsion Type," Jul. 12, 1995, English language machine translation of abstract, Espacenet, date obtained: Apr. 30, 2021, 1 page <https://worldwide.espacenet.com/patent/search/family/014142733/publication/JPH0764702B2?q=JPH0764702B2>.
JPS6452722, English Machine Translation of the Abstract, Description, and Claims, Espacenet, Date Accessed: Feb. 10, 2016.
Kaercher et al., "Nova Tears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.
Kerns et al., Drug-Like Properties: Concepts, Structure Design and Methods: from ADME to Toxicity Optimization, Elsevier, Chapter 10, Section 10.4.3, 133, (2008).

(56) References Cited

OTHER PUBLICATIONS

Knepp, V. et al., "Stability of Nonaqueous Suspension Formulations of Plasma Derived Factor IX and Recombinant Human Alpha Interferon at Elevated Temperatures," Pharmaceutical Research, vol. 15, No. 7, pp. 1090-1095, (1998).

Kociok, N., et al., "Influence on Membrane-Mediated Cell Activation by Vesicles of Silicone Oil or Perfluorohexyloctane," Graefe's Archive for Clinical and Experimental Ophthalmology, vol. 243, pp. 345-358, (2005).

Lallemand et al., "Cyclosporine A delivery to the eye: a pharmaceutical challenge," European Journal of Pharmaceutics and Biopharmaceutics, Abstract Only, 1 page, vol. 56, No. 3, pp. 307-318, (2003).

Lallemand et al., "Cyclosporine Delivery to the Eye: A comprehensive Review of Academic and Industrial Efforts," European Journal of Pharmaceutics and Biopharmaceutics,, vol. 117, pp. 14-28, (2017).

Lemp, M., "Management of Dry Eye Disease," The American Journal of Managed Care, vol. 14, No. 3, pp. S88-S101, (2008).

Lin, H. et al., "Dry eye disease: A review of diagnostic approaches and treatments," Saudi Journal of Ophthalmology, vol. 28, pp. 173-181, (2014).

Mackiewicz, J. et al., "In Vivo Retinal Tolerance of Various Heavy Silicone Oils," Investigative Ophthalmology & Visual Science, vol. 48, No. 4, pp. 1873-1883, (2007).

Martin-Montañez et al., "End-of-day dryness, corneal sensitivity and blink rate in contact lens wearers," Cont Lens Anterior Eye, vol. 38, No. 3, pp. 148-151, (2015).

Matteucci et al., "Biocompatibility assessment of liquid artificial vitreous replacements: relevance of in vitro studies," Survey of Ophthalmology, vol. 52, No. 3, pp. 289-299, (2007), (Abstract Only).

Meinert, H. et al., "Semifluorinated Alkanes—A New Class of Compounds with Outstanding Properties for Use in Ophthalmology," European Journal of Ophthalmology, vol. 10, No. 3, pp. 189-197, (2000).

Meinert, H. et al., "The Use of Semifluorinated Alkanes in Blood-Substitutes," Biomaterials, Artificial Cells, and Immobilization Biotechnology, vol. 21, No. 5, pp. 583-595, (1993).

Messmer, E.M., "The Pathophysiology, Diagnosis, and Treatment of Dry Eye Disease," Deutsches Arzteblatt International, vol. 112, No. 5, pp. 71-82, (2015).

Messmer, et al. "Semifluorierte Alkane als Therapie bei Meibomdrüsen-Dysfunktion Ergebnisse einer prospektiven, multizentrischen Beobachtungsstudie," DOG-Kongress, Sep. 29-Oct. 2, 2016, Berlin DOG (Deutsche Ophtalmologische Gesellschaft), Poster PSa03-02, (German language version).

Messmer, et al. "Semifluorinated Alkanes as a Therapy for Meibomian Gland Dysfunction Results of a prospective, multi-centered observational study," DOG-Kongress, Sep. 29-Oct. 2, 2016, Berlin DOG (Deutsche Ophtalmologische Gesellschaft), Ophthalmologe, Aug. 2016, Poster PSa03-02, English Abstract, p. 138.

Messmer, et al. "Semifluorinated Alkanes as a Therapy for Meibomian Gland Dysfunction Results of a prospective, multi-centered observational study," Presentation, DOG-Kongress, Sep. 29-Oct. 2, 2016, Berlin DOG (Deutsche Ophtalmologische Gesellschaft), Poster: PSa03-02, English Translation, 6 pages.

Murdan, S., "Enhancing the Nail Permeability of Topically Applied Drugs," Expert Opinion on Drug Delivery, vol. 5, No. 11, pp. 1267-1282, (2008).

O'Rourke, M. et al., "Enhancing Delivery of Topical Ocular Drops," Cataract & Refractive Surgery Today Europe, 2 pages, (2016).

Perry, H., "Dry Eye Disease: Pathophysiology, Classification, and Diagnosis," The American Journal of Managed Care, vol. 14, No. 3, pp. S79-S87, (2008).

Pflugfelder et al., "The Pathophysiology of Dry Eye Disease What We Know and Future Directions for Research," Ophthalmology, vol. 124, No. 11 Supplement, pp. S4-S13, (2017).

Pflugfelder et al., "Treatment of Blepharitis: Recent Clinical Trials," vol. 12, No. 4, 2 pages, pp. 273-284, (2014), (Abstract Only).

Pinarci, E. et al., "Intraocular Gas Application in the Diagnosis and Treatment of Valsalva Retiopathy in Case with Premacular Hemorrhage," XP002625604, Retina-Vitreus, vol. 17, No. 2, pp. 153-155, (2009), (Abstract Only).

Plassmann, M. et al., "Theoretical and Experimental Simulation of the Fate of Semifluorinated n-Alkanes During Snowmelt," Environmental Science & Technology, vol. 44, No. 17, pp. 6692-6697, (2010).

Plassmann, M. et al., "Trace Analytical Methods for Semifluorinated n-Alkanes in Snow, Soil, and Air," Analytical Chemistry, vol. 82, No. 11, pp. 4551-4557, (2010).

Rosca-Casian, O. et al., "Antifungal Activity of Aloe Vera Leaves," Fitoterapia, vol. 28, pp. 219-222, (2007).

Rosenberg, A., "Effects of Protein Aggregates: An Immunologic Perspective," The AAPS Journal, vol. 8, No. 3, pp. E501-E507, (2006).

Sall, K. et al. "Two Multicenter, Randomized Studies of the Efficacy and Safety of Cyclosporine Ophthalmic Emulsion in Moderate to Severe Dry Eye Disease," Ophthalmology, vol. 107, No. 4, pp. 631-639, (2000).

Scherer et al., "Eyesol: A Novel Topical Ocular Drug Delivery System for Poorly Soluble Drugs," Drug Development & Delivery, vol. 13, No. 1, pp. 40-44, (2013).

Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, vol. 19, pp. 4889-4894, (2003).

Schnetler et al., "Lipid composition of human meibum: a review", S Afr Optom, vol. 72, No. 2, pp. 86-93, (2013).

Spöler et al., "Towards a New in vitro Model of Dry Eye: The ex vivo Eye Irritation Test", Developments in Ophthalmology, vol. 45, pp. 93-107, (2010).

Steven et al., "Semifluorinated Alkane Eye Drops for Treatment of Dry Eye Disease Due to Meibomian Gland Disease," Journal of Ocular Pharmacology and Therapeutics, vol. 33, No. 9, pp. 1-8, (2017).

Steven, P. et al. "Semifluorinated Alkane Eye Drops for Treatment of Dry Eye Disease - A Prospective, Multicenter Noninterventional Study" Journal of Ocular Pharmacology and Therapeutics, vol. 31, No. 8, pp. 498-503, (2015).

Stevenson, C., "Characterization of Protein and Peptide Stability and Solubility in Non-Aqueous Solvents," Current Pharmaceutical Biotechnology, vol. 1, pp. 165-182, (2000).

Tamura et al., "Tacrolimus is a class II low-solubility high-permeability drug: The effect of P-glycoprotein efflux on regional permeability of tacrolimus in rats," Journal of Pharmaceutical Sciences, vol. 91, No. 3, pp. 719-729, 1 page, (2002), (Abstract Only).

Tiffany, J.M., "Individual Variations in Human Meibomian Composition", Exp. Eye Res., vol. 27, pp. 289-300, (1978).

Troiano et al., "Effect of Hyptonic .4% Hyaluronic Acid Drops in Dry Eye Patients: A Cross-Study", Cornea, vol. 27, No. 10, pp. 1126-1130, (2008), (Abstract Only).

Wang, W., "Lyophilization and Development of Solid Protein Pharmaceuticals," International Journal of Pharmaceutics, vol. 203, pp. 1-60, (2000).

Wirta, David L. et al., "A Clinical Phase II Study to Assess Efficacy, Safety and Tolerability of Waterfree Cyclosporine Formulation for the Treatment of Dry Eye Disease," Ophthalmology, vol. 126, pp. 792-800, (2019).

Wong, D. et al., "Perfluorocarbons and Semifluorinated Alkanes," Seminars in Ophthalmology, vol. 15, No. 1, pp. 25-35, (2000).

Xalatan, Latanoprost Ophthalmic Solution, 50 µg/mL Prostaglandin F 2α analogue, Product Monograph, 30 pages,(2014).

Yaoxue Zhuanye Zhishi II (Editor: Jin Xiangqun), Military Medical Science Press, 1st Printing of 2nd Edition, Mar. 2009, p. 158.

Yaoxue Zhuanye Zhishi II (Editor: Jin Xiangqun), Military Medical Science Press, 1st Printing of 2nd Edition, Mar. 2009, p. 158, 3 pages, (English Machine Translation).

Zeng, Y., "Atlas of Clinical Keratoconjunctival Disease," Hubei Science and Technology Press, p. 287-299, (2011).

(56)          References Cited

OTHER PUBLICATIONS

Zeng, Y., "Atlas of Clinical Keratoconjunctival Disease," Hubei Science and Technology Press, p. 287-299, (2011), English Translation.

Zhang et al., "Dry Eye Management: Targeting the Ocular Surface Microenvironment," International Journal of Molecular Sciences, vol. 18, p. 1398, (2017).

Zhang et al., "Surface micelles of semifluorinated alkanes in Langmuir-Blodgett monolayers," Phys. Chem. Chem. Phys., vol. 6, pp. 1566-1569, (2004).

"PharmaNews," Kompass Ophthalmologie, vol. 2, No. 2, pp. 98-99, (2016).

English language machine translation for "PharmaNews," Kompass Ophthalmologie, vol. 2, No. 2, pp. 98-99, (2016).

Eom, Y. et al., "Comparison of Meibomian Gland Loss and Expressed Meibum Grade Between the Upper and Lower Eyelids in Patients With Obstructive Meibomian Gland Dysfunction," Cornea, vol. 33, No. 5, 6 pages, (2014).

Foulks, G. et al., "Improving Awareness, Identification, and Management of Meibomian Gland Dysfunction," Ophthalmology, Supplement, vol. 119, No. 10, pp. S1-S12, (2012), https://doi.org/10.1016/j.ophtha 2012.06.064.

Noecker, R., "Effects of Common Ophthalmic Preservatives on Ocular Health," Advances in Therapy, vol. 18, No. 5, pp. 205-215, (2001), https://doi.org/10.1007 /BF02853166.

Tauber, J. et al., "A Randomized Clinical Study (SEECASE) to Assess Efficacy, Safety, and Tolerability of Nov. 03 for Treatment of Dry Eye Disease," Cornea, vol. 40, No. 9, pp. 1132-1140, (2021).

"Ocular and Systemic Distribution of 14C-Perfluorohexyloctane following Topical Ocular Administration to Rabbits," ARVO Annual Meeting Abstracts, Investigative Ophthalmology & Visual Science, Jul. 2018, vol. 59, Issue 9, p. 2656.

"Ocular and Systemic Distribution of 14C-Perfluorohexyloctane following Topical Ocular Administration to Rabbits," Poster A0383, 2018 ARVO Annual Meeting (Apr. 29-May 3, 2018).

Hessen, M. et al., "Dry Eye: an Inflammatory Ocular Disease," Journal of Ophthalmic and Vision Research, vol. 9, No. 2, 11 pages, (2014).

Narayanan, S. et al., "Dry Eye Disease and Microbial Keratitis: Is There a Connection?," Clinical Science, The Ocular Surface, vol. 11, No. 2, 18 pages (2013).

Schmidl, D. et al., "Influence of Perfluorohexyloctane Eye Drops on Tear Film Thickness in Patients with Mild to Moderate Dry Eye Disease: A Randomized Controlled Clinical Trial," Journal of Ocular Pharmacology and Therapeutics, vol. 36, No. 3, 8 pages, (2020).

(a) Total Corneal Fluorescein Staining (change from baseline on NEI scale)

(b) Central Corneal Fluorescein Staining (change from baseline on NEI scale)

(c) Nasal Corneal Fluorescein Staining (change from baseline on NEI scale)

(d) Temporal Corneal Fluorescein Staining (change from baseline on NEI scale)

OPHTHALMIC COMPOSITIONS COMPRISING F6H8

CROSS-REFERENCE TO RELATED APPLICATIONS

This application is a continuation of U.S. application Ser. No. 16/753,701, filed on Apr. 3, 2020, which is a U.S. national stage application filed under 35 U.S.C. § 371 of International Application No. PCT/EP2018/076908, filed on Oct. 3, 2018, which claims priority to, and the benefit of, U.S. Provisional Application Ser. No. 62/568,138, filed on Oct. 4, 2017, the contents of each of which are incorporated herein by reference in their entireties.

FIELD

The present disclosure is in the field of ophthalmic compositions comprising semifluorinated alkanes which are useful in the treatment keratoconjunctivitis sicca and/or Meibomian gland dysfunction and symptoms associated therewith, which methods may provide for the enrichment of an ophthalmic tissue in the semifluorinated alkane. In some embodiments, the invention provides a method of delayed release of the semifluorinated alkane from the enriched ophthalmic tissue to the surface of the cornea and/or conjunctiva, and/or to the Meibomian glands.

BACKGROUND

Keratoconjunctivitis sicca, also known as dry eye disease (DED), or dysfunctional tear syndrome, is a multifunctional disorder of the tear film, and ocular surface which results in discomfort, visual disturbance, and often even in ocular surface damage. Its prevalence differs widely by regions and is estimated to range from about 7.4% in the USA to about 33% in Japan (J. L. Gayton, Clinical Ophthalmology 2009:3, 405-412). According to another estimate, approximately 3.2 million women and 1.05 million men suffer from keratoconjunctivitis sicca in the USA alone. If symptomatically mild cases are also considered, there could be as many as 20 million affected people in the USA.

The main physiological function of the tear film is the lubrication of the ocular surface and the inner eyelid. In addition, it supplies the ocular surface with the nutrients which it requires, and provides a smooth and regular optical surface for the eye. Moreover, the tear film protects the ocular surface against pathogens by various mechanisms, including mechanical removal of foreign particles and through antimicrobial substances which it contains. Consequently, the loss in dynamic stability of the structure, composition, volume and distribution, as well as clearance of the tear film can lead to the development of dry eye disease.

The tear film is a dynamic structure composed of a mucous component, an aqueous component, and a lipid component. The innermost layer of the film is the mucous layer or component, which is bound to the ocular epithelium via the interaction of mucin molecules which are produced by conjunctival goblet cells and by stratified squamous cells of the conjunctiva and the cornea. The lubricating effect of the tear film is substantially based on the mucous layer and its composition.

On top of the mucous layer is the aqueous layer which is produced by the main and accessory lacrimal glands. Its primary function is to hydrate the mucous component and contribute to the transport of nutrients, electrolytes, antibacterial compounds, and oxygen to the ocular surface. The aqueous component contains water, electrolytes, lysozyme, lactoferrin, immunoglobulins (in particular IgA), retinol, hepatocyte growth factor, epidermal growth factor as its important constituents.

The outermost layer is the lipid layer, covering the aqueous layer. The lipid layer is formed from meibum (a complex mixture of polar and non-polar lipids including wax and cholesterol esters, phospholipids, di- and tri-glycerides and hydrocarbons) secreted by the Meibomian (tarsal) glands which are positioned at the tarsal plates of the eyelids, and to some degree also by the glands of Zeis which open into the eyelash follicles. The lipid mixture, which has a low melting point and remains fluid at tissue and corneal temperature, is secreted into the marginal reservoirs of the upper and lower eyelid margins. It is understood that the blinking action helps to promote the spreading and mixing of the lipids in the lipid layer. The major role of the lipid layer is primarily to reduce the rate of evaporation of the aqueous layer by evaporation, but it also functions to enhance enhancing the spreading of the tear film, to form a barrier to prevent tear film contamination, and to provide a clear optical surface. It has been proposed that increased tear film stability is associated with a thicker tear film lipid layer. Patients suffering from keratoconjunctivitis sicca (dry eye disease), in particular patients with dysfunctional Meibomian glands, have been shown to have meibum of abnormal composition compared to that seen in healthy eyes.

Keratoconjunctivitis sicca is a complex, multifunctional disorder involving several interacting pathophysiological mechanisms which are only beginning to be understood (H. D. Perry, Am. J. Man. Care 13:3, S79-S87, 2008). Two accepted mechanisms, which may reinforce each other, are tear hyperosmolarity and tear film instability. Hyperosmolar tear fluid can result from excessive tear film evaporation or reduced aqueous flow. This results in an inflammatory cascade and causes the release of inflammatory mediators into the tear fluid, with multiple pathophysiological effects eventually leading to further increased tear film evaporation and tear film instability. Thus, tear film instability can be a consequence of hyperosmolarity. Alternatively, tear film instability can also develop through its own etiological pathway, for example via abnormalities of the lipid layer composition, such as from Meibomian gland disease.

The inflammation cycle is one of the key processes that maintain and potentially progress the dry eye disease. Depending on the severity of the condition, patients often develop a reversible squamous metaphase and punctate erosions of the ocular epithelium. Secondary diseases whose development may be triggered by dry eye disease include filamentary keratitis, microbial keratitis, corneal neovascularisation, and ocular surface keratinisation.

Two major categories of dry eye disease (DED) are distinguished today, which are aqueous-deficient DED and evaporative DED. These conditions are not necessarily mutually exclusive.

Within the class of aqueous-deficient forms of DED, two major subtypes are differentiated, Sjögren and non-Sjögren. Sjögren syndrome patients suffer from autoimmune disorders in which the lacrimal glands are invaded by activated T-cells, which leads not only to keratoconjunctivitis sicca but also to a dry mouth condition. Non-Sjögren patients suffering from an aqueous-deficient DED usually have a lacrimal gland insufficiency, lacrimal duct obstruction or reflex hyposecretion.

The second major class, evaporative DED, is also somewhat heterogeneous and can develop as a result of diverse root causes. Causes associated with increased evaporative loss of the tear film include Meibomian gland disease or dysfunction, eyelid aperture disorders, blink disorders (as in Parkinson disease) or ocular surface disorders (as in allergic conjunctivitis). In particular, Meibomian gland diseases and dysfunctions are prevalently associated with evaporative dry eye disease. For example, Meibomian gland dysfunction (also abbreviated as MGD) can result in changes in the quantitative or qualitative secretion of the lipid components required for the tear film. The meibum can also have an altered composition, enriched in some components and/or deficient in other components, compared to normal meibum. This may result in altered physical properties, such as abnormal viscosity or abnormal solubility. This in turn can lead to a failure in forming a stable and continuous tear film, which is followed by evaporative loss and hyperosmolarity. Meibomian gland dysfunction can often be characterized by gland obstruction and clogging through hyperkeratinisation of the gland and increased viscosity of the meibum. Dysfunction can arise from a primary lid-margin related disease or a secondary disease arising from systemic disorders such as acne rosacea or seborrheic dermatitis.

The management of dry eye disease relies on both non-pharmacological and pharmacological approaches and the therapeutic options depend significantly on the severity of the disease state (M. A. Lemp, Am. J. Man. Care 14:3, S88-S101, 2008).

Pharmacological treatments are required for moderate to more severe forms of keratoconjunctivitis sicca. However, there are presently few pharmacological therapies available which have proven to be effective and/or which have been authorized by regulatory agencies. In the U.S., the major pharmacological treatment for moderate to severe kerato-conjunctivitis sicca is with ciclosporin (i.e. ciclosporin A, also known as cyclosporine A), which is an approved medicine in the form of an ophthalmic emulsion (Restasis®) for increasing "tear production in patients whose tear production is presumed to be suppressed due to ocular inflammation associated with keratoconjunctivitis sicca." (Restasis prescribing information).

Non-pharmacological approaches to treating dry eye disease and its symptoms are used initially when only mild symptoms occur, but also as palliative measures to support pharmacological and medical interventions. Non-pharmacological approaches may include the avoidance of exacerbating factors such as dry air, wind and drafts, tobacco smoke, modification of working habits; eye lid hygiene; tear supplementation; physical tear retention by punctal plugs or therapeutic contact lenses. In the case of dry eye disease exacerbated or caused by Meibomian gland dysfunction, traditional measures such as heat compresses, eye lid massaging or forced expression of the glands are also often recommended.

The mainstay of non-pharmacological DED treatment is the use of artificial tears for tear substitution. Most of the available products are designed as lubricants. In addition, they may function as carriers for nutrients and electrolytes (importantly, potassium and bicarbonate), and some products attempt to correct physical parameters such as an increased osmolarity in certain forms of DED. The major functional component of artificial tear compositions is an agent which increases or adjusts the viscosity, so as to increase retention time on the ocular surface and which at the same time also exhibits lubricant functionality. Common compounds used for this purpose include carboxymethyl-cellulose and its sodium salt (CMC, carmellose), polyvinyl alcohol, hydroxypropyl methylcellulose (HPMC, hypromellose), hyaluronic acid and its sodium salt, and hydroxypropyl guar gum.

Some artificial tears comprise lipids as substitutes for the lipid component, with the intention of mimicking the lipid layer of the natural tear film in order to decrease the rate of tear fluid evaporation. For example, U.S. Pat. No. 5,981,607 discloses compositions for the alleviation of symptoms related to dry eye based emulsions with higher fatty glycerides such as castor oil, corn oil or sunflower oil or light mineral oil. These types of lipids are, however, physically and biochemically poorly related to native lipid compositions. Also, the exact fate of an emulsion mixed with tear fluid in a physiological setting is not completely predictable, especially in view of the variability in volume and content of the tear film in patients with dry eye disease.

In general, one of the disadvantages of such formulations comprising oil for ophthalmic administration is that these inherently may have a negative impact on vision. Whether used as oily solutions or oil-in-water emulsions, they exhibit a refractive index which differs substantially from that of physiological tear fluid, which leads to visual disturbances and blurring.

Also, in contrast to single phase systems, emulsions may be more complex and difficult to manufacture, especially in sterile form. Frequently, emulsions are not readily sterilisable by thermal treatment without negative impact on the physical properties of the emulsion. On the other hand, aseptic processing is complex, costly, and is associated with higher risks of failure, i.e. microbial contamination. Oil-in-water emulsions are also more prone to microbial contamination during use.

Preservatives which can be used in ophthalmic formulations are potentially damaging to the eye, in particular to the ocular surface, and should be avoided in the context of dry eye disease. This is particularly relevant for patients with moderate to severe dry eye disease symptoms who may require frequent use for symptom relief, as well as patients who require multiple preserved topical medicaments.

Some manufacturers have attempted to obviate the preservative issue by relying on single-dose containers for the administration of non-preserved formulations were developed. These are however less cost-efficient and convenient to handle for the patient than the conventional multi-dose bottle. Furthermore, ophthalmic formulations utilizing 'vanishing' preservatives such as sodium chlorite or sodium perborate, which can convert to non-toxic ions and water after instillation and contact with the tear film, may still be irritating to patients especially those with severe disease who may not have sufficient tear volume to effectively degrade the preservatives.

WO 2011/073134 discloses ophthalmic topical pharmaceutical compositions comprising immunosuppressant macrolides such as ciclosporin A and semifluorinated alkanes, for treatment of keratoconjunctivitis sicca. The semifluorinated alkanes in the disclosed compositions serve as suitable liquid vehicles for delivering the therapeutic pharmaceutical agent to the eye, and in particular have a high capacity for dissolving poorly soluble compounds such as ciclosporin. In this role, however, the semifluorinated alkane is merely taught as pharmaceutically inactive solvent for the active therapeutic agent.

U.S. Pat. No. 7,001,607 discloses a polyaphron gel tear substitute containing at least one water-soluble fluorinated surfactant, water, and a non-polar component, in which the nonpolar component can be fluorocarbon or a silicone oil. The gel compositions are specifically administered into the conjunctival sac to form a gel reservoir, and are only spread over the cornea of the eye as a liquid film over the cornea as a result of blinking action. For patients with dry eye symptoms caused by eyelid/blink disorders (e.g. as a result of Parkinson's disease), such compositions are therefore not useful.

US 2015-0224064A1 discloses semifluorinated alkane compositions for the treatment of dry eye disease, as well as symptoms and conditions associated therewith. The disclosed invention is directed primarily to compositions comprising a mixture of at least two different semifluorinated alkanes. These compositions may be administered to the eye or ophthalmic tissues, such as, in patients suffering from keratoconjunctivitis sicca and/or Meibomian gland dysfunction. The publication does not disclose or suggest any method of providing an enrichment of semifluorinated alkane in the ophthalmic tissues or delayed ophthalmic release of semifluorinated alkane.

It is therefore an object of the present invention, to provide composition for use in an improved, and more efficient method for the treatment of keratoconjunctivitis sicca, and/or keratoconjunctivitis sicca due to Meibomian gland dysfunction and/or Meibomian gland dysfunction.

BRIEF SUMMARY

The present invention provides a novel method of providing delayed ophthalmic release of a semifluorinated alkane, for example, from an ophthalmic tissue enriched in the semifluorinated alkane due to treatment with an ophthalmic composition comprising the semifluorinated alkane, wherein the semifluorinated alkane is selected from the group consisting of $F(CF_2)_4(CH_2)_5H$, $F(CF_2)_4(CH_2)_6H$, $F(CF_2)_6(CH_2)_6H$, $F(CF_2)_6(CH_2)_8H$, and $F(CF_2)_8(CH_2)_8H$. In some embodiments, the composition comprises a single semifluorinated alkane, and is optionally free of any pharmaceutically active drug substance useful for ophthalmic treatment. In some embodiments, the composition consists of the single semifluorinated alkane. In some embodiments, the method comprises administering the composition to the eye of a patient in need thereof in an amount and/or frequency sufficient to enrich an ophthalmic tissue in the semifluorinated alkane. In some embodiments, said composition is administered less than four times per day, for example, three times per day, or two times per day or once per day, or less than once per day (e.g., on alternate days).

In another aspect, the present disclosure provides for an ophthalmic composition comprising a semifluorinated alkane for use in a method, and a method, of providing delayed ophthalmic release of a semifluorinated alkane, for example, from an ophthalmic tissue enriched in the semifluorinated alkane, the use comprising the topical administration of an ophthalmic composition comprising the semifluorinated alkane to the eye of a patient in need thereof, and the enrichment of an ophthalmic tissue with the semifluorinated alkane, wherein the semifluorinated alkane is selected from the group consisting of $F(CF_2)_4(CH_2)_5H$, $F(CF_2)_4(CH_2)_6H$, $F(CF_2)_6(CH_2)_6H$, $F(CF_2)_6(CH_2)_8H$, and $F(CF_2)_8(CH_2)_8H$.

In another aspect, the present disclosure provides for an ophthalmic composition comprising a semifluorinated alkane selected from the group consisting of $F(CF_2)_4(CH_2)_5H$, $F(CF_2)_4(CH_2)_6H$, $F(CF_2)_6(CH_2)_6H$, $F(CF_2)_6(CH_2)_8H$, and $F(CF_2)_8(CH_2)_8H$, for use in a method for the treatment of keratoconjunctivitis sicca (dry eye disease), and/or treating keratoconjunctivitis sicca (dry eye disease) due to Meibomian gland dysfunction and/or treating Meibomian gland dysfunction and/or for the treatment of a condition of the conjunctiva or cornea, wherein the method comprises a step of topically administering the composition to the eye of a patient in need thereof in a dose of a single drop per eye two times per day. In some embodiments, the ophthalmic composition for use consists of the semifluorinated alkane 1-perfluorohexyl-octane (F6H8).

In yet a further aspect, the present disclosure provides for a method for the treatment of keratoconjunctivitis sicca (dry eye disease), and/or treating keratoconjunctivitis sicca (dry eye disease) due to Meibomian gland dysfunction and/or treating Meibomian gland dysfunction and/or for the treatment of a condition of the conjunctiva or cornea, wherein the method comprises the step of topically administering an ophthalmic composition comprising a semifluorinated alkane selected from the group consisting of $F(CF_2)_4(CH_2)_5H$, $F(CF_2)_4(CH_2)_6H$, $F(CF_2)_6(CH_2)_6H$, $F(CF_2)_6(CH_2)_8H$, and $F(CF_2)_8(CH_2)_8H$, to the eye of a patient in need thereof in a dose of a single drop per eye two times per day. In some embodiments, the method comprises administering a composition consisting of the semifluorinated alkane 1-perfluorohexyl-octane (F6H8).

Further objects of the invention will become clear on the basis of the following description, examples, and patent claims.

DESCRIPTION OF THE DRAWINGS

FIG. 1(a) depicts change from baseline of the ocular surface damage of the total corneal region determined by fluorescein staining.

FIG. 1(b) depicts change from baseline of the ocular surface damage of the central corneal regions determined by fluorescein staining.

FIG. 1(c) depicts change from baseline of the ocular surface damage of the nasal corneal region determined by fluorescein staining.

FIG. 1(d) depicts change from baseline of the ocular surface damage of the temporal corneal region determined by fluorescein staining.

FIG. 2(a) depicts the change from baseline in respect of the VAS "severity of dryness".

FIG. 2(b) depicts the change from baseline visit in respect of the VAS parameter of "frequency of dryness".

FIG. 2(c) depicts the change from baseline visit in respect of the VAS parameter of "awareness of dryness".

FIG. 2(d) depicts the change from baseline visit in respect of the VAS parameter of "blurred vision".

FIG. 2(e) depicts the change observed from baseline visit in respect of the VAS parameter of "sensitivity to light".

Figure 1:
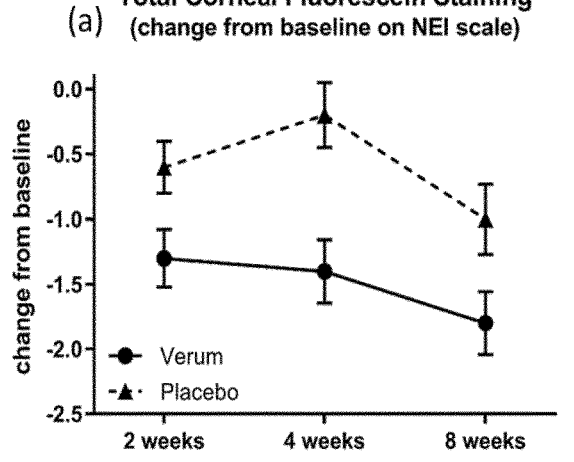
FIGS. 1(a) to 1(d). Ocular Surface Damage Assessment (Fluorescein Corneal Staining, NEI scale grading)—Depicted is the ocular surface damage of the cornea as the change from baseline (Visit 1, Day 1) for Visit 2 (2 weeks), Visit 3 (4 weeks) and Visit 4 (8 weeks), with *Verum* representing the 2-times daily treatment (BID) with NOV03 (ophthalmic composition essentially consisting of 1-perfluorohexyloctane; solid line) and placebo representing the saline solution (0.9% sodium chloride solution; QID+BID; dotted line).
Figure 1:
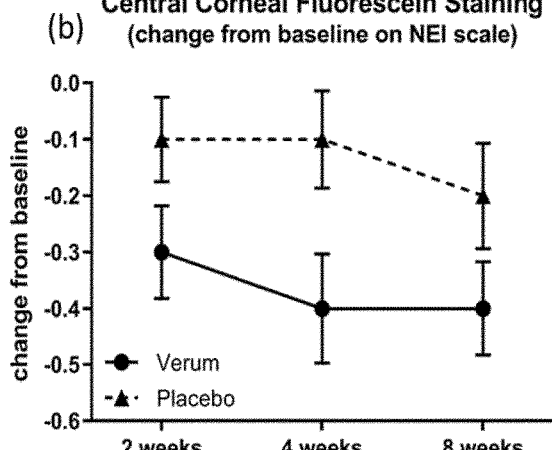
Figure 1:
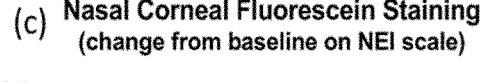
Figure 1:
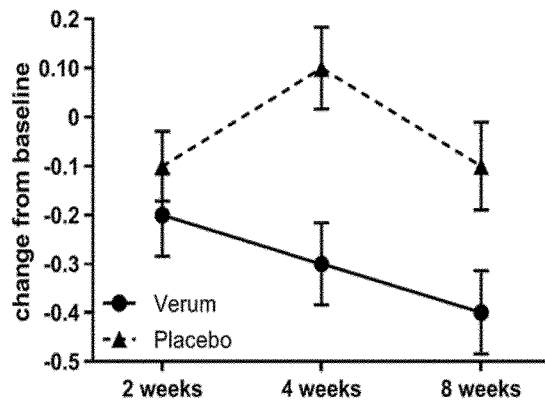
Figure 1:
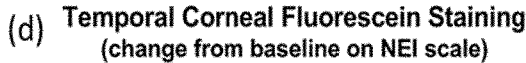
Figure 1:
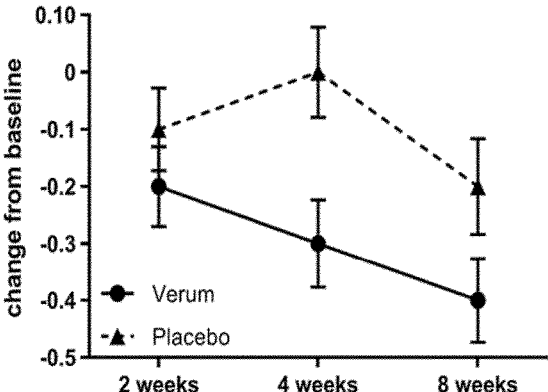
Figure 2:
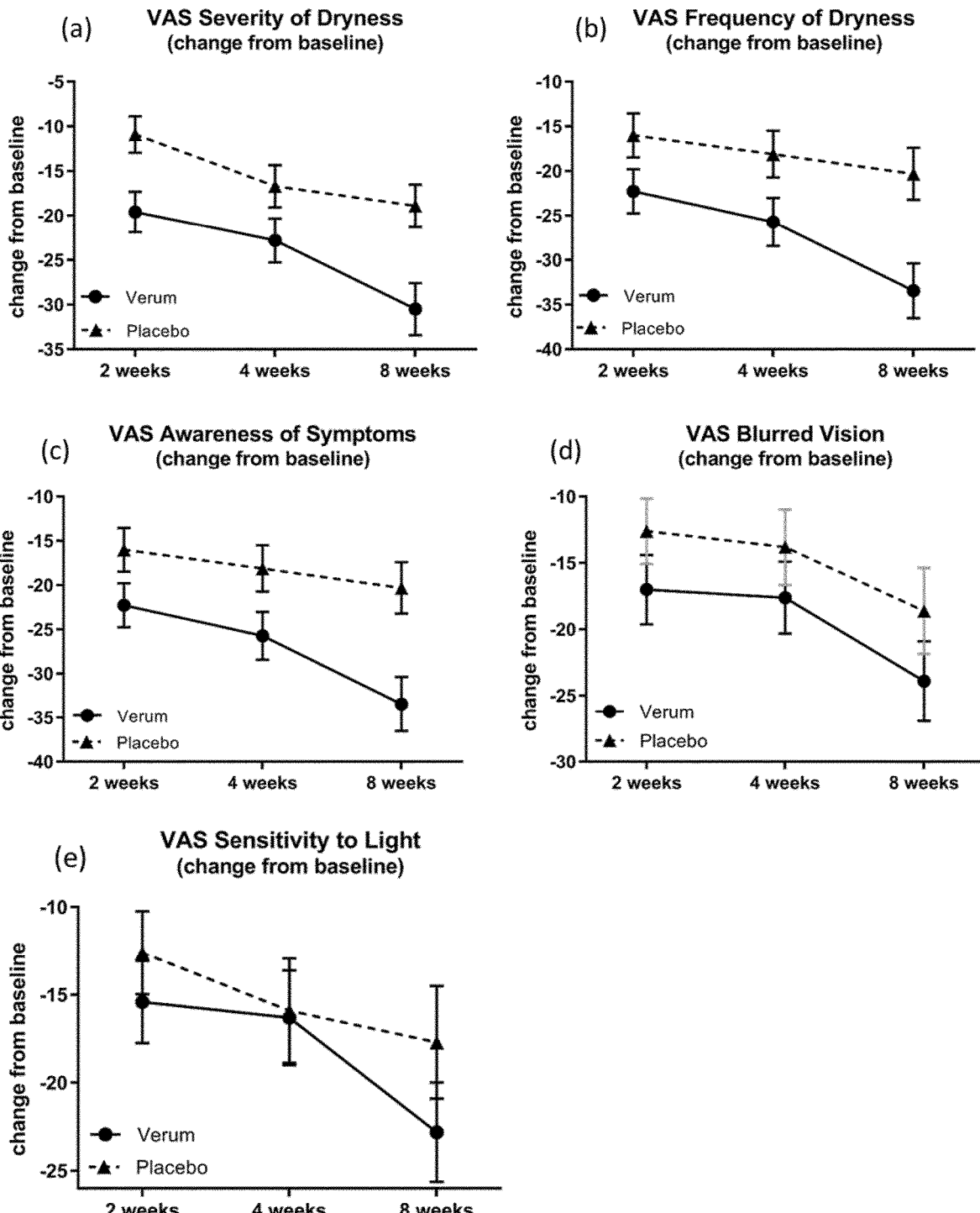
FIGS. 2(a) to 2(e). Symptom of dryness assessment determined by the Eye Dryness Score on a Visual Analog Scale (VAS). Depicted is the change from baseline (Visit 1, Day 1) for Visit 2 (2 weeks), Visit 3 (4 weeks) and Visit 4 (8 weeks), with *Verum* representing the 2-times daily treatment (BID) with NOV03 (ophthalmic composition essentially consisting of 1-perfluorohexyloctane; solid line) and Placebo representing the Saline solution (0.9% sodium chloride solution; QID+BID; dotted line).

Herein, the response to treatment is defined as a ≥25% improvement in the dryness symptom "severity of dryness". It was shown that within 2 weeks after start of the treatment already 50% of the patients in the NOV03-BID arm did show a response to treatment versus only 35% when treated with placebo.

DETAILED DESCRIPTION

In a first aspect, the present disclosure provides a method (Method 1) of providing delayed ophthalmic release of a semifluorinated alkane, for example, from an ophthalmic tissue enriched in the semifluorinated alkane due to treatment with an ophthalmic composition comprising the semifluorinated alkane, wherein the method comprises the step(s) of (a) administering to the eye of a patient in need thereof an amount of an ophthalmic composition comprising the semifluorinated alkane, optionally wherein the amount is effective to enrich an ophthalmic tissue in the semifluorinated alkane, and, optionally, (b) delayed release of the semifluorinated alkane from the enriched ophthalmic tissue; and wherein the semifluorinated alkane is selected from the group consisting of $F(CF_2)_4(CH_2)_5H$, $F(CF_2)_4(CH_2)_6H$, $F(CF_2)_6(CH_2)_6H$, $F(CF_2)_6(CH_2)_8H$, and $F(CF_2)_8(CH_2)_8H$. Further embodiments of the present disclosure provide as follows:

1.1 Method 1, wherein the semifluorinated alkane is selected from the group consisting of $F(CF_2)_4(CH_2)_5H$ and $F(CF_2)_6(CH_2)_8H$.

1.2 Method 1 or 1.1, wherein the semifluorinated alkane is $F(CF_2)_6(CH_2)_8H$.

1.3 Method 1 or any of 1.1 et seq., wherein the composition comprises the single semifluorinated alkane.

1.4 Method 1 or any of 1.1 et seq., wherein the composition is free of any pharmaceutically active drug substance useful for ophthalmic treatment.

1.5 Method 1 or any of 1.1 et seq., wherein the composition consists of the single semifluorinated alkane.

1.6 Method 1 or any of 1.1 to 1.2, wherein the compositions comprises at least one additional semifluorinated alkane.

1.7 Method 1.6, wherein the additional semifluorinated alkane has the formula $F(CF_2)_n(CH_2)_mH$, and wherein n is an integer from 4 to 8 and m is an integer from 5 to 10 and wherein the additional semifluorinated alkane is different from said first semifluorinated alkane.

1.8 Method 1.7, wherein the additional semifluorinated alkane is selected from the group consisting of $F(CF_2)_4(CH_2)_5H$, $F(CF_2)_4(CH_2)_6H$, $F(CF_2)_6(CH_2)_6H$, $F(CF_2)_6(CH_2)_8H$, $F(CF_2)_6(CH_2)_{10}H$, $F(CF_2)_8(CH_2)_8H$ and $F(CF_2)_8(CH_2)_{10}H$.

1.9 Method 1.6, 1.7 or 1.8, wherein the composition comprises the two semifluorinated alkanes.

1.10 Any of method 1.6-1.9, wherein the composition is free of any pharmaceutically active drug substance useful for ophthalmic treatment.

1.11 Any of method 1.6-1.10, wherein the composition consists of the two semifluorinated alkanes.

1.12 Method 1 or any of 1.1 et seq., wherein the ophthalmic composition is administered to the surface of the cornea and/or the conjunctiva in the form of liquid drops.

1.13 Method 1 or any of 1.1 et seq., wherein the patient suffers from keratoconjunctivitis sicca (dry eye disease), for example, the patient suffers from keratoconjunctivitis sicca (dry eye disease) due to Meibomian gland dysfunction.

1.14 Method 1.13, wherein the dry eye disease is aqueous-deficient dry eye disease.

1.15 Method 1.13 or 1.14, wherein the dry eye disease is evaporative dry eye disease.

1.16 Method 1 or any of 1.1 et seq., wherein the patient suffers from Meibomian gland dysfunction.

1.17 Method 1.16, wherein the patient is non-responsive to traditional physical methods of treating Meibomian gland dysfunction (MGD) (e.g., the methods discussed in Blackie et al., Review of Optometry, Jun. 21, 2012, pp. 1-12, which reference is incorporated by reference herein in its entirety).

1.18 Method 1 or any of 1.1 et seq., wherein the patient is non-responsive to treatment with aqueous ophthalmic eye drop compositions.

1.19 Method 1 or any of 1.1 et seq., wherein the composition is administered in a dose of a single drop per eye less than four times per day, for example, three times per day, or two times per day or once per day, or less than once per day (e.g., on alternate days).

1.20 Method 1.19, wherein the volume of each drop is 9-13 µL, e.g., 9-12 µL, or 10-13 µL, or 10-12 µL, or 10-11 µL, or about 11 µL.

1.21 Method 1 or any of 1.1 et seq., wherein the composition is administered in a dose of a single drop per eye three times per day in net volume of 30-33 µL.

1.22 Method 1 or any of 1.1 et seq., wherein the composition is administered in a dose of a single drop per eye two times per day in net volume of 20-22 µL.

1.23 Method 1 or any of 1.1 et seq., wherein the composition is administered in a dose of a single drop per eye one time per day in net volume of 10-11 µL.

1.24 Method 1 or any of 1.1 et seq., wherein the ophthalmic tissue enriched in the semifluorinated alkane is the palpebral conjunctiva, the cornea, the Meibomian glands, the lacrimal glands and/or the bulbar conjunctiva.

1.25 Method 1 or any of 1.1 et seq., wherein the ophthalmic tissue enriched in the semifluorinated alkane is the Meibomian glands, e.g., of the upper and/or lower eyelid.

1.26 Method 1 or any of 1.1 et seq., wherein the ophthalmic tissue enriched in the semifluorinated alkane releases all or substantially all of the semifluorinated alkane within 24 hours, optionally within 8 hours, of the last dose of the composition administered, optionally the enriched tissue releases at least 60% within 4 to 8 hours, or at least 80% within 8 hours, of the last dose of the composition administered.

1.27 Method 1 or any of 1.1 et seq., wherein, after sequential dosing of the composition (e.g., at least two doses administered within 24 hours), the ophthalmic tissue enriched in the semifluorinated alkane releases all or substantially all of the semifluorinated alkane within 24 hours, optionally within 8 hours, of the last dose administered, optionally the enriched tissue releases at least 50% within 4 to 8 hours, or at least 70% within 8 to 12 hours, of the last dose of the composition administered.

1.28 Method 1 or any of 1.1 et seq., wherein the ophthalmic tissue enriched in the semifluorinated alkane comprises about 0.00001 to 0.5 wt % of the semifluorinated alkane, optionally 0.0001 to 0.05 wt %, e.g., 0.0001 to 0.001 wt %, or 0.0004 to 0.0009 wt %, or 0.001 to 0.01 wt %, or 0.001 to 0.003 wt %, or 0.001 to 0.05%, or 0.005 to 0.03%, of the semifluorinated alkane.

1.29 Method 1 or any of 1.1 et seq., wherein the ophthalmic tissue enriched is the Meibomian glands, and the Meibomian glands comprise 0.0001 to 0.05 wt %, optionally 0.0005 to 0.05 wt %, or 0.001 to 0.03 wt % of the semifluorinated alkane.

1.30 Method 1 or any of 1.1 et seq., wherein treatment is performed for about at least 1 day, or for at least 5 days, or for at least 10 days, or for at least 30 days, or for at least 60, or for at least 90 days.

1.31 Method 1 or any of 1.1 et seq., wherein the method (a) increases the tear film thickness, (b) increases the lipid layer thickness, (c) supplements the tear film, (d) lubricates the ocular surface, (e) treats dry eye disease, (f) treats Meibomian Gland Dysfunction, or (g) treats a condition of the conjunctiva or cornea of a patient suffering from dry eye disease, or any combination thereof.

1.32 Method 1 or any of 1.1 et seq., wherein the method is effective to (a) increase the tear film thickness, (b) increase the lipid layer thickness, (c) supplements the tear film, (d) lubricate the ocular surface, (e) treat dry eye disease, (f) treat Meibomian Gland Dysfunction, or (g) treat a condition of the conjunctiva or cornea of a patient suffering from dry eye disease, or any combination thereof.

1.33 Method 1 or any of 1.1 et seq., wherein the patient is human patient.

1.34 Method 1 or any of 1.1 et seq., wherein the patient is an animal patient, e.g., a mammal, such as a dog, cat, rabbit and/or farm animal, such as a horse, pig, cow, or sheep.

1.35 Method 1.33, wherein the patient is a female patient.

1.36 Method 1.33, wherein the patient is a male patient.

1.37 Method 1.35 or 1.36, wherein the patient is aged 20-80 years old at the time of treatment, e.g., 20-50 years old, or 20-70 years old, or 30-80 years old, or 30-50 years old, or 30-70 years old, or 40-80 years old, or 40-60 years old, or 40-70 years old, or 50-80 years old, or 50-70 years old.

In further embodiments of the first aspect, the present disclosure further provides additional embodiments as follows:

1.38 Method 1, or any of 1.1 to 1.37 wherein the composition consists of 1-(perfluorohexyl)octane (F6H8).

1.39 Method 1, or any of 1.1 to 1.37, wherein the composition consists of a mixture of F6H8 and 2-(perfluorohexyl)octane.

1.40 Method 1.39, wherein the composition comprises the 2-(perfluorohexyl)octane in an amount of up to about 3 wt %, or up to about 2 wt %, or up to about 1 wt %.

1.41 Method 1, or any of 1.1-1.40, wherein the composition is administered two times per day per eye of a patient in a dose of a single drop of about 10-12 µl, or about 10-11 µl or about 11 µl.

1.42 Method 1 or any of 1.1-1.41, wherein the patient is characterized by at least 2 of the criteria selected from the group consisting of:
i. a tear film breakup time (TFBUT) of lower than 5 sec (e.g., lower than 3.8 sec),
ii. a total ocular surface disease index (OSDI) of higher than 25 (e.g., higher than 36),
iii. a total corneal fluorescein staining (NEI scale) between 4 and 11 (e.g., between 5 and 9),
iv. a Schirmer's Test I greater than 5 mm (e.g. equal to or higher than 10 mm, or equal to or higher than 15 mm), and
v. a MGD score of higher than 3 (e.g., higher than 4).

1.43 Method 1.42, wherein the patient has at least one eye which meets criteria (i), (iii), (iv), and (v).

1.44 Method 1, or any of 1.1-1.43, wherein the patient has a history of keratoconjunctivitis sicca (dry eye disease) in one or both eyes for at least six months.

1.45 Method 1, or any of 1.1-1.44, wherein the composition is effective in treating (reducing) simultaneously the ocular damage of one or more corneal regions and the symptoms of dryness in a patient suffering from keratoconjunctivitis sicca (dry eye disease) due to Meibomian gland dysfunction and/or Meibomian gland dysfunction.

1.46 Method 1.45, wherein the composition is effective in reducing said ocular damage and dryness symptoms within 2 weeks, within 4 weeks, or within 8 weeks after first administration of the composition.

1.47 Method 1.45 to 1.46, wherein the ocular surface damage of one or more corneal regions is selected from the group consisting of:
i. ocular surface damage of the total corneal region;
ii. ocular surface damage of the central corneal region;
iii. ocular surface damage of the nasal corneal region;
iv. ocular surface damage of the temporal corneal region; and
v. combinations thereof.

1.48 Method 1.45 to 1.47, wherein the reduction of ocular surface damage is determined by corneal fluorescein staining (NEI scale).

1.49 Method 1.48, wherein the damage of the ocular surface is determined by grading one or more of the corneal regions selected from the group consisting of the total corneal region, the central corneal region, the nasal corneal region and the temporal corneal region by fluorescein staining of the cornea.

1.50 Method 1, or any of 1.1-1.49, wherein the composition is effective in reducing one or more symptoms of dryness associated with keratoconjunctivitis sicca (dry eye disease) due to Meibomian gland dysfunction and/or Meibomian gland dysfunction.

1.51 Method 1.45-1.50, wherein the one or more symptoms of dryness are selected from the group consisting of:
  i. severity of dryness;
  ii. blurred vision;
  iii. sensitivity of light;
  iv. frequency of dryness;
  v. awareness of dryness; and
  vi. any combination thereof.

1.52 Method 1.51, wherein the symptoms (i) to (iii) are determined on a visual analog scale (VAS) from 0% to 100% indicating the level of discomfort of the patient and wherein the symptoms (iv) to (v) are determined on a visual analog scale (VAS) from 0% to 100% indicating the percentage of time said dryness symptoms are experienced by the patient.

1.53 Method 1.45 to 1.51, wherein the one or more symptoms are graded using a total ocular surface disease index (OSDI) score.

1.54 Method 1.53, wherein the total ocular surface disease index (OSDI) score is assessed on a scale of 1 to 100 with higher scores representing greater disability of the patient.

In further embodiments of the first aspect, the present disclosure further provides additional embodiments as follows:

1.55 Method 1, or any of 1.1 to 1.54, wherein the composition consists of F6H8 (1-(perfluorohexyl)octane).

1.56 Method 1.55, wherein the delayed ophthalmic release is from an anterior segment tissues selected from the group consisting of: meibomian glands, conjunctiva (bulbar), conjunctiva (palpebral), cornea, sclera (anterior), lacrimal gland (accessory), lacrimal gland (main), and tears (e.g., tear film).

1.57 Method 1.56, wherein the method provides a maximal concentration of the semifluorinated alkane (e.g., F6H8) of at least 2000 ng per gram of tissue in an anterior segment tissue of the eye, optionally, wherein said concentration is provided by a single drop dose of 40-60 mg of the semifluorinated alkane (e.g., F6H8) administered either once per day or twice per day.

1.58 Method 1.56, wherein the method provides a maximal concentration of the semifluorinated alkane (e.g., F6H8) of at least 2270 ng per gram of tissue in an anterior segment tissue of the eye, optionally, wherein said concentration is provided by a single drop dose of 40-60 mg of the semifluorinated alkane (e.g., F6H8) administered either once per day or twice per day.

1.59 Method 1.57 or 1.58, wherein said concentration is provided by a single drop dose of about 50 mg of the semifluorinated alkane (e.g., F6H8), for example about 47 mg administered either once per day or twice per day.

1.60 Any of Methods 1.57 to 1.59, wherein said anterior segment tissue of the eye reaching said maximal concentration of the semifluorinated alkane (e.g., F6H8), is selected from the group consisting of meibomian glands, conjunctiva (bulbar), conjunctiva (palpebral), cornea, sclera (anterior), and tears.

1.61 Method 1.60, wherein said maximal concentration of semifluorinated alkane (e.g., F6H8) is reached within 0.25 to 2 hours (e.g., 0.25 to 1 hours, or 0.25 to 0.5 hours) after a single drop dose of the composition is administered either once per day or twice per day.

1.62 Any of Method 1.56 to 1.61, wherein said anterior segment tissue of the eye reaching said maximal concentration of the semifluorinated alkane (e.g., F6H8), is selected from the group consisting of lacrimal gland (accessory) and lacrimal gland (main).

1.63 Method 1.62, wherein said maximal concentration of semifluorinated alkane (e.g., F6H8) is reached within 3 to 5 hours (e.g., 4 hours) after a single drop dose of the composition is administered either once per day or twice per day.

1.64 Any of Methods 1.56 to 1.63, wherein the method provides a maximal concentration of the semifluorinated alkane (e.g., F6H8) of at least:
  a. 222,000 ng/g of tissue in the Meibomian glands;
  b. 5450 ng/g of tissue in the conjunctiva (bulbar);
  c. 14,000 ng/g of tissue in the conjunctive (palpebral);
  d. 8230 ng/g of tissue in the cornea;
  e. 2270 ng/g of tissue in the sclera (anterior);
  f. 4280 ng/g of tissue in the lacrimal gland (accessory);
  g. 4130 ng/g of tissue in the lacrimal gland (main); and/or
  h. 1300 ng/g of tears;
  after a single drop dose of the composition administered either once or twice per day.

1.65 Method 1.64, wherein the method provides a maximal concentration of the semifluorinated alkane (e.g., F6H8) of at least 5000 ng/g of tears, e.g., at least 10,000 ng/g, or at least 50,000 ng/g, or at least 100,000 ng/g, or at least 500,000 ng/g, or at least 1,000,000 ng/g, or at least 2,000,000 ng/g, up to about 2,330,000 ng/g of tears.

In a second aspect, the present disclosure provides a method (Method 2) of increasing tear film thickness and/or increasing the lipid layer thickness and/or supplementing the tear film and/or lubricating the ocular surface, wherein the method comprises the step(s) of (a) administering to the eye of a patient in need thereof an amount of an ophthalmic composition comprising a semifluorinated alkane, selected from the group consisting of $F(CF_2)_4(CH_2)_5H$, $F(CF_2)_4(CH_2)_6H$, $F(CF_2)_6(CH_2)$ 6H, $F(CF_2)_6(CH_2)_8H$, and $F(CF_2)_8(CH_2)_8H$, optionally wherein the amount is effective to enrich an ophthalmic tissue in the semifluorinated alkane, and, optionally, (b) delayed release of the semifluorinated alkane from the enriched ophthalmic tissue. Further embodiments of the present disclosure provide as follows:

2.1 Method 2, wherein the semifluorinated alkane is selected from the group consisting of $F(CF_2)_4(CH_2)_5H$ and $F(CF_2)_6(CH_2)_8H$.

2.2 Method 2 or 2.1, wherein the semifluorinated alkane is $F(CF_2)_6(CH_2)_8H$.

2.3 Method 2 or any of 2.1 et seq., wherein the composition comprises the single semifluorinated alkane.

2.4 Method 2 or any of 2.1 et seq., wherein the composition is free of any pharmaceutically active drug substance useful for ophthalmic treatment.

2.5 Method 2 or any of 2.1 et seq., wherein the composition consists of the single semifluorinated alkane.

2.6 Method 2 or any of 2.1 to 2.2, wherein the compositions comprises at least one additional semifluorinated alkane.

2.7 Method 2.6, wherein the additional semifluorinated alkane has the formula $F(CF_2)_n(CH_2)_mH$, and wherein n is an integer from 4 to 8 and m is an integer from 5 to 10 and wherein the additional semifluorinated alkane is different from said first semifluorinated alkane.

2.8 Method 2.7, wherein the additional semifluorinated alkane is selected from the group consisting of $F(CF_2)$ $_4(CH_2)_5H$, $F(CF_2)_4(CH_2)_6H$, $F(CF_2)_6(CH_2)_6H$, $F(CF_2)_6(CH_2)_8H$, $F(CF_2)_6(CH_2)_{10}H$, $F(CF_2)_8(CH_2)_8H$ and $F(CF_2):(CH_2)_{10}H$.

2.9 Method 2.6, 2.7 or 2.8, wherein the composition comprises the two semifluorinated alkanes.

2.10 Any of method 2.6 to 2.9, wherein the composition is free of any pharmaceutically active drug substance useful for ophthalmic treatment.

2.11 Any of method 2.6 to 2.10, wherein the composition consists of the two semifluorinated alkanes.

2.12 Method 2 or any of 2.1 et seq., wherein the ophthalmic composition is administered to the surface of the cornea and/or the conjunctiva in the form of liquid drops.

2.13 Method 2 or any of 2.1 et seq., wherein the patient suffers from keratoconjunctivitis sicca (dry eye disease), optionally the patient suffers from keratoconjunctivitis sicca (dry eye disease) due to Meibomian gland dysfunction.

2.14 Method 2.13, wherein the dry eye disease is aqueous-deficient dry eye disease.

2.15 Method 2.13 or 2.14, wherein the dry eye disease is evaporative dry eye disease.

2.16 Method 2 or any of 2.1 et seq., wherein the patient suffers from Meibomian gland dysfunction.

2.17 Method 2.16, wherein the patient is non-responsive to traditional physical methods of treating Meibomian Gland Dysfunction MGD (e.g., the methods discussed in Blackie et al., Review of Optometry, Jun. 21, 2012, pp. 1-12, which reference is incorporated by reference herein in its entirety).

2.18 Method 2 or any of 2.1 et seq., wherein the patient is non-responsive to treatment with aqueous ophthalmic eye drop compositions.

2.19 Method 2 or any of 2.1 et seq., wherein the composition is administered in a dose of a single drop per eye less than four times per day, for example, three times per day, or two times per day or once per day, or less than once per day (e.g., on alternate days).

2.20 Method 2.19, wherein the volume of each drop is 9-13 μL, e.g., 9-12 μL, or 10-13 μL, or 10-12 μL, or 10-11 μL, or about 11 μL.

2.21 Method 2 or any of 2.1 et seq., wherein the composition is administered in a dose of a single drop per eye three times per day in net volume of 30-33 μL.

2.22 Method 2 or any of 2.1 et seq., wherein the composition is administered in a dose of a single drop per eye two times per day in net volume of 20-22 μL. 2.23 Method 2 or any of 2.1 et seq., wherein the composition is administered in a dose of a single drop per eye one time per day in net volume of 10-11 μL.

2.24 Method 2 or any of 2.1 et seq., wherein the ophthalmic tissue enriched in the semifluorinated alkane is the palpebral conjunctiva, the cornea, the Meibomian glands, the lacrimal glands and/or the bulbar conjunctiva.

2.25 Method 2 or any of 2.1 et seq., wherein the ophthalmic tissue enriched in the semifluorinated alkane is the Meibomian glands, e.g., of the upper and/or lower eyelid.

2.26 Method 2 or any of 2.1 et seq., wherein the ophthalmic tissue enriched in the semifluorinated alkane releases all or substantially all of the semifluorinated alkane within 24 hours, optionally within 8 hours, of the last dose of the composition administered, optionally the enriched tissue releases at least 60% within 4 to 8 hours, or at least 80% within 8 hours, of the last dose of the composition administered.

2.27 Method 2 or any of 2.1 et seq., wherein, after sequential dosing of the composition (e.g., at least two doses administered within 24 hours), the ophthalmic tissue enriched in the semifluorinated alkane releases all or substantially all of the semifluorinated alkane within 24 hours, optionally within 8 hours, of the last dose administered, optionally the enriched tissue releases at least 50% within 4 to 8 hours, or at least 70% within 8 to 12 hours, of the last dose of the composition administered.

2.28 Method 2 or any of 2.1 et seq., wherein the ophthalmic tissue enriched in the semifluorinated alkane comprises about 0.00001 to 0.5 wt % of the semifluorinated alkane, optionally 0.0001 to 0.05 wt %, e.g., 0.0001 to 0.001 wt %, or 0.0004 to 0.0009 wt %, or 0.001 to 0.01 wt %, or 0.001 to 0.003 wt %, or 0.001 to 0.05%, or 0.005 to 0.03% of the semifluorinated alkane.

2.29 Method 2 or any of 2.1 et seq., wherein the ophthalmic tissue enriched is the Meibomian glands, and the Meibomian glands comprise 0.0001 to 0.05 wt %, optionally 0.0005 to 0.05 wt %, or 0.001 to 0.03 wt % of the semifluorinated alkane.

2.30 Method 2 or any of 2.1 et seq., wherein treatment is performed for about at least 1 day, or for at least 5 days, or for at least 10 days, or for at least 30 days, or for at least 60, or for at least 90 days (e.g. consecutive days).

2.31 Method 2 or any of 2.1 et seq., wherein the patient is human patient.

2.32 Method 2 or any of 2.1 et seq., wherein the patient is an animal patient, e.g., a mammal, such as, a dog, cat, rabbit and/or farm animal, such as a horse, pig, cow, or sheep.

2.33 Method 2.31, wherein the patient is a female patient.

2.34 Method 2.31, wherein the patient is a male patient.

2.35 Method 2.33 or 2.34, wherein the patient is aged 20-80 years old at the time of treatment, e.g., 20-50 years old, or 20-70 years old, or 30-80 years old, or 30-50 years old, or 30-70 years old, or 40-80 years old, or 40-60 years old, or 40-70 years old, or 50-80 years old, or 50-70 years old.

In further embodiments of the second aspect, the present disclosure further provides additional embodiments as follows:

2.36 Method 2, or any of 2.1 to 2.35 wherein the composition consists of 1-(perfluorohexyl)octane (F6H8).

2.37 Method 2, or any of 2.1 to 2.35, wherein the composition consists of a mixture of F6H8 and 2-(perfluorohexyl)octane.

2.38 Method 2.37, wherein the composition comprises the 2-(perfluorohexyl)octane in an amount of up to about 3 wt %, or up to about 2 wt %, or up to about 1 wt %.

2.39 Method 2, or any of 2.1-2.38, wherein the composition is administered two times per day per eye of a patient in a dose of a single drop of about 10-12 μl, or about 10-11 μl or about 11 μl.

2.40 Method 2 or any of 2.1-2.39, wherein the patient has a highly symptomatic ocular condition, for example, characterized by meeting at least 2 of the criteria selected from the group consisting of:

i. a tear film breakup time (TFBUT) of lower than 5 sec (e.g., lower than 3.8 sec), ii. a total ocular surface disease index (OSDI) of higher than 25 (e.g., higher than 40), iii. a total corneal fluorescein staining (NEI scale) between 4 and 11 (e.g., between 5 and 9), iv. a Schirmer's Test I greater than 5 mm (e.g. equal to or higher than 10 mm, or equal to or higher than 15 mm), and v. a MGD score of higher than 3 (e.g., higher than 4).

2.41 Method 2.40, wherein the patient has at least one eye which meets criteria (i), (iii), (iv), and (v).

2.42 Method 2, or any of 2.1-2.41, wherein the patient has a history of keratoconjunctivitis sicca (dry eye disease) in one or both eyes for at least six months.

2.43 Method 2, or any of 2.1-2.42, wherein the composition is effective in treating (reducing) simultaneously the ocular damage of one or more corneal regions and the symptoms of dryness in a patient suffering from keratoconjunctivitis sicca (dry eye disease) due to Meibomian gland dysfunction and/or Meibomian gland dysfunction.

2.44 Method 2.43, wherein the composition is effective in reducing said ocular surface damage and symptoms of dryness within 2 weeks, or within 4 weeks, or 8 weeks after first administration of the composition.

2.45 Method 2, or any of 2.1-2.44, wherein the composition is effective in reducing ocular damage of one or more corneal regions and the symptoms of dryness within 2 weeks, preferably within 4 weeks, more preferably or within 8 weeks after first administration of the composition.

2.46 Method 2.43 to 2.45, wherein the ocular surface damage is selected from the group consisting of:

i. ocular surface damage of the total corneal region;

ii. ocular surface damage of the central corneal region;

iii. ocular surface damage of the nasal corneal region;

iv. ocular surface damage of the temporal corneal region; and v. combinations thereof.

2.47 Method 2.43 to 2.46, wherein the reduction of ocular surface damage is determined by corneal fluorescein staining (NEI scale).

2.48 Method 2.47, wherein the damage of the ocular surface is determined by grading one or more of the corneal regions selected from the group consisting of the total corneal region, the central corneal region, the nasal corneal region and the temporal corneal region by fluorescein staining of the cornea.

2.49 Method 2, or any of 2.1-2.48, wherein the composition is effective in reducing one or more symptoms of dryness associated with keratoconjunctivitis sicca (dry eye disease) due to Meibomian gland dysfunction and/or Meibomian gland dysfunction.

2.50 Method 2.43-2.49, wherein the one or more symptoms of dryness are selected from the group consisting of:

i. severity of dryness;

ii. blurred vision;

iii. sensitivity of light;

iv. frequency of dryness;

v. awareness of dryness; and vi. any combination thereof.

2.51 Method 2.50, wherein the symptoms (i) to (iii) are determined on a visual analog scale (VAS) from 0% to 100% indicating the level of discomfort of the patient and wherein the symptoms (iv) to (v) are determined on a visual analog scale (VAS) from 0% to 100% indicating the percentage of time said dryness symptoms are experienced by the patient.

2.52 Method 2.43 to 2.50, wherein the one or more symptoms of dryness are graded using the total ocular surface disease index (OSDI) score.

2.53 Method 2.52, wherein the total ocular surface disease index (OSDI) score is assessed on a scale of 1 to 100 with higher scores representing greater disability of the patient.

In further embodiments of the second aspect, the present disclosure further provides additional embodiments as follows:

2.54 Method 2, or any of 2.1 to 2.53, wherein the composition consists of F6H8 (1-(perfluorohexyl)octane).

2.55 Method 2.54, wherein the delayed ophthalmic release is from an anterior segment tissues selected from the group consisting of: meibomian glands, conjunctiva (bulbar), conjunctiva (palpebral), cornea, sclera (anterior), lacrimal gland (accessory), lacrimal gland (main), and tears (e.g., tear film).

2.56 Method 2.55, wherein the method provides a maximal concentration of the semifluorinated alkane (e.g., F6H8) of at least 2000 ng per gram of tissue in an anterior segment tissue of the eye, optionally, wherein said concentration is provided by a single drop dose of 40-60 mg of the semifluorinated alkane (e.g., F6H8) administered either once per day or twice per day.

2.57 Method 2.55, wherein the method provides a maximal concentration of the semifluorinated alkane (e.g., F6H8) of at least 2270 ng per gram of tissue in an anterior segment tissue of the eye, optionally, wherein said concentration is provided by a single drop dose of 40-60 mg of the semifluorinated alkane (e.g., F6H8) administered either once per day or twice per day.

2.58 Method 2.56 or 2.57, wherein said concentration is provided by a single drop dose of about 50 mg of the semifluorinated alkane (e.g., F6H8), for example about 47 mg administered either once per day or twice per day.

2.59 Any of Methods 2.55 to 2.58, wherein said anterior segment tissue of the eye reaching said maximal concentration of the semifluorinated alkane (e.g., F6H8), is selected from the group consisting of meibomian glands, conjunctiva (bulbar), conjunctiva (palpebral), cornea, sclera (anterior), and tears.

2.60 Method 2.59, wherein said maximal concentration of semifluorinated alkane (e.g., F6H8) is reached within 0.25 to 2 hours (e.g., 0.25 to 1 hours, or 0.25 to 0.5 hours) after a single drop dose of the composition is administered either once per day or twice per day.

2.61 Any of Method 2.55 to 2.60, wherein said anterior segment tissue of the eye reaching said maximal concentration of the semifluorinated alkane (e.g., F6H8), is selected from the group consisting of lacrimal gland (accessory) and lacrimal gland (main).

2.62 Method 2.61, wherein said maximal concentration of semifluorinated alkane (e.g., F6H8) is reached within 3 to 5 hours (e.g., 4 hours) after a single drop dose of the composition is administered either once per day or twice per day.

2.63 Any of Methods 2.55 to 2.62, wherein the method provides a maximal concentration of the semifluorinated alkane (e.g., F6H8) of at least:

a. 222,000 ng/g of tissue in the Meibomian glands;

b. 5450 ng/g of tissue in the conjunctiva (bulbar);

c. 14,000 ng/g of tissue in the conjunctive (palpebral);

d. 8230 ng/g of tissue in the cornea;

e. 2270 ng/g of tissue in the sclera (anterior);

f. 4280 ng/g of tissue in the lacrimal gland (accessory);

g. 4130 ng/g of tissue in the lacrimal gland (main); and/or h. 1300 ng/g of tears;

after a single drop dose of the composition administered either once or twice per day.

2.64 Method 2.63, wherein the method provides a maximal concentration of the semifluorinated alkane (e.g., F6H8) of at least 5000 ng/g of tears, e.g., at least 10,000 ng/g, or at least 50,000 ng/g, or at least 100,000 ng/g, or at least 500,000 ng/g, or at least 1,000,000 ng/g, or at least 2,000,000 ng/g, up to about 2,330,000 ng/g of tears.

In a third aspect, the present disclosure provides a method (Method 3) of treating dry eye disease and/or treating keratoconjunctivitis sicca (dry eye disease) due to Meibomian gland dysfunction and/or treating Meibomian gland dysfunction and/or treating a condition of the conjunctiva or cornea, wherein the method comprises the step(s) of (a) administering to the eye of a patient in need thereof an amount of an ophthalmic composition comprising the semifluorinated alkane, optionally wherein the amount is effective to enrich an ophthalmic tissue in the semifluorinated alkane, and, optionally, (b) delayed release of the semifluorinated alkane from the enriched ophthalmic tissue, and wherein the semifluorinated alkane is selected from the group consisting of $F(CF_2)_4(CH_2)_5H$, $F(CF_2)_4(CH_2)_6H$, $F(CF_2)_6(CH_2)_6H$, $F(CF_2)_6(CH_2)_8H$, and $F(CF_2)_8(CH_2)_8H$. Further embodiments of the present disclosure provide as follows:

3.1 Method 3, wherein the semifluorinated alkane is selected from the group consisting of $F(CF_2)_4(CH_2)_5H$ and $F(CF_2)_6(CH_2)_8H$.

3.2 Method 3 or any of 3.1, wherein the semifluorinated alkane is $F(CF_2)_6(CH_2)_8H$.

3.3 Method 3 or any of 3.1 et seq., wherein the composition comprises the single semifluorinated alkane.

3.4 Method 3 or any of 3.1 et seq., wherein the composition is free of any pharmaceutically active drug substance useful for ophthalmic treatment.

3.5 Method 3 or any of 3.1 et seq., wherein the composition consists of the single semifluorinated alkane.

3.6 Method 3 or any of 3.1 et seq., wherein the compositions comprises at least one additional semifluorinated alkane.

3.7 Method 3.6, wherein the additional semifluorinated alkane has the formula $F(CF_2)_n(CH_2)_mH$, and wherein n is an integer from 4 to 8 and m is an integer from 5 to 10 and wherein the additional semifluorinated alkane is different from said first semifluorinated alkane.

3.8 Method 3.7, wherein the additional semifluorinated alkane is selected from the group consisting of $F(CF_2)_4(CH_2)_5H$, $F(CF_2)_4(CH_2)_6H$, $F(CF_2)_6(CH_2)_6H$, $F(CF_2)_6(CH_2)_8H$, $F(CF_2)_6(CH_2)_{10}H$, $F(CF_2)_8(CH_2)_8H$ and $F(CF_2)_8(CH_2)_{10}H$.

3.9 Method 3.6, 3.7 or 3.8, wherein the composition comprises the two semifluorinated alkanes.

3.10 Any of method 3.6 to 3.9, wherein the composition is free of any pharmaceutically active drug substance useful for ophthalmic treatment.

3.11 Any of method 3.6 to 3.10, wherein the composition consists of the two semifluorinated alkanes.

3.12 Method 3 or any of 3.1 et seq., wherein the ophthalmic composition is administered to the surface of the cornea and/or the conjunctiva in the form of liquid drops.

3.13 Method 3 or any of 3.1 et seq., wherein the patient suffers from keratoconjunctivitis sicca (dry eye disease), optionally the patient suffers from keratoconjunctivitis sicca (dry eye disease) due to Meibomian gland dysfunction.

3.14 Method 3.13, wherein the dry eye disease is aqueous-deficient dry eye disease.

3.15 Method 3.13 or 3.14, wherein the dry eye disease is evaporative dry eye disease.

3.16 Method 3 or any of 3.1 et seq., wherein the patient suffers from Meibomian gland dysfunction.

3.17 Method 3.16, wherein the patient is non-responsive to traditional physical methods of treating Meibomian Gland Dysfunction (MGD) (e.g., the methods discussed in Blackie et al., Review of Optometry, Jun. 21, 2012, pp. 1-12, which reference is incorporated by reference herein in its entirety).

3.18 Method 3 or any of 3.1 et seq., wherein the patient is non-responsive to treatment with aqueous ophthalmic eye drop compositions.

3.19 Method 3 or any of 3.1 et seq., wherein the composition is administered in a dose of a single drop per eye less than four times per day, for example, three times per day, or two times per day or once per day, or less than once per day (e.g., on alternate days).

3.20 Method 3.19, wherein the volume of each drop is 9-13 µL, e.g., 9-12 µL, or 10-13 µL, or 10-12 µL, or 10-11 µL, or about 11 µL.

3.21 Method 3 or any of 3.1 et seq., wherein the composition is administered in a dose of a single drop per eye three times per day in net volume of 30-33 µL.

3.22 Method 3 or any of 3.1 et seq., wherein the composition is administered in a dose of a single drop per eye two times per day in net volume of 20-22 µL.

3.23 Method 3 or any of 3.1 et seq., wherein the composition is administered in a dose of a single drop per eye one times per day in net volume of 10-11 µL.

3.24 Method 3 or any of 3.1 et seq., wherein the ophthalmic tissue enriched in the semifluorinated alkane is the palpebral conjunctiva, the cornea, the Meibomian glands, the lacrimal glands and/or the bulbar conjunctiva.

3.25 Method 3 or any of 3.1 et seq., wherein the ophthalmic tissue enriched in the semifluorinated alkane is the Meibomian glands, e.g., of the upper and/or lower eyelid.

3.26 Method 3 or any of 3.1 et seq., wherein the ophthalmic tissue enriched in the semifluorinated alkane releases all or substantially all of the semifluorinated alkane within 24 hours, optionally within 8 hours, of the last dose of the composition administered, optionally the enriched tissue releases at least 60% within 4 to 8 hours, or at least 80% within 8 hours, of the last dose of the composition administered.

3.27 Method 3 or any of 3.1 et seq., wherein, after sequential dosing of the composition (e.g., at least two doses administered within 24 hours), the ophthalmic tissue enriched in the semifluorinated alkane releases all or substantially all of the semifluorinated alkane within 24 hours, optionally within 8 hours, of the last dose administered, optionally the enriched tissue releases at least 50% within 4 to 8 hours, or at least 70% within 8 to 12 hours, of the last dose of the composition administered.

3.28 Method 3 or any of 3.1 et seq., wherein the ophthalmic tissue enriched in the semifluorinated alkane comprises about 0.00001 to 0.5 wt % of the semifluorinated alkane, optionally 0.0001 to 0.05 wt %, e.g., 0.0001 to 0.001 wt %, or 0.0004 to 0.0009 wt %, or 0.001 to 0.01 wt %, or 0.001 to 0.003 wt %, or 0.001 to 0.05%, or 0.005 to 0.03%, of the semifluorinated alkane.

3.29 Method 3 or any of 3.1 et seq., wherein the ophthalmic tissue enriched is the Meibomian glands, and the Meibomian glands comprise 0.0001 to 0.05 wt %, optionally 0.0005 to 0.05 wt %, or 0.001 to 0.03 wt % of the semifluorinated alkane.

3.30 Method 3 or any of 3.1 et seq., wherein treatment is performed for about at least 1 day, or for at least 5 days, or for at least 10 days, or for at least 30 days, or for at least 60, or for at least 90 days, e.g. consecutive days.

3.31 Method 3 or any of 3.1 et seq., wherein the patient is human patient.

3.32 Method 3 or any of 3.1 et seq., wherein the patient is an animal patient, e.g., a mammal, such as, a dog, cat, rabbit and/or farm animal, such as a horse, pig, cow, or sheep.

3.33 Method 3.31, wherein the patient is a female patient.

3.34 Method 3.31, wherein the patient is a male patient.

3.35 Method 3.33 or 3.34, wherein the patient is aged 20-80 years old at the time of treatment, e.g., 20-50 years old, or 20-70 years old, or 30-80 years old, or 30-50 years old, or 30-70 years old, or 40-80 years old, or 40-60 years old, or 40-70 years old, or 50-80 years old, or 50-70 years old.

In further embodiments of the third aspect, the present disclosure further provides additional embodiments as follows:

3.36 Method 3, or any of 3.1 to 3.35 wherein the composition consists of 1-(perfluorohexyl)octane (F6H8).

3.37 Method 3, or any of 3.1 to 3.35, wherein the composition consists of a mixture of F6H8 and to 2-(perfluorohexyl)octane.

3.38 Method 3.37, wherein the composition comprises the 2-(perfluorohexyl)octane in an amount of up to about 3 wt %, or up to about 2 wt %, or up to about 1 wt %.

3.39 Method 3, or any of 3.1-3.38, wherein the composition is administered two times per day per eye of a patient in a dose of a single drop of about 10-12 µl, or about 10-11 µl or about 11 µl.

3.40 Method 3 or any of 3.1-3.39, wherein the patient has a highly symptomatic ocular condition, for example, characterized by meeting at least 2 of the criteria selected from the group consisting of:
i. a tear film breakup time (TFBUT) of lower than 5 sec (e.g., lower than 3.8 sec),
ii. a total ocular surface disease index (OSDI) of higher than 25 (e.g., higher than 40),
iii. a total corneal fluorescein staining (NEI scale) between 4 and 11 (e.g., between 5 and 9),
iv. a Schirmer's Test I greater than 5 mm (e.g. equal to or higher than 10 mm, or equal to or higher than 15 mm), and
v. a MGD score of higher than 3 (e.g., higher than 4).

3.41 Method 3.40, wherein the patient has at least one eye which meets criteria (i), (iii), (iv), and (v).

3.42 Method 3, or any of 3.1-3.41, wherein the patient has a history of keratoconjunctivitis sicca (dry eye disease) in one or both eyes for at least six months.

3.43 Method 3, or any of 3.1-3.42, wherein the composition is effective in reducing the ocular surface damage and one or more symptoms dryness in a patient suffering from keratoconjunctivitis sicca (dry eye disease) due to Meibomian gland dysfunction and/or Meibomian gland dysfunction.

3.44 Method 3.43, wherein the composition is effective in reducing said ocular surface damage and one or more symptoms of dryness within 2 weeks, within 4 weeks, or within 8 weeks after first administration of the composition.

3.45 Method 3.44, wherein the ocular surface damage of one or more corneal regions is selected from the group consisting of:
i. ocular surface damage of the total corneal region;
ii. ocular surface damage of the central corneal region;
iii. ocular surface damage of the nasal corneal region;
iv. ocular surface damage of the temporal corneal region; and
v. combinations thereof.

3.46 Method 3.43 to 3.45, wherein the reduction of ocular surface damage is determined by corneal fluorescein staining (NEI scale).

3.47 Method 3.46, wherein the damage of the ocular surface is determined by grading one or more of the corneal regions selected from the group consisting of the total corneal region, the central corneal region, the nasal corneal region and the temporal corneal region by fluorescein staining of the cornea.

3.48 Method 3, or any of 3.1-3.47, wherein the composition is effective in reducing one or more symptoms of dryness associated with keratoconjunctivitis sicca (dry eye disease) due to Meibomian gland dysfunction and/or Meibomian gland dysfunction.

3.49 Method 3.43 to 3.48, wherein the one or more symptoms of dryness are selected from the group consisting of:
i. severity of dryness;
ii. blurred vision;
iii. sensitivity of light;
iv. frequency of dryness;
v. awareness of dryness; and
vi. any combination thereof.

3.50 Method 3.49, wherein the symptoms (i) to (iii) are determined on a visual analog scale (VAS) from 0% to 100% indicating the level of discomfort of the patient and wherein the symptoms (iv) to (v) are determined on a visual analog scale (VAS) from 0% to 100% indicating the percentage of time said dryness symptoms are experienced by the patient.

3.51 Method 3.57, wherein the one or more symptoms of dryness are graded using the total ocular surface disease index (OSDI) score.

3.52 Method 3.51, wherein the total ocular surface disease index (OSDI) score is assessed on a scale of 1 to 100 with higher scores representing greater disability of the patient.

In further embodiments of the third aspect, the present disclosure further provides additional embodiments as follows:

3.53 Method 3, or any of 3.1 to 3.52, wherein the composition consists of F6H8 (1-(perfluorohexyl)octane).

3.54 Method 3.53, wherein the delayed ophthalmic release is from an anterior segment tissues selected from the group consisting of: meibomian glands, conjunctiva (bulbar), conjunctiva (palpebral), cornea, sclera (anterior), lacrimal gland (accessory), lacrimal gland (main), and tears (e.g., tear film).

3.55 Method 3.54, wherein the method provides a maximal concentration of the semifluorinated alkane (e.g., F6H8) of at least 2000 ng per gram of tissue in an anterior segment tissue of the eye, optionally, wherein said concentration is provided by a single drop dose of 40-60 mg of the semifluorinated alkane (e.g., F6H8) administered either once per day or twice per day.

3.56 Method 3.54, wherein the method provides a maximal concentration of the semifluorinated alkane (e.g., F6H8) of at least 2270 ng per gram of tissue in an anterior segment tissue of the eye, optionally, wherein said concentration is provided by a single drop dose of 40-60 mg of the semifluorinated alkane (e.g., F6H8) administered either once per day or twice per day.

3.57 Method 3.55 or 3.56, wherein said concentration is provided by a single drop dose of about 50 mg of the semifluorinated alkane (e.g., F6H8), for example about 47 mg administered either once per day or twice per day.

3.58 Any of Methods 3.54 to 3.57, wherein said anterior segment tissue of the eye reaching said maximal concentration of the semifluorinated alkane (e.g., F6H8), is selected from the group consisting of meibomian glands, conjunctiva (bulbar), conjunctiva (palpebral), cornea, sclera (anterior), and tears.

3.59 Method 3.58, wherein said maximal concentration of semifluorinated alkane (e.g., F6H8) is reached within 0.25 to 2 hours (e.g., 0.25 to 1 hours, or 0.25 to 0.5 hours) after a single drop dose of the composition is administered either once per day or twice per day.

3.60 Any of Method 3.54 to 3.57, wherein said anterior segment tissue of the eye reaching said maximal concentration of the semifluorinated alkane (e.g., F6H8), is selected from the group consisting of lacrimal gland (accessory) and lacrimal gland (main).

3.61 Method 3.60, wherein said maximal concentration of semifluorinated alkane (e.g., F6H8) is reached within 3 to 5 hours (e.g., 4 hours) after a single drop dose of the composition is administered either once per day or twice per day.

3.62 Any of Methods 3.54 to 3.61, wherein the method provides a maximal concentration of the semifluorinated alkane (e.g., F6H8) of at least:

a. 222,000 ng/g of tissue in the Meibomian glands;

b. 5450 ng/g of tissue in the conjunctiva (bulbar);

c. 14,000 ng/g of tissue in the conjunctive (palpebral);

d. 8230 ng/g of tissue in the cornea;

e. 2270 ng/g of tissue in the sclera (anterior);

f. 4280 ng/g of tissue in the lacrimal gland (accessory);

g. 4130 ng/g of tissue in the lacrimal gland (main); and/or h. 1300 ng/g of tears;

after a single drop dose of the composition administered either once or twice per day.

3.63 Method 3.62, wherein the method provides a maximal concentration of the semifluorinated alkane (e.g., F6H8) of at least 5000 ng/g of tears, e.g., at least 10,000 ng/g, or at least 50,000 ng/g, or at least 100,000 ng/g, or at least 500,000 ng/g, or at least 1,000,000 ng/g, or at least 2,000,000 ng/g, up to about 2,330,000 ng/g of tears.

The present disclosure further provides an ophthalmic composition comprising a semifluorinated alkane for use in any of the Methods of 1 to 3 or any of their subsequent embodiments (i.e., Method 1.1 to 1.65, Method 2.1 to 2.64, and Method 3.1 to 3.63). In another aspect, the present disclosure also provides for the use of an ophthalmic composition comprising a semifluorinated alkane, i.e., an ophthalmic composition as defined in any of the Methods 1 to 3 or any their subsequent embodiments (i.e., Method 1.1 to 1.65, Method 2.1 to 2.64, and Method 3.1 to Method 3.63), in the preparation or manufacture of a topically administered ophthalmic medicine or medicament.

In a fourth aspect, the present disclosure provides for an ophthalmic composition comprising a semifluorinated alkane selected from the group consisting of $F(CF_2)_4(CH_2)_5H$, $F(CF_2)_4(CH_2)_6H$, $F(CF_2)_6(CH_2)_6H$, $F(CF_2)_6(CH_2)_8H$, and $F(CF_2)_8(CH_2)_8H$, for use in a method (Method 4) for the treatment of keratoconjunctivitis sicca (dry eye disease), and/or treating keratoconjunctivitis sicca (dry eye disease) due to Meibomian gland dysfunction and/or treating Meibomian gland dysfunction and/or for the treatment of a condition of the conjunctiva or cornea, wherein the method comprises a step of topically administering the composition to the eye of a patient in need thereof in a dose of a single drop per eye two times per day. Further embodiments of the present disclosure provide as follows:

4.1 The composition for use in Method 4, wherein the semifluorinated alkane is selected from the group consisting of $F(CF_2)_4(CH_2)_5H$ and $F(CF_2)_6(CH_2)_8H$.

4.2 The composition for use in Method 4 or any of 4.1, wherein the semifluorinated alkane is $F(CF_2)_6(CH_2)_8H$.

4.3 The composition for use in Method 4 or any of 4.1 et seq., wherein the composition comprises the single semifluorinated alkane.

4.4 The composition for use in Method 4 or any of 4.1 et seq., wherein the composition is free of any pharmaceutically active drug substance useful for ophthalmic treatment.

4.5 The composition for use in Method 4 or any of 4.1 et seq., wherein the composition consists of the single semifluorinated alkane.

4.6 The composition for use in Method 4 or any of 4.1 to 4.2, wherein the composition comprises at least one additional semifluorinated alkane.

4.7 The composition for use in Method 4.6, wherein the additional semifluorinated alkane has the formula $F(CF_2)_n(CH_2)_mH$, and wherein n is an integer from 4 to 8 and m is an integer from 5 to 10 and wherein the additional semifluorinated alkane is different from said first semifluorinated alkane.

4.8 The composition for use in Method 4.7, wherein the additional semifluorinated alkane is selected from the group consisting of $F(CF_2)_4(CH_2)_5H$, $F(CF_2)_4(CH_2)_6H$, $F(CF_2)_6(CH_2)_6H$, $F(CF_2)_6(CH_2)_8H$, $F(CF_2)_6(CH_2)_{10}H$, $F(CF_2)_8(CH_2)_8H$ and $F(CF_2)_8(CH_2)_{10}H$.

4.9 The composition for use in Method 4.6, 4.7 or 4.8, wherein the composition comprises the two semifluorinated alkanes.

4.10 The composition for use in any of Method 4.6 to 4.9, wherein the composition is free of any pharmaceutically active drug substance useful for ophthalmic treatment.

4.11 The composition for use in any of Method 4.6 to 4.10, wherein the composition consists of the two semifluorinated alkanes.

4.12 The composition for use in Method 4 or any of 4.1 et seq., wherein the ophthalmic composition is administered to the surface of the cornea and/or conjunctiva in the form of a liquid drop.

4.13 The composition for use in Method 4 or any of 4.1 et seq., wherein the patient suffers from keratoconjunctivitis sicca (dry eye disease), optionally wherein the patient suffers from keratoconjunctivitis sicca (dry eye disease) due to Meibomian gland dysfunction.

4.14 The composition for use in Method 4.13, wherein the dry eye disease is aqueous-deficient dry eye disease.

4.15 The composition for use in Method 4.13 or 4.14, wherein the dry eye disease is evaporative dry eye disease.

4.16 The composition for use in Method 4 or any of 4.1 et seq., wherein the patient suffers from Meibomian gland dysfunction.

4.17 The composition for use in Method 4.16, wherein the patient is non-responsive to traditional physical methods of treating Meibomian Gland Dysfunction (e.g., the methods discussed in Blackie et al., Review of Optometry, Jun. 21, 2012, pp. 1-12, which reference is incorporated by reference herein in its entirety).

4.18 The composition for use in Method 4 or any of 4.1 et seq., wherein the patient is non-responsive to treatment with aqueous ophthalmic eye drop compositions.

4.19 The composition for use in Method 4 or any of 4.1 et seq., wherein the volume of each drop is 9-13 μL, e.g., 9-12 μL, or 10-13 μL, or 10-12 μL, or 10-11 μL, or about 11 μL.

4.20 The composition for use in Method 4 or any of 4.1 et seq., wherein the composition is administered in a dose of a single drop per eye three times per day in net volume of 30-33 μL.

4.21 The composition for use in Method 4 or any of 4.1 et seq., wherein the composition is administered in a dose of a single drop per eye two times per day in net volume of 20-22 μL.

4.22 The composition for use in Method 4 or any of 4.1 et seq., wherein the composition is administered in a dose of a single drop per eye one times per day in net volume of 10-11 μL.

4.23 The composition for use in Method 4 or any of 4.1 et seq., wherein an ophthalmic tissue is enriched in the semifluorinated alkane, and wherein the release of the semifluorinated compound from the enriched ophthalmic tissue is delayed.

4.24 The composition for use in Method 4.23, wherein the enriched ophthalmic tissue is selected from the group consisting of the palpebral conjunctiva, the cornea, the Meibomian glands, the lacrimal glands and/or the bulbar conjunctiva.

4.25 The composition for use in Method 4.23 to 4.24, wherein the ophthalmic tissue are the Meibomian glands, e.g., of the upper and/or lower eyelid.

4.26 The composition for use in Method 4.23 to 4.25, wherein the enriched tissue releases all or substantially all of the semifluorinated alkane within 24 hours, optionally within 8 hours, of the last dose of the composition administered, optionally the enriched tissue releases at least 60% within 4 to 8 hours, or at least 80% within 8 hours, of the last dose of the composition administered.

4.27 The composition for use in Method 4.23 to 4.26, wherein after sequential dosing of the composition (e.g. the two doses administered within 24 hours), the ophthalmic tissue enriched in the semifluorinated alkane releases all or substantially all of the semifluorinated alkane within 24 hours, optionally within 8 hours, of the last dose administered, optionally the enriched tissue releases at least 50% within 4 to 8 hours, or at least 70% within 8 to 12 hours, of the last dose of the composition administered.

4.28 The composition for use in Method 4 or any of 4.1 et seq., wherein the ophthalmic tissue enriched in the semifluorinated alkane comprises about 0.00001 to 0.5 wt % of the semifluorinated alkane, optionally 0.0001 to 0.05 wt %, e.g., 0.0001 to 0.001 wt %, or 0.0004 to 0.0009 wt %, or 0.001 to 0.01 wt %, or 0.001 to 0.003 wt %, or 0.001 to 0.05%, or 0.005 to 0.03%, of the semifluorinated alkane.

4.29 The composition for use in Method 4 or any of 4.1 et seq., wherein the ophthalmic tissue enriched is the Meibomian glands, and the Meibomian glands comprise 0.0001 to 0.05 wt %, optionally 0.0005 to 0.05 wt %, or 0.001 to 0.03 wt % of the semifluorinated alkane.

4.30 The composition for use in Method 4 or any of 4.1 et seq., wherein treatment is performed for about at least 1 day, or for at least 5 days, or for at least 10 days, or for at least 30 days, or for at least 60, or for at least 90 days.

4.31 The composition for use in Method 4 or any of 4.1 et seq., wherein the patient is a human patient.

4.32 The composition for use in Method 4 or any of 4.1 et seq., wherein the patient is an animal patient, e.g., a mammal, such as, a dog, cat, rabbit and/or farm animal, such as a horse, pig, cow, or sheep.

4.33 The composition for use in Method 4.31, wherein the patient is a female patient.

4.34 The composition for use in Method 4.31, wherein the patient is a male patient.

4.35 The composition for use in Method 4.33 or 4.34, wherein the patient is aged 20-80 years old at the time of treatment, e.g., 20-50 years old, or 20-70 years old, or 30-80 years old, or 30-50 years old, or 30-70 years old, or 40-80 years old, or 40-60 years old, or 40-70 years old, or 50-80 years old, or 50-70 years old.

In further embodiments of the fourth aspect, the present disclosure further provides additional embodiments as follows:

4.36 The composition for use in Method 4, or in any of 4.1 to 4.35 wherein the composition consists of 1-(perfluorohexyl)octane (F6H8).

4.37 The composition for use in Method 4, or in any of 4.1 to 4.35, wherein the composition consists of a mixture of F6H8 and to 2-(perfluorohexyl)octane.

4.38 The composition for use in Method 4.37, wherein the composition comprises the 2-(perfluorohexyl)octane in an amount of up to about 3 wt %, or up to about 2 wt %, or up to about 1 wt %.

4.39 The composition for use in Method 4, or in any of 4.1 to 4.35, or 4.36 to 4.38, wherein the composition is administered two times per day per eye of a patient in a dose of a single drop of about 10-12 μl, or about 10-11 μl or about 11 μl.

4.40 The composition for use in a Method 4 or any of 4.1 to 4.39, wherein the composition is administered in a dose of a single drop per eye two times per day in a net volume of 20-24 μL.

4.41 The composition for use in Method 4 or in any of 4.1-4.40, wherein the patient is characterized by at least 2 of the criteria selected from the group consisting of:

i. a tear film breakup time (TFBUT) of 5 sec, or lower (i.e. between 0 and 5 sec), ii. a total ocular surface disease index (OSDI) of 25 or higher (i.e. an OSDI score of between 25 and 100), iii. a total corneal fluorescein staining (NEI scale) between 4 and 11, iv. a Schirmer's Test I of 5 mm, or greater (e.g. equal to, or greater than 10 mm, or equal to or higher than 15 mm), and v. a Meibomian gland dysfunction (MGD) score of 3, or higher (i.e. a score of between 3 and 15).

4.42 The composition for use in Method 4.41, wherein the patient is characterized by at least 2 of the criteria selected from the group consisting of:
i. a tear film breakup time (TFBUT) of 3.8 sec or lower (i.e. between 0 and 3.8 sec), or between 2 and 3.8 sec,
ii. a total ocular surface disease index (OSDI) of 36 or higher (i.e. between 36 and 100), or between 36 and 74,
iii. a total corneal fluorescein staining (NEI scale) between 4.6 and 8.8, preferably between 5 and 9;
iv. a Schirmer's Test I of 5 mm, or greater, preferably 10 mm or greater, and
v. a Meibomian gland dysfunction (MGD) score of 3.6, or higher (e.g. a score of between 3.6 and 15), or a score of between 3.6 and 11, preferably between 4 and 15.

4.43 The composition for use in Method 4.41 or 4.42, wherein the patient has at least one eye which meets all of the criteria (i), (iii), (iv), and (v).

4.44 The composition for use in Method 4, or in any of 4.1-4.43, wherein the patient has a history of kerato-conjunctivitis sicca (dry eye disease) in one or both eyes for at least six months.

4.45 The composition for use in Method 4, or in any of 4.1-4.44, wherein the composition is effective in reducing the ocular surface damage of one or more corneal regions and/or one or more symptoms of dryness in a patient suffering from keratoconjunctivitis sicca (dry eye disease) due to Meibomian gland dysfunction and/or Meibomian gland dysfunction.

4.46 The composition for use in Method 4.45, wherein the composition is effective in reducing said ocular surface damage and symptoms of dryness within 2 weeks, or within 4 weeks, or within 8 weeks after first administration of the composition.

4.47 The composition for use in Method 4.45-4.46, wherein the ocular surface damage of one or more corneal regions is selected from the total corneal region, the central corneal region, the nasal corneal region, the temporal corneal region, and combinations thereof.

4.48 The composition for use in Method 4.45 to 4.47, wherein the reduction of ocular surface damage is determined by corneal fluorescein staining (according to the NEI scale).

4.49 The composition for use in Method 4.45 to 4.48, wherein the damage of the ocular surface is determined by grading one or more of the corneal regions selected from the group consisting of the total corneal region, the central corneal region, the nasal corneal region, the temporal corneal region, and combinations thereof by fluorescein staining of the cornea.

4.50 The composition for use in Method 4, or in any of 4.1-4.49, wherein the composition is effective in reducing one or more symptoms of dryness in a patient suffering from keratoconjunctivitis sicca (dry eye disease) due to Meibomian gland dysfunction and/or Meibomian gland dysfunction.

4.51 The composition for use in Method 4.45 to 4.50, wherein the one or more symptoms of dryness are selected from the group consisting of:
i. severity of dryness;
ii. blurred vision;
iii. sensitivity of light;
iv. frequency of dryness;
v. awareness of dryness; and
vi. any combination thereof.

4.52 The composition for use in 4.51, wherein the symptoms (i) to (iii) are determined on a visual analog scale (VAS) from 0% to 100% indicating the level of discomfort of the patient and wherein the symptoms (iv) to (v) are determined on a visual analog scale (VAS) from 0% to 100% indicating the percentage of time said dryness symptoms are experienced by the patient.

4.53 The composition for use in Method 4.45 to 4.52, wherein the one or more symptoms of dryness are graded using the total ocular surface disease index (OSDI) score.

4.54 The composition for use in Method 4.53, wherein the total ocular surface disease index (OSDI) score is assessed on a scale of 1 to 100 with higher scores representing greater disability of the patient.

4.55 The composition for use in Method 4.36 to 4.54, wherein the patient suffers from a co-morbidity, for example, conjunctivitis, stye, chalazion, blepharitis, ectropion, eyelid laxity, eyelid edema, eyelid dermatitis, punctate keratopathy, or ocular allergies, or any combination thereof.

4.56 The composition for use in Method 4.36 to 4.55, wherein the patient suffers from keratoconjunctivitis sicca which is caused by treatment of a co-morbidity, for example, treatment with any one or more of: isotretinoin, sedatives, diuretics, tricyclic antidepressants, antihypertensives, anticholinergics, oral contraceptives, antihistamine, nasal decongestants, beta-adrenergic antagonists, phenothiazines, atropine opiates (e.g., morphine), optionally wherein any such treatment is concurrent or previous, and further optionally, wherein any such treatment is systemic (e.g., oral or parenteral).

4.57 The composition for use in Method 4.36 to 4.56, wherein the patient suffers from keratoconjunctivitis sicca which is caused by ocular surgical intervention, for example, corneal surgery, refractive surgery, LASIK surgery, cataract surgery, optionally wherein any such ocular surgery is concurrent or previous.

4.58 The composition for use in Method 4.36 to 4.57, wherein the patient is concomitantly under treatment with another topical ophthalmic medication, for example, an antibiotic, antifungal, corticosteroid, immunosuppressant, sympathomimetic, anesthetic, antihistamine, or any combination thereof.

4.59 The composition for use in Method 4.36 to 4.58, wherein the patient is a contact lens wearer.

4.60 The composition for use in Method 4.36 to 4.59, wherein the patient was unresponsive or insufficiently response to previous treatment for keratoconjunctivitis sicca (dry eye disease).

4.61 The composition for use in Method 4.60, wherein said previous treatment comprise one or more of the following treatment methods: topical aqueous immunosuppressant administration (e.g., topical aqueous ciclosporin), topical corticosteroid administration, or topical aqueous artificial tears administration.

In a fifth aspect, related to the fourth aspect, the present disclosure further provides a method (Method 5) for the treatment of keratoconjunctivitis sicca (dry eye disease), and/or treating keratoconjunctivitis sicca (dry eye disease) due to Meibomian gland dysfunction and/or treating Meibomian gland dysfunction and/or for the treatment of a condition of the conjunctiva or cornea, wherein the method comprises the step of topically administering an ophthalmic composition comprising a semifluorinated alkane selected from the group consisting of $F(CF_2)_4(CH_2)_5H$, $F(CF_2)_4$ $(CH_2)_6H$, $F(CF_2)_6(CH_2)_6H$, $F(CF_2)_6(CH_2)_8H$, and $F(CF_2)_8$ $(CH_2)_8H$, to the eye of a patient in need thereof in a dose of a single drop per eye two times per day. Further embodiments of the present disclosure provide as follows:

5.1 Method 5, wherein the semifluorinated alkane is selected from the group consisting of $F(CF_2)_4(CH_2)_5H$ and $F(CF_2)_6(CH_2)_8H$.

5.2 Method 5 or any of 5.1, wherein the semifluorinated alkane is $F(CF_2)_6(CH_2)_8H$.

5.3 Method 5 or any of 5.1 et seq., wherein the composition comprises the single semifluorinated alkane.

5.4 Method 5 or any of 5.1 et seq., wherein the composition is free of any pharmaceutically active drug substance useful for ophthalmic treatment.

5.5 Method 5 or any of 5.1 et seq., wherein the composition consists of the single semifluorinated alkane.

5.6 Method 5 or any of 5.1 to 4.2, wherein the composition comprises at least one additional semifluorinated alkane.

5.7 Method 5.6, wherein the additional semifluorinated alkane has the formula $F(CF_2)_n(CH_2)_mH$, and wherein n is an integer from 4 to 8 and m is an integer from 5 to 10 and wherein the additional semifluorinated alkane is different from said first semifluorinated alkane.

5.8 Method 5.7, wherein the additional semifluorinated alkane is selected from the group consisting of $F(CF_2)_4(CH_2)_5H$, $F(CF_2)_4(CH_2)_6H$, $F(CF_2)_6(CH_2)_6H$, $F(CF_2)_6(CH_2)_8H$, $F(CF_2)_6(CH_2)_{10}H$, $F(CF_2)_8(CH_2)_8H$ and $F(CF_2)_8(CH_2)_{10}H$.

5.9 Method 5.6, 5.7 or 5.8, wherein the composition comprises the two semifluorinated alkanes.

5.10 Method 5.6 to 5.9, wherein the composition is free of any pharmaceutically active drug substance useful for ophthalmic treatment.

5.11 Method 5.6 to 5.10, wherein the composition consists of the two semifluorinated alkanes.

5.12 Method 5 or any of 5.1 et seq., wherein the ophthalmic composition is administered to the surface of the cornea and/or conjunctiva in the form of a liquid drop.

5.13 Method 5 or any of 5.1 et seq., wherein the patient suffers from keratoconjunctivitis sicca (dry eye disease), optionally wherein the patient suffers from keratoconjunctivitis sicca (dry eye disease) due to Meibomian gland dysfunction.

5.14 Method 5.13, wherein the dry eye disease is aqueous-deficient dry eye disease.

5.15 Method 5.13 or 5.14, wherein the dry eye disease is evaporative dry eye disease.

5.16 Method 5 or any of 5.1 et seq., wherein the patient suffers from Meibomian gland dysfunction.

5.17 Method 5.16, wherein the patient is non-responsive to traditional physical methods of treating Meibomian Gland Dysfunction (e.g., the methods discussed in Blackie et al., Review of Optometry, Jun. 21, 2012, pp. 1-12, which reference is incorporated by reference herein in its entirety).

5.18 Method 5 or any of 5.1 et seq., wherein the patient is non-responsive to treatment with aqueous ophthalmic eye drop compositions.

5.19 Method 5 or any of 5.1 et seq., wherein the volume of each drop is 9-13 µL, e.g., 9-12 µL, or 10-13 µL, or 10-12 µL, or 10-11 µL, or about 11 µL.

5.20 Method 5 or any of 5.1 et seq., wherein the composition is administered in a dose of a single drop per eye two times per day in net volume of 20-22 µL.

5.21 Method 5 or any of 5.1 et seq., wherein an ophthalmic tissue is enriched in the semifluorinated alkane, and wherein the release of the semifluorinated compound from the enriched ophthalmic tissue is delayed.

5.22 Method 5.21 wherein the enriched ophthalmic tissue is selected from the group consisting of the palpebral conjunctiva, the cornea, the Meibomian glands, the lacrimal glands and/or the bulbar conjunctiva.

5.23 Method 5.21 to 5.22, wherein the ophthalmic tissue are the Meibomian glands, e.g., of the upper and/or lower eyelid.

5.24 Method. 21 to 5.23, wherein the enriched tissue releases all or substantially all of the semifluorinated alkane within 24 hours, optionally within 8 hours, of the last dose of the composition administered, optionally the enriched tissue releases at least 60% within 4 to 8 hours, or at least 80% within 8 hours, of the last dose of the composition administered.

5.25 Method 5.21 to 5.24, wherein after sequential dosing of the composition (e.g. the two doses administered within 24 hours), the ophthalmic tissue enriched in the semifluorinated alkane releases all or substantially all of the semifluorinated alkane within 24 hours, optionally within 8 hours, of the last dose administered, optionally the enriched tissue releases at least 50% within 4 to 8 hours, or at least 70% within 8 to 12 hours, of the last dose of the composition administered.

5.26 Method 5 or any of 5.1 et seq., wherein the ophthalmic tissue enriched in the semifluorinated alkane comprises about 0.00001 to 0.5 wt % of the semifluorinated alkane, optionally 0.0001 to 0.05 wt %, e.g., 0.0001 to 0.001 wt %, or 0.0004 to 0.0009 wt %, or 0.001 to 0.01 wt %, or 0.001 to 0.003 wt %, or 0.001 to 0.05%, or 0.005 to 0.03%, of the semifluorinated alkane.

5.27 Method 5 or any of 5.1 et seq., wherein the ophthalmic tissue enriched is the Meibomian glands, and the Meibomian glands comprise 0.0001 to 0.05 wt %, optionally 0.0005 to 0.05 wt %, or 0.001 to 0.03 wt % of the semifluorinated alkane.

5.28 Method 5 or any of 5.1 et seq., wherein treatment is performed for about at least 1 day, or for at least 5 days, or for at least 10 days, or for at least 30 days, or for at least 60, or for at least 90 days.

5.29 Method 5 or any of 5.1 et seq., wherein the patient is a human patient.

5.30 Method 5 or any of 5.1 et seq., wherein the patient is an animal patient, e.g., a mammal, such as, a dog, cat, rabbit and/or farm animal, such as a horse, pig, cow, or sheep.

5.31 Method 5.29, wherein the patient is a female patient.

5.32 Method 5.29, wherein the patient is a male patient.

5.33 Method 5.31 or 5.32, wherein the patient is aged 20-80 years old at the time of treatment, e.g., 20-50 years old, or 20-70 years old, or 30-80 years old, or 30-50 years old, or 30-70 years old, or 40-80 years old, or 40-60 years old, or 40-70 years old, or 50-80 years old, or 50-70 years old.

In further embodiments of the fifth aspect, the present disclosure further provides additional embodiments as follows:

5.34 Method 5, or any of 5.1 to 5.33 wherein the composition consists of 1-(perfluorohexyl)octane (F6H8).

5.35 Method 5, or any of 5.1 to 5.33, wherein the composition consists of a mixture of F6H8 and to 2-(perfluorohexyl)octane.

5.36 Method 5.35, wherein the composition comprises the 2-(perfluorohexyl)octane in an amount of up to about 3 wt %, or up to about 2 wt %, or up to about 1 wt %.

5.37 Method 5, or any of 5.1-5.36, wherein the composition is administered two times per day per eye of a patient in a dose of a single drop of about 10-12 µl, or about 10-11 µl or about 11 µl.

5.38 Method 5, or any of 5.1-5.37, wherein the composition is administered in a dose of a single drop per eye two times per day in a net volume of 20-24 µl.

5.39 Method 5 or any of 5.1-5.37, wherein the patient is characterized by at least 2 of the criteria selected from the group consisting of:
 i. a tear film breakup time (TFBUT) of 5 sec, or lower (i.e. between 0 and 5 sec),
 ii. a total ocular surface disease index (OSDI) of 25, or higher (i.e. an OSDI score of between 25 and 100),
 iii. a total corneal fluorescein staining (NEI scale) between 4 and 11 (e.g., between 5 and 9),
 iv. a Schirmer's Test I greater than 5 mm (e.g. equal to or greater than 10 mm, or equal to or higher than 15 mm), and
 v. a MGD score of 3, or higher (i.e. a score of between 3 and 15, e.g., 4, or higher).

5.40 Method 5, or any of 5.1 to 5.38, wherein the patient is characterized by at least 2 of the criteria selected from the group consisting of:
 i. a tear film breakup time (TFBUT) of 3.8 sec, or lower (i.e. between 0 and 3.8 sec), or between 2 and 3.8 sec;
 ii. a total ocular surface disease index (OSDI) of 36 or higher (i.e. an OSDI score of between 36 and 100), or between 36 and 74;
 iii. a total corneal fluorescein staining (NEI scale) between 4 and 8.8, preferably between 5 and 9;
 iv. a Schirmer's Test I greater than 5 mm (e.g. equal to or greater than 10 mm, or equal to or higher than 15 mm), and
 v. a MGD score of 3.6, or higher (e.g. a score of between 3.6 and 15), or a score of between 3.6 and 11, preferably between 4 and 15.

5.41 Method 5.39 or 5.40, wherein the patient has at least one eye which meets criteria (i), (iii), (iv), and (v), or wherein the patient 5.42 Method 5, or any of 5.1-5.41, wherein the patient has a history of keratoconjunctivitis sicca (dry eye disease) in one or both eyes for at least six months.

5.43 Method 5, or any of 5.1 to 5.42, wherein the composition is effective in reducing the ocular surface damage of one or more corneal regions and/or one or more symptoms of dryness in a patient suffering from keratoconjunctivitis sicca (dry eye disease) due to Meibomian gland dysfunction and/or Meibomian gland dysfunction.

5.44 Method 5.43, wherein the composition is effective in reducing said ocular surface damage and symptoms of dryness within 2 weeks, within 4 weeks, within 8 weeks after first administration of the composition.

5.45 Method 5.43 to 5.44, wherein the ocular surface damage of one or more corneal regions is selected from the total corneal region, the central corneal region, the nasal corneal region, the temporal corneal region and combinations thereof.

5.46 Method 5.43 to 5.45, wherein the reduction of ocular surface damage is determined by corneal fluorescein staining (according to the NEI scale).

5.47 Method 5.43 to 5.46, wherein the damage of the ocular surface is determined by grading one or more of the corneal regions selected from the group consisting of the total corneal region, the central corneal region, the nasal corneal region, the temporal corneal region, and combinations thereof, by fluorescein staining of the cornea.

5.48 Method 5, or any of 5.1-5.47, wherein the composition is effective in reducing one or more symptoms of dryness, in a patient suffering from keratoconjunctivitis sicca (dry eye disease) due to Meibomian gland dysfunction and/or Meibomian gland dysfunction.

5.49 Method 5.43 to 5.48, wherein the one or more ocular symptoms are selected from the group consisting of:
 i. severity of dryness;
 ii. blurred vision;
 iii. sensitivity of light;
 iv. frequency of dryness;
 v. awareness of dryness; and
 vi. any combination thereof.

5.50 Method 5.49, wherein the symptoms (i) to (iii) are determined on a visual analog scale (VAS) from 0% to 100% indicating the level of discomfort of the patient and wherein the symptoms (iv) to (v) are determined on a visual analog scale (VAS) from 0% to 100% indicating the percentage of time said dryness symptoms are experienced by the patient.

5.51 Method 5.43 to 5.49, wherein the one or more symptoms of dryness is graded using the total ocular surface disease index (OSDI) score.

5.52 Method 5.50, wherein the total ocular surface disease index (OSDI) score is assessed on a scale of 1 to 100 with higher scores representing greater disability of the patient.

5.53 Method 5.34 to 5.52, wherein the patient suffers from a co-morbidity, for example, conjunctivitis, stye, chalazion, blepharitis, ectropion, eyelid laxity, eyelid edema, eyelid dermatitis, punctate keratopathy, or ocular allergies, or any combination thereof.

5.54 The composition for use in Method 5.34 to 5.53, wherein the patient suffers from keratoconjunctivitis sicca which is caused by treatment of a co-morbidity, for example, treatment with any one or more of: isotretinoin, sedatives, diuretics, tricyclic antidepressants, antihypertensives, anticholinergics, oral contraceptives, antihistamine, nasal decongestants, beta-adrenergic antagonists, phenothiazines, atropine opiates (e.g., morphine), optionally wherein any such treatment is concurrent or previous, and further optionally, wherein any such treatment is systemic (e.g., oral or parenteral).

5.55 The composition for use in Method 5.34 to 5.54, wherein the patient suffers from keratoconjunctivitis sicca which is caused by ocular surgical intervention, for example, corneal surgery, refractive surgery, LASIK surgery, cataract surgery, optionally wherein any such ocular surgery is concurrent or previous.

5.56 The composition for use in Method 5.34 to 5.55, wherein the patient is concomitantly under treatment with another topical ophthalmic medication, for example, an antibiotic, antifungal, corticosteroid, immunosuppressant, sympathomimetic, anesthetic, antihistamine, or any combination thereof.

5.57 The composition for use in Method 5.34 to 5.56, wherein the patient is a contact lens wearer.

5.58 The composition for use in Method 5.34 to 5.57, wherein the patient was unresponsive or insufficiently response to previous treatment for keratoconjunctivitis sicca (dry eye disease).

5.59 The composition for use in Method 5.58, wherein said previous treatment comprise one or more of the following treatment methods: topical aqueous immunosuppressant administration (e.g., topical aqueous ciclosporin), topical corticosteroid administration, or topical aqueous artificial tears administration.

In a sixth aspect, the present disclosure also provides for:

6.1 An ophthalmic composition consisting of 1-perfluorohexyl-octane (F6H8), for use in a method of treating keratoconjunctivitis sicca (dry eye disease), and/or treating keratoconjunctivitis sicca (dry eye disease) due to Meibomian gland dysfunction and/or treating Meibomian gland dysfunction and/or treating of a condition of the conjunctiva or cornea, wherein the method comprises a step of topically administering the composition to the eye of a patient in need thereof, a dose of a single drop per eye two times per day, of about 10-12 μL per eye.

6.2 An ophthalmic composition consisting of 1-perfluorohexyl-octane (F6H8), and optionally up to 3 wt %, or up to about 1 wt % of 2-perfluorohexyl-octane, for use in a method of treating keratoconjunctivitis sicca (dry eye disease), and/or treating keratoconjunctivitis sicca (dry eye disease) due to Meibomian gland dysfunction and/or treating Meibomian gland dysfunction and/or treating a condition of the conjunctiva or cornea, wherein the method comprises a step of topically administering the composition to an eye of a patient in need thereof, a dose of a single drop per eye two times per day, of about 10-12 μL per eye.

6.3 An ophthalmic composition consisting of 1-perfluorohexyl-octane (F6H8), for use in a method of treating keratoconjunctivitis sicca (dry eye disease), due to Meibomian gland dysfunction and/or treating of a condition of the conjunctiva or cornea, wherein the method comprises a step of topically administering the composition two times per day to the eye of a patient at a dose of a single drop of about 10-12 μL per eye.

6.4 The composition for use of 6.1, 6.2 or 6.3, wherein the composition is administered as a single drop of 10-11 μL, preferably as a single drop of about 11 μL to the eye of a patient.

6.5 The composition for use of 6.1, 6.2 or 6.3, wherein the composition is administered in a dose of a single drop per eye two times per day in a net volume of 20-24 μL.

6.6 The composition for use of 6.4, wherein the composition is administered at a dose of a single drop per eye two times per day in a net volume of 20-22 μL, or a net volume of about 22 μL.

6.7 The composition for use of 6.1 to 6.6, wherein the second dose is administered at least 1 hour after the first dose, or wherein the second dose is administered at least 2 hours after the first dose, or wherein the second dose is administered at least 3 hours after the first dose, or wherein the second dose is administered at least 4 hours after the first dose.

6.8 The composition for use of 6.1 to 6.7, wherein the time interval between the first and second dose is administered is no more than about 8 hours, or no more than 12 hours.

6.9 The composition for use of 6.1 to 6.8, wherein the patient has a history of keratoconjunctivitis sicca (dry eye disease), or keratoconjunctivitis sicca due to Meibomian gland dysfunction, or Meibomian gland dysfunction in one or both eyes for at least six months prior to treatment.

6.10 The composition for use of 6.1 to 6.9, wherein the method of treatment comprises administering the composition over a period of at least 2 weeks, at least 4 weeks, or at least 8 weeks.

6.11 The composition for use of 6.1 to 6.10, wherein the patient meets at least 2 of the criteria selected from the group consisting of:
   i. a tear film breakup time (TFBUT) of 3.8 sec or lower (e.g. between 0 and 3.8 sec),
   ii. a total ocular surface disease index (OSDI) of 36 or higher (e.g. between 36 and 100),
   iii. a total corneal fluorescein staining (NEI scale) between 5 and 9;
   iv. a Schirmer's Test I of 10 mm, or greater,
   v. a Meibomian gland dysfunction (MGD) score of 4, or higher (e.g. a score of between 4 and 15), and
   vi. a VAS severity of dryness score of higher than 50, e.g. between 50 and 100.

6.12 The composition for use of 6.1 to 6.11, wherein the patient meets at least 2 of the criteria selected from the group consisting of:
   i. a tear film breakup time (TFBUT) of between 2 and 3.8 sec,
   ii. a total ocular surface disease index (OSDI) of between 36 and 74,
   iii. a total corneal fluorescein staining (NEI scale) between 5 and 9,
   iv. a Schirmer's Test I of 10 mm, or greater,
   v. a Meibomian gland dysfunction (MGD) score of between 4 and 11; and
   vi. a VAS severity of dryness score of between 50 and 90.

6.13 The composition for use of 6.11 or 6.12, wherein the patient has at least one eye which meets all of the criteria (i.e. signs of dry eye disease) (i), (iii), (iv), and (v).

6.14 The composition for use of 6.11 or 6.12, wherein the patient meets all of the criteria of (i) to (vi).

6.15 The composition for use of 6.11 or 6.12, wherein the patient is characterized by at least one criterion (i.e. relating to the signs of dry eye disease) selected from (i), (iii), (iv) and (v) and at least one criterion (i.e. relating to the symptoms of dry eye disease) selected from (ii) and (vi).

6.16 The composition for use of 6.1 to 6.10, wherein the patient meets at least 2 of the criteria selected from the group consisting of:
   i. a tear film breakup time (TFBUT) of 3.8 sec or lower (e.g. between 0 and 3.8 sec),
   ii. a total corneal fluorescein staining (NEI scale) between 5 and 9;
   iii. a Meibomian gland dysfunction (MGD) score of 4, or higher (e.g. a score of between 4 and 15)
   iv. a total ocular surface disease index (OSDI) of 36 or higher (e.g. between 36 and 100),
   v. a VAS severity of dryness score of higher than 50, e.g. between 50 and 100.

6.17 The composition for use of 6.1 to 6.10, or 6.16, wherein the patient meets at least 2 of the criteria selected from the group consisting of:
   i. a tear film breakup time (TFBUT) of between 2 and 3.8 sec,
   ii. a total corneal fluorescein staining (NEI scale) between 5 and 9;

iii. a Meibomian gland dysfunction (MGD) score of between 4 and 11, and iv. a total ocular surface disease index (OSDI) of between 36 and 74)

v. a VAS severity of dryness score of between 50 and 90.

6.18 The composition for use of 6.16 or 6.17, wherein the patient has at least one eye which meets all of the criteria (i.e. signs of dry eye disease) (i), (ii), and (iii).

6.19 The composition for use of 6.16 or 6.17, wherein the patient meets all of the criteria of (i) to (v).

6.20 The composition for use of 6.16 or 6.17, wherein the patient is characterized by at least one criterion (i.e. relating to the signs of dry eye disease) selected from (i), (ii), and (iii) and at least one criterion (i.e. relating to the symptoms of dry eye disease) selected from (iv) and (v).

6.21 The composition for use of 6.1 to 6.20, wherein the total ocular surface disease index (OSDI) score is assessed on a scale of 1 to 100, with higher scores representing a greater disability of the patient.

6.22 The composition for use of 6.1 to 6.21, wherein the patient has a condition of the cornea characterized by ocular surface damage in one or more regions of the cornea, for example, the total corneal region and/or the central corneal region and/or the nasal corneal region and/or the temporal corneal region.

6.23 The composition for use of 6.1 to 6.22, wherein the treatment comprises the reduction of ocular surface damage in one or more regions of the cornea, for example, the total corneal region and/or the central corneal region and/or the nasal corneal region and/or the temporal corneal region.

6.24 The composition for use of 6.23 wherein the patient has a condition of the cornea characterized by ocular surface damage, and wherein the method of treatment comprises treating or reducing the ocular surface damage of:

i. the total and central corneal region;

ii. the total and nasal corneal region iii. the total and temporal corneal region iv. the central and nasal corneal region v. the central and temporal corneal region 6.25 The composition for use of 6.1 to 6.24, wherein the method comprises treating or reducing the ocular surface damage of one or more corneal regions and/or treating or reducing one or more symptoms of dryness in a patient suffering from keratoconjunctivitis sicca (dry eye disease) due to Meibomian gland dysfunction and/or Meibomian gland dysfunction.

6.26 The composition for use of 6.25, wherein the method comprises treating or reducing the ocular surface damage of one or more corneal regions, and treating or reducing one or more symptoms of dryness in a patient suffering from keratoconjunctivitis sicca (dry eye disease) due to Meibomian gland dysfunction.

6.27 The composition for use of 6.26, wherein the ocular surface damage of one or more corneal regions is selected from (a) the total corneal region, (b) the central corneal region, (c) the nasal corneal region, (d) the temporal corneal region and (e) any combination thereof.

6.28 The composition for use in of 6.22 to 6.27, wherein the ocular surface damage and/or reduction thereof is determined by corneal fluorescein staining, optionally wherein grading of the one or more corneal regions by fluorescein staining is conducted using the (National Eye Institute) NEI scale.

6.29 The composition for use of 6.25 to 6.28, wherein the one or more symptoms of dryness are selected from (a) the severity of dryness (b) blurred vision, (c) sensitivity to light, (d) frequency of dryness; (e) awareness of dryness, and (d) any combination thereof.

6.30 The composition for use of 6.29 wherein the symptoms (a) to (c) are determined on a visual analog scale (VAS) from 0% to 100% indicating the level of discomfort, and wherein the symptoms (d) and (e) are determined on a visual analog scale (VAS) from 0% to 100% indicating the percentage of time the dryness symptoms are experienced by the patient.

6.31 The composition for use of 6.11 to 6.30, wherein the symptom of dryness and/or reduction thereof is graded using a total ocular surface disease index (OSDI) score.

6.32 The composition for use of 6.31 wherein the total ocular surface disease index (OSDI) score is assessed on a scale of 1 to 100 with higher scores representing greater disability of the patient.

6.33 The composition for use of 6.1 to 6.32, wherein the composition is effective in reducing the symptom severity of dryness within 2 weeks after start of treatment.

6.34 The composition for use of 6.33, wherein the symptom severity of dryness is reduced by at least 25% in said patient.

6.35 The composition for use of 6.1 to 6.34, wherein the patient has keratoconjunctivitis sicca (dry eye disease) selected from evaporative dry eye disease, or wherein the patient has keratoconjunctivitis sicca (dry eye disease) selected from evaporative dry eye disease, due to Meibomian gland dysfunction.

6.36 The composition for use of 6.1 to 6.35, wherein the patient does not suffer from aqueous dry eye disease or aqueous tear-deficient dry eye disease 6.37 The composition for use of 6.1 to 6.36, wherein treatment is performed for about at least 1 day, or for at least 5 days, or for at least 10 days, or for at least 30 days, or for at least 60, or for at least 90 days.

6.38 The composition for use of 6.1 to 6.37, wherein the patient is a human patient.

6.39 The composition for use of 6.38, wherein the patient is a female patient.

6.40 The composition for use in of 6.38, wherein the patient is a male patient.

6.41 The composition for use of 6.39 or 6.40, wherein the patient is aged 20-80 years old at the time of treatment, e.g., 20-50 years old, or 20-70 years old, or 30-80 years old, or 30-50 years old, or 30-70 years old, or 40-80 years old, or 40-60 years old, or 40-70 years old, or 50-80 years old, or 50-70 years old.

6.42 The composition for use of 6.1 to 6.41, wherein wherein the patient suffers from a co-morbidity, for example, conjunctivitis, stye, chalazion, blepharitis, ectropion, eyelid laxity, eyelid edema, eyelid dermatitis, punctate keratopathy, or ocular allergies, or any combination thereof.

6.43 The composition for use of 6.1 to 6.42, wherein the patient suffers from keratoconjunctivitis sicca which is caused by treatment of a co-morbidity, for example, treatment with any one or more of: isotretinoin, sedatives, diuretics, tricyclic antidepressants, antihypertensives, anticholinergics, oral contraceptives, antihistamine, nasal decongestants, beta-adrenergic antagonists, phenothiazines, atropine opiates (e.g., morphine), optionally wherein any such treatment is concurrent or previous, and further optionally, wherein any such treatment is systemic (e.g., oral or parenteral).

6.44 The composition for use of 6.1 to 6.43, wherein the patient suffers from keratoconjunctivitis sicca which is caused by ocular surgical intervention, for example, corneal surgery, refractive surgery, LASIK surgery, cataract surgery, optionally wherein any such ocular surgery is concurrent or previous.

6.45 The composition for use 6.1 to 6.44, wherein the patient is concomitantly under treatment with another topical ophthalmic medication, for example, an antibiotic, antifungal, corticosteroid, immunosuppressant, sympathomimetic, anesthetic, antihistamine, or any combination thereof.

6.46 The composition for use of 6.1 to 6.45, wherein the patient is a contact lens wearer.

6.47 The composition for use of 6.1 to 6.46, wherein the patient was unresponsive or insufficiently response to previous treatment for keratoconjunctivitis sicca (dry eye disease).

6.48 The composition for use of 6.47, wherein said previous treatment comprise one or more of the following treatment methods: topical aqueous immuno-suppressant administration (e.g., topical aqueous ciclosporin), topical corticosteroid administration, or topical aqueous artificial tears administration.

The compositions for use as defined according to the present invention may be provided to the patient in the form of a kit. In a further and related aspect to the aspect 6, the present disclosure also provides for the use of a kit, or a kit for use as follows:

6.49 A kit comprising:
   a. an ophthalmic composition essentially consisting of 1-perfluorohexyloctane, or a composition as defined in any one of the compositions of 6.1 or 6.2, and
   b. a container for holding the composition,
   for use in a method of treating keratoconjunctivitis sicca (dry eye disease), and/or treating keratoconjunctivitis sicca (dry eye disease) due to Meibomian gland dysfunction and/or treating Meibomian gland dysfunction and/or treating of a condition of the conjunctiva or cornea.

6.50 A kit for use of 6.49, for use in any one of the methods described in 6.1 to 6.48.

6.51 The kit for use of 6.49, for use in a method of treating keratoconjunctivitis sicca (dry eye disease) due to Meibomian gland dysfunction and/or treating a condition of the cornea.

6.52 The kit for use of 6.49 to 6.51, wherein the container is adapted to hold at least at least 600-720 μl of the composition.

6.53 The kit for use of 6.49 to 6.52, wherein the container is adapted to hold an amount of composition supporting a two-times daily treatment for at least 30 days.

6.54 The kit for use of 6.49 to 6.53, wherein the kit further comprises a drop dispenser adapted to dispense a drop of between 10-12 μl volume, or a drop of about 10 to 11 μl volume, or a drop of about 11 μl volume.

6.55 The kit for use of 6.49 to 6.54, wherein the kit further comprises instructions for use, and wherein the instructions for use are in an readable or tangible form, preferably in printed form (e.g. provided in the form of a leaflet or insert of container label) or in any machine- or computer-readable form (e.g. a machine-readable label such as for example a barcode or QR code)

indicating two-times per day administration of the composition daily, according to any one of the methods described in 6.1 to 6.48, or optionally, according to any one of the preceding methods of 4, or 4.1 to 4.61, or methods 5, or 5.1 to 5.59.

The present disclosure also further provides for a seventh aspect, related to the sixth aspect, in respect of a method of treatment in accordance with the following embodiments:

7.1 A method of treating keratoconjunctivitis sicca (dry eye disease), and/or treating keratoconjunctivitis sicca (dry eye disease) due to Meibomian gland dysfunction and/or treating Meibomian gland dysfunction and/or treating of a condition of the conjunctiva or cornea, wherein the method comprises a step of topically administering an ophthalmic composition consisting of 1-perfluorohexyl-octane (F6H8) to the eye of a patient in need thereof, in a dose of a single drop per eye two times per day, of about 10-12 μL per eye.

7.2 A method of treating keratoconjunctivitis sicca (dry eye disease), and/or treating keratoconjunctivitis sicca (dry eye disease) due to Meibomian gland dysfunction and/or treating Meibomian gland dysfunction and/or treating a condition of the conjunctiva or cornea, wherein the method comprises a step of topically administering an ophthalmic composition consisting of 1-perfluorohexyl-octane (F6H8), and optionally up to 3 wt %, or up to about 1 wt % of 2-perfluorohexyl-octane, to an eye of a patient in need thereof, in a dose of a single drop per eye two times per day, of about 10-12 μL per eye.

7.3 A method of treating keratoconjunctivitis sicca (dry eye disease), due to Meibomian gland dysfunction and/or treating of a condition of the conjunctiva or cornea, wherein the method comprises a step of topically administering an ophthalmic composition consisting of 1-perfluorohexyl-octane (F6H8), two times per day to an eye of a patient in need thereof at a dose of a single drop of about 10-12 μL per eye.

7.4 The method of 7.1, 7.2 or 7.3, wherein the composition is administered as a single drop of 10-11 μL, preferably as a single drop of about 11 μL to the eye of a patient.

7.5 The method of 7.1, 7.2 or 7.3, wherein the composition is administered in a dose of a single drop per eye two times per day in a net volume of 20-24 μL.

7.6 The method of 7.4, wherein the composition is administered at a dose of a single drop per eye two times per day in a net volume of 20-22 μL, or a net volume of about 22 μL.

7.7 The method of 7.1 to 7.6, wherein the second dose is administered at least 1 hour after the first dose, or wherein the second dose is administered at least 2 hours after the first dose, or wherein the second dose is administered at least 3 hours after the first dose, or wherein the second dose is administered at least 4 hours after the first dose.

7.8 The method of 7.1 to 7.7, wherein the time interval between the first and second dose is administered is no more than about 8 hours, or no more than 12 hours.

7.9 The method of 7.1 to 7.8, wherein the patient has a history of keratoconjunctivitis sicca (dry eye disease), or keratoconjunctivitis sicca due to Meibomian gland dysfunction, or Meibomian gland dysfunction in one or both eyes for at least six months prior to treatment.

7.10 The method of 7.1 to 7.9, wherein the method comprises administering the composition over a period of at least 2 weeks, at least 4 weeks, or at least 8 weeks.

7.11 The method of 7.1 to 7.10, wherein the patient meets at least 2 of the criteria selected from the group consisting of:

i. a tear film breakup time (TFBUT) of 3.8 sec or lower (e.g. between 0 and 3.8 sec), ii. a total ocular surface disease index (OSDI) of 36 or higher (e.g. between 36 and 100), iii. a total corneal fluorescein staining (NEI scale) between 5 and 9;

iv. a Schirmer's Test I of 10 mm, or greater, v. a Meibomian gland dysfunction (MGD) score of 4, or higher (e.g. a score of between 4 and 15), and vi. a VAS severity of dryness score of higher than 50, e.g. between 50 and 100.

7.12 The method of 7.1 to 7.11, wherein the patient meets at least 2 of the criteria selected from the group consisting of:

i. a tear film breakup time (TFBUT) of between 2 and 3.8 sec, ii. a total ocular surface disease index (OSDI) of between 36 and 74, iii. a total corneal fluorescein staining (NEI scale) between 5 and 9, iv. a Schirmer's Test I of 10 mm, or greater, v. a Meibomian gland dysfunction (MGD) score of between 4 and 11; and vi. a VAS severity of dryness score of between 50 and 90.

7.13 The method of 7.11 or 7.12, wherein the patient has at least one eye which meets all of the criteria (i.e. signs of dry eye disease) (i), (iii), (iv), and (v).

7.14 The method of 7.11 or 7.12, wherein the patient meets all of the criteria of (i) to (vi).

7.15 The method of 7.11 or 7.12, wherein the patient is characterized by at least one criterion (i.e. relating to the signs of dry eye disease) selected from (i), (iii), (iv) and (v) and at least one criterion (i.e. relating to the symptoms of dry eye disease) selected from (ii) and (vi).

7.16 The method of 7.1 to 7.10, wherein the patient meets at least 2 of the criteria selected from the group consisting of:

i. a tear film breakup time (TFBUT) of 3.8 sec or lower (e.g. between 0 and 3.8 sec), ii. a total ocular surface disease index (OSDI) of 36 or higher (e.g. between 36 and 100), iii. a total corneal fluorescein staining (NEI scale) between 5 and 9;

iv. a Meibomian gland dysfunction (MGD) score of 4, or higher (e.g. a score of between 4 and 15)

v. a VAS severity of dryness score of higher than 50, e.g. between 50 and 100.

7.17 The method of 7.1 to 7.10, or 7.16, wherein the patient meets at least 2 of the criteria selected from the group consisting of:

i. a tear film breakup time (TFBUT) of between 2 and 3.8 sec, ii. a total ocular surface disease index (OSDI) of between 36 and 74), iii. a total corneal fluorescein staining (NEI scale) between 5 and 9;

iv. a Meibomian gland dysfunction (MGD) score of between 4 and 11, and v. a VAS severity of dryness score of between 50 and 90.

7.18 The method of 7.16 or 7.17, wherein the patient has at least one eye which meets all of the criteria (i.e. signs of dry eye disease) (i), (iii), and (iv).

7.19 The method of 7.16 or 7.17, wherein the patient meets all of the criteria of (i) to (vi).

7.20 The method of 7.16 or 7.17, wherein the patient is characterized by at least one criterion (i.e. relating to the signs of dry eye disease) selected from (i), (iii), (iv) and at least one criterion (i.e. relating to the symptoms of dry eye disease) selected from (ii) and (v).

7.21 The method of 7.1 to 7.20, wherein the total ocular surface disease index (OSDI) score is assessed on a scale of 1 to 100, with higher scores representing a greater disability of the patient.

7.22 The method of 7.1 to 7.21, wherein the patient has a condition of the cornea characterized by ocular surface damage in one or more regions of the cornea, for example, the total corneal region and/or the central corneal region and/or the nasal corneal region and/or the temporal corneal region.

7.23 The method of 7.1 to 7.22, wherein the treatment comprises the reduction of ocular surface damage in one or more regions of the cornea, for example, the total corneal region and/or the central corneal region and/or the nasal corneal region and/or the temporal corneal.

7.24 The method of 7.23 wherein the patient has a condition of the cornea characterized by ocular surface damage, and wherein the method of treatment comprises treating or reducing the ocular surface damage of:

i. the total and central corneal region;

ii. the total and nasal corneal region iii. the total and temporal corneal region iv. the central and nasal corneal region v. the central and temporal corneal region 7.25 The method of 7.1 to 7.24, wherein the method comprises treating or reducing the ocular surface damage of one or more corneal regions and/or treating or reducing one or more symptoms of dryness in a patient suffering from keratoconjunctivitis sicca (dry eye disease) due to Meibomian gland dysfunction and/or Meibomian gland dysfunction.

7.26 The method of 7.25, wherein the method comprises treating or reducing the ocular surface damage of one or more corneal regions, and treating or reducing one or more symptoms of dryness in a patient suffering from keratoconjunctivitis sicca (dry eye disease) due to Meibomian gland dysfunction.

7.27 The method of 7.26, wherein the ocular surface damage of one or more corneal regions is selected from (a) the total corneal region, (b) the central corneal region, (c) the nasal corneal region, (d) the temporal corneal region, and (e) any combination thereof.

7.28 The method of 7.22 to 7.27, wherein the ocular surface damage and/or reduction thereof is determined by corneal fluorescein staining, optionally wherein grading of the one or more corneal regions by fluorescein staining is conducted using the (National Eye Institute) NEI scale.

7.29 The method of 7.25 to 7.28, wherein the one or more symptoms of dryness are selected from (a) the severity of dryness (b) blurred vision, (c) sensitivity to light, (d) frequency of dryness; (e) awareness of dryness, and (d) any combination thereof.

7.30 The method of 7.29 wherein the symptoms (a) to (c) are determined on a visual analog scale (VAS) from 0% to 100% indicating the level of discomfort, and wherein the symptoms (d) and (e) are determined on a visual analog scale (VAS) from 0% to 100% indicating the percentage of time the dryness symptoms are experienced by the patient.

7.31 The method of 7.11 to 7.30, wherein the symptom of dryness and/or reduction thereof is graded using a total ocular surface disease index (OSDI) score.

7.32 The method of 7.31 wherein the total ocular surface disease index (OSDI) score is assessed on a scale of 1 to 100 with higher scores representing greater disability of the patient.

7.33 The method of 7.1 to 7.32, wherein the composition is effective in reducing the symptom severity of dryness within 2 weeks after start of treatment.

7.34 The method of 7.33, wherein the symptom severity of dryness is reduced by at least 25% in said patient.

7.35 The method of 7.1 to 7.34, wherein the patient has keratoconjunctivitis sicca (dry eye disease) selected from evaporative dry eye disease, or wherein the patient has keratoconjunctivitis sicca (dry eye disease) selected from evaporative dry eye disease, due to Meibomian gland dysfunction.

7.36 The method of 7.1 to 7.35, wherein the patient does not suffer from aqueous dry eye disease or aqueous tear-deficient dry eye disease 7.37 The method of 7.1 to 7.36, wherein treatment is performed for about at least 1 day, or for at least 5 days, or for at least 10 days, or for at least 30 days, or for at least 60, or for at least 90 days.

7.38 The method of 7.1 to 7.37, wherein the patient is a human patient.

7.39 The method of 7.38, wherein the patient is a female patient.

7.40 The method of 7.38, wherein the patient is a male patient.

7.41 The method of 7.39 or 7.40, wherein the patient is aged 20-80 years old at the time of treatment, e.g., 20-50 years old, or 20-70 years old, or 30-80 years old, or 30-50 years old, or 30-70 years old, or 40-80 years old, or 40-60 years old, or 40-70 years old, or 50-80 years old, or 50-70 years old.

7.42 The method of 7.1 to 7.41, wherein the patient suffers from a co-morbidity, for example, conjunctivitis, stye, chalazion, blepharitis, ectropion, eyelid laxity, eyelid edema, eyelid dermatitis, punctate keratopathy, or ocular allergies, or any combination thereof.

7.43 The method of 7.1 to 7.42, wherein the patient suffers from keratoconjunctivitis sicca which is caused by treatment of a co-morbidity, for example, treatment with any one or more of: isotretinoin, sedatives, diuretics, tricyclic antidepressants, antihypertensives, anticholinergics, oral contraceptives, antihistamine, nasal decongestants, beta-adrenergic antagonists, phenothiazines, atropine opiates (e.g., morphine), optionally wherein any such treatment is concurrent or previous, and further optionally, wherein any such treatment is systemic (e.g., oral or parenteral).

7.44 The method of 7.1 to 7.43, wherein the patient suffers from keratoconjunctivitis sicca which is caused by ocular surgical intervention, for example, corneal surgery, refractive surgery, LASIK surgery, cataract surgery, optionally wherein any such ocular surgery is concurrent or previous.

7.45 The method of 7.1 to 7.44, wherein the patient is concomitantly under treatment with another topical ophthalmic medication, for example, an antibiotic, anti-fungal, corticosteroid, immunosuppressant, sympathomimetic, anesthetic, antihistamine, or any combination thereof.

7.46 The method of 7.1 to 7.45, wherein the patient is a contact lens wearer.

7.47 The method of 7.1 to 7.46, wherein the patient was unresponsive or insufficiently response to previous treatment for keratoconjunctivitis sicca (dry eye disease).

7.48 The method of 7.47, wherein said previous treatment comprise one or more of the following treatment methods: topical aqueous immunosuppressant administration (e.g., topical aqueous ciclosporin), topical corticosteroid administration, or topical aqueous artificial tears administration.

In a further and related aspect to the aspect 7, the present disclosure also further provides for a method of treatment according to the following embodiments:

7.49 A method of treating keratoconjunctivitis sicca (dry eye disease), and/or treating keratoconjunctivitis sicca (dry eye disease) due to Meibomian gland dysfunction and/or treating Meibomian gland dysfunction and/or treating of a condition of the conjunctiva or cornea, or as defined in any one of the methods 7.1 to 7.41, wherein the method comprises administering an ophthalmic composition essentially consisting of 1-perfluorohexyloctane, or a composition as defined in any one of the compositions of 7.1 or 7.2, to a patient, wherein the composition is provided as a kit comprising:

a. an ophthalmic composition essentially consisting of 1-perfluorohexyloctane, or as defined in 7.1 or 7.2, and b. a container for holding the composition.

7.50 The method of 7.49, wherein the method is defined in accordance with any one of methods 7.1 to 7.48.

7.51 The method of 7.49, wherein the method comprises treating keratoconjunctivitis sicca (dry eye disease) due to Meibomian gland dysfunction and/or treating a condition of the cornea.

7.52 The method of 7.49 to 7.51, wherein the container is adapted to hold at least at least 600-720 µl of the composition.

7.53 The method of 7.49 to 7.52, wherein the container is adapted to hold an amount of composition supporting a two-times daily treatment for at least 30 days.

7.54 The method of 7.49 to 7.53, wherein the kit further comprises a drop dispenser adapted to dispense a drop of between 10-12 µl volume, or a drop of about 10 to 11 µl volume, or a drop of about 11 µl volume.

7.55 The method of 7.49 to 7.54, wherein the kit further comprises instructions for use, and wherein the instructions for use are in an readable or tangible form, preferably in printed form (e.g. provided in the form of a leaflet or insert of container label) or in any machine- or computer-readable form (e.g. a machine-readable label such as for example a barcode or QR code) indicating two-times per day administration of the composition daily, according to any one of the methods described in 7.1 to 7.48, or optionally, according to any one of the preceding methods method 4 or 4.1 to 4.61 or methods 5, or 5.1 to 5.59.

While semifluorinated alkanes have been described in the art, e.g. in EP-A 2 335 735, as useful carriers for ophthalmic drugs for the topical treatment of conditions such as keratoconjunctivitis sicca, the present invention is based on unexpected discovery that semifluorinated alkanes, when administered in the proper dosage regimes, can enrich certain ophthalmic tissues in semifluorinated alkane. It has been found that the semifluorinated alkane, even on administration topically to the surface of the cornea, or to the conjunctiva, localizes to, and enriches certain ophthalmic tissues, for example such as the Meibomian glands in the upper and/or lower eyelid. This results in the accumulation of semifluorinated alkane in such tissue(s), forming a "depot" which can release the semifluorinated alkane from the depot back onto the ocular surface, e.g. the cornea, or conjunctiva. The effect is one of delayed release of semifluorinated alkane from the ophthalmic tissue depot, resulting in maintenance of a therapeutically effective concentration of semifluorinated alkane between the administration of a dose of the ophthalmic composition comprising the semifluorinated alkane. In combination with the initial dose of ophthalmic composition, the effect is one of a sustained release of semifluorinated alkane which begins shortly after administration of an eye drop and continues until enriched ophthalmic tissue is depleted of its store of semifluorinated alkane, or alternatively, when a multiple or continuous dosing scheme is followed the ophthalmic tissue is newly enriched in the semifluorinated alkane with each administration of new dose of the ophthalmic composition, resulting in a continuous enrichment of the ophthalmic tissue in the semifluorinated alkane.

The present disclosure is also based on the finding that the compositions comprising semifluorinated alkane may be administered in a dosage regime of less than four times daily. A four-times daily dose application of a single drop of 10-11 μl per eye has been considered to be efficacious as a standard treatment regimen. For example, in the instructions for administration, accompanying a product composition of F6H8, subjects are instructed to administer a drop of the composition of F6H8, four times a day, unless recommended otherwise by a physician. Surprisingly, it has been found that a reduced dosing frequency may also provide similar therapeutic outcome. Unexpectedly, it has also been found that with a reduced dosing frequency of two times a day, the degree of severity in terms of dryness, as a symptom experienced by dry eye patients, may be significantly reduced already two weeks after the commencement of treatment under this regimen.

In an embodiment of the present disclosure, the compositions for use according to the invention may be administered over a treatment period of at least 2 weeks, or of at least 4 weeks, or at least 8 weeks. In another embodiment, the pharmaceutical compositions for use in the treatment of the dry eye disease conditions and disorders as described herein may be administered on a continuous basis while dry eye disease symptoms, or signs such as ocular surface damage persist, as determined by any one of the methods described herein.

The reduction in amount of the composition comprising a semifluorinated alkane to be administered is not only economically beneficial, but may also have the effect, due to reduced exposure to the compound, of reducing the likelihood of occurrence, if any, of any adverse events which patients may develop while receiving the treatment. The reduced dosing frequency of 2 times daily (BID) in contrast to a four-time daily dosing regimen would also be more convenient for the patient, and thus may increase likelihood of patient compliance. Further, the BID treatment may be convenient for patients, where the signs and/or symptoms of dry eye disease and or dry eye disease due to Meibomian gland dysfunction have already ameliorated to such extent that more frequent dosing of the composition is not required.

Keratoconjunctivitis sicca is a complex, multifaceted disease or condition as described above. It is also known as dry eye syndrome, dry eye disease (DED), or dysfunctional tear syndrome. Aqueous-deficient DED, evaporative DED are within the scope of keratoconjunctivitis sicca and form specific subtypes thereof. Sjögren syndrome, lacrimal gland insufficiency, Meibomian gland disease and Meibomian gland dysfunction, and other conditions are also within the scope of keratoconjunctivitis sicca, being direct or indirect causes thereof.

Meibomian gland diseases cover a broad range of Meibomian gland disorders including neoplasia and congenital disorders. Meibomian gland dysfunction, on the other hand is understood to be abnormalities of the Meibomian glands which are often characterized by gland duct obstructions and/or changes (qualitative and/or quantitative) to the secretions of the glands. In general, conditions or disease states causing or leading to an abnormal, reduced or increased delivery of lipids to the tear film can give rise to keratoconjunctivitis sicca and the symptoms associated therewith.

Symptoms of keratoconjunctivitis sicca include a dry, scratchy, gritty, or sandy feeling in the eye; foreign body sensation; pain or soreness; stinging or burning; itching; increased blinking; eye fatigue; photophobia; blurry vision; redness; mucus discharge; contact lens intolerance; excessive reflex tearing. In addition to the symptoms of keratoconjunctivitis sicca as described, patients with Meibomian gland dysfunction may also experience symptoms including itchiness, redness, swelling, pain or soreness, discharge accumulation or crusting specifically at the lid margins. It is understood that not all patients suffering from keratoconjunctivitis sicca exhibit all symptoms simultaneously. Hence, there is currently no uniform set of criteria for diagnosing the disease. It is also understood that patients may suffer from one or more subtypes of keratoconjunctivitis sicca, or one or more conditions or disease pathways causing keratoconjunctivitis sicca. It is however important to note that, within the scope of the present invention, any of the aspects, symptoms or pathophysiological consequences of dry eye disease may be addressed.

Semifluorinated alkanes are linear or branched alkanes some of whose hydrogen atoms have been replaced by fluorine. The semifluorinated alkanes (SFAs) used in the present invention are composed of at least one non-fluorinated hydrocarbon segment and at least one perfluorinated hydrocarbon segment and are according to the general formula $F(CF_2)_n(CH_2)_mH$. Another nomenclature which may be used herein refers to the above-mentioned SFAs having two as RFRH, wherein RF designates a perfluorinated hydrocarbon segment, RH designates a non-fluorinated segment. Alternatively, the compounds may be referred to as FnHm, wherein F means a perfluorinated hydrocarbon segment, H means a non-fluorinated segment, and n, and m is the number of carbon atoms of the respective segment. For example, F6H8 is used for 1-perfluorohexyloctane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

In some embodiments, the compositions comprising a semifluorinated alkane, as defined in the context of the present disclosure are free of active ingredient, or are drug-free compositions, i.e. free of any pharmaceutically active drug substance useful for ophthalmic treatment. In particular embodiments, the compositions are free of, or exclude a therapeutically effective amount of any active ingredient, or pharmaceutically active drug substance, that is, for example, useful for ophthalmic treatment. As used herein, active ingredient refers to any type of pharmaceutically active compound or derivative that is useful in the prevention, diagnosis, stabilization, treatment, or, generally speaking. management of a condition or disease. Therapeutically effective amount refers to a dose, concentration or strength which is useful for producing a desired pharmacological effect. As used herein, a composition according to the present disclosure which is "free of an active ingredient", or is "free of a drug substance", or "free of any pharmaceutically active drug substance useful for ophthalmic treatment," or similar variations thereof, is a composition which comprises at least one or more semifluorinated alkanes, but does not include any other pharmaceutically active ingredient or drug substance which, e.g. may be useful or active for ophthalmic treatments.

In some embodiments, the SFAs of the invention are those of formula $F(CF_2)_n(CH_2)_mH$, in particular, SFAs of the formula $F(CF_2)_4(CH_2)_5H$, $F(CF_2)_4(CH_2)_6H$, $F(CF_2)_6(CH_2)_6H$, $F(CF_2)_6(CH_2)_8H$, and $F(CF_2)_8(CH_2)_8H$. In particular embodiments the SFA is $F(CF_2)_6(CH_2)_8H$.

In other embodiments, the composition according to the invention may consist of the semifluorinated alkane 1-perfluorohexyloctane, and optionally, up to 3 wt % of 2-perfluorohexyloctane, based on the total weight of the composition. 2-perfluorohexyloctane is a semifluorinated alkane with the formula $F(CF_2)_6$—$CH(CH_3)$—$(CH_2)_6H$. In further embodiments, the composition may consist of 1-perfluorohexyloctane, and up to 2 wt % of 2-perfluorohexyloctane, or up to 1 wt % of 2-perfluorohexyloctane. In other embodiments, the composition of the invention may essentially consist only of the semifluorinated alkane $F(CF_2)_6(CH_2)_8H$.

As used herein, the term wt % refers to the weight of a component as a percentage fraction of the weight of the composition determined as a whole. The term about preceding a parameter, such as wt % includes the precise value as well as any value falling within the degree of variability usually observed in the measurement and determination of the parameter, including standard techniques and equipment known in the field.

In some embodiments, the composition may further comprise a second SFA which is an SFA of the formula $F(CF_2)_n(CH_2)_mH$, wherein n is an integer from the range of 4 to 8 and m is an integer from the range of 5 to 10 include, in particular, $F(CF_2)_4(CH_2)_5H$, $F(CF_2)_4(CH_2)_6H$, $F(CF_2)_6(CH_2)_6H$, $F(CF_2)_6(CH_2)_8H$, $F(CF_2)_6(CH_2)_{10}H$, $F(CF_2)_8(CH_2)_8H$ and $F(CF_2)_8(CH_2)_{10}H$. In embodiments comprising two SFAs, the SFAs may be present in a weight ratio of at least about 3:1, for example, at least about 50:1 or at least about 30:1, or at least about 10:1.

Liquid SFAs are chemically and physiologically inert, colourless and stable. Their typical densities range from 1.1 to 1.7 $g/cm^3$ (e.g. the density of F6H8 is 1.35 $g/cm^3$), and their surface tension may be as low as 19 mN/m. SFAs of the $F(CF_2)_n(CH_2)_mH$ type are insoluble in water but also somewhat amphiphilic, with increasing lipophilicity correlating with an increasing size of the non-fluorinated segment.

Liquid SFAs of the RFRH type are being used commercially for unfolding and reapplying a retina, for long-term tamponade as vitreous humour substitute (H. Meinert et al., European Journal of Ophthalmology, Vol. 10(3), pp. 189-197, 2000), and as wash-out solutions for residual silicon oil after vitreo-retinal surgery. Experimentally, they have also been used as blood substitutes (H. Meinert et al., Biomaterials, Artificial Cells, and Immobilization Biotechnology, Vol. 21(5), pp. 583-95, 1993). These applications have established SFA's as physiologically well tolerated compounds.

SFAs are well-tolerated by the eye, as shown in preclinical testing. In comparison, organic or non-aqueous solvents, perhaps with the exception of oily compounds, are typically very irritating or even highly damaging when administered topically to an eye.

Moreover, compared to oily carriers or vehicles in ophthalmic compositions for topical use, SFAs exhibit a refractive index in the region of 1.29 to 1.35, which is much better compatible with the aim of a minimally affected vision thus causing little or no blurring.

SFA compositions of the present invention have several useful functional effects when administered to the eye. Semifluorinated alkanes are able to mix and/or dissolve well with non-polar and lipophilic substances. It is proposed that the SFAs as defined in the context of the present invention, e.g., SFAs selected from $F(CF_2)_4(CH_2)_5H$ (F4H5), $F(CF_2)_4(CH_2)_6H$ (F4H6), $F(CF_2)_6(CH_2)_6H$ (F6H6), $F(CF_2)_6(CH_2)_8H$ (F6H8), and $F(CF_2)_8(CH_2)_8H$ (F8H8), for example, F4H5 or F6H8, or F6H8, may be particularly useful for solubilizing meibum lipids and for removing abnormal and obstructive meibum found in clogged Meibomian gland ducts.

Meibum is the lipid secretion of the Meibomian gland ducts and is normally secreted as a clear fluid comprising a complex mixture of polar and non-polar lipids such as cholesterol and wax esters, acyl glycerides, free fatty acids and phospholipids. In their dysfunctional state, the glands producing meibum may express secretions with an altered composition of those lipids which exhibit increased viscosity and which may also contain particulate cellular material. Such secretions can obstruct the gland ducts and may be ineffective for forming a functional stable and continuous tear film lipid layer, leading to lipid tear film deficiency, and the condition and symptoms of keratoconjunctivitis sicca. Ophthalmic compositions comprising a semifluorinated of the formula $F(CF_2)_n(CH_2)_mH$, as defined in the context of the present invention are effective in solubilizing meibum, and in particular, in solubilizing the abnormal (e.g., viscous) meibum obstructing the Meibomian glands and/or Meibomian gland ducts.

In addition, the ophthalmic compositions of the present invention can also serve as either a replacement, substitute or supplement to the tear film lipid layer. For patients suffering from dry eye syndrome, the SFA compositions of the present invention may have a lubricating as well as a protective effect. It is believed that the SFA compositions are capable of forming a protective film over the corneal surface and prevent aqueous evaporative loss of the tear film.

In one embodiment, the ophthalmic SFA compositions as defined in the present disclosure may serve as a replacement, substitute or supplement to the tear film lipid layer, e.g. as a lubricant and/or form a protective film, and also effective for effective in solubilizing meibum, and in particular, in solubilizing the abnormal (e.g., viscous) meibum obstructing the Meibomian glands and/or Meibomian gland ducts.

Moreover, SFAs exhibit a remarkable wetting and spreading behaviour by which they can rapidly and effectively spread over the corneal surface and conjunctiva. This remarkable wetting and spreading behaviour permits the SFA to spread away from the administered eye drop rapidly and completely, further permitting the SFA to access the Meibomian gland ducts on the upper and/or lower eyelids. The SFA, due to its high solubilizing capacity, can penetrate the meibum plugs which are prevalent in Meibomian gland dysfunction (MGD) or disease, resulting in solubilization and removal of the plugs, restoring proper Meibomian gland function.

Wetting means the ability of a liquid to establish and maintain contact with a solid surface, resulting from inter-molecular interactions when the two are brought together. The balance between adhesive and cohesive forces deter-mines the degree of wetting. The higher the adhesive forces compared to the cohesive forces, the more a drop of liquid will spread across the surface of the solid material. Con-versely, very high cohesive forces within the liquid will cause the drop to form a sphere, thus avoiding contact with the surface. Similarly, spreading may also occur at the interface of two liquids which are brought into contact with each other.

A measure for wetting and spreading is the contact angle θ. The contact angle is the angle at which the liquid-vapour interface meets the solid-liquid or liquid-liquid interface. The tendency of a drop to spread out increases as the contact angle decreases. Thus, the contact angle provides an inverse measure of wettability.

A low contact angle of less than 90° indicates high wettability and/or spreading, whereas a higher contact angle indicates poor wettability and spreading. Perfect wetting and spreading results in a contact angle of 0°, also reported as no measurable contact angle.

The enhanced spreading behavior and stable film proper-ties of such ophthalmic compositions comprising SFAs are particularly advantageous for treating the dry eye condition. A droplet administered to the surface of the eye may lead to rapid spreading of the SFA mixture compositions over the corneal surface and the formation of a film. A stable film that does not immediately break up provides a longer-lasting lubricating effect on the ocular surface. Efficient spreading allows for a more effective distribution of the SFA not only over the ocular surface, but also to more distant ocular tissues such as the Meibomian glands or the lacrimal glands.

One result of this is a significantly reduced reliance placed on the blinking mechanism of the patient (which may be ineffective or hindered by the diseased state) to spread the composition over the ocular surface. It is believed that the compositions of the invention may thus be more efficiently administered to the ocular surface, in comparison with conventional formulations which are generally aqueous based and have poorer spreading behavior. As such, less frequent administration to the dry eye for relief may be achieved with these compositions.

In particular, the compositions of the invention as described in the above embodiments may be used for the treatment of patients who are non-responsive to traditional physical methods of treating Meibomian gland dysfunction, or dry eye disease caused, or exacerbated by Meibomian gland dysfunction, such as physical or forced expression of meibum or meibum obstructions from the Meibomian glands, application of heat compresses, e.g. to the eyelids (heat therapy), simultaneous physical expression and heat therapy, lid scrubs, or intraductal probing of the meibomian gland orifices. Non-responsive to treatment may refer to a continued condition of, a progression, or a recurrence of meibomian gland dysfunction and symptoms associated thereof in a patient, despite a prescribed or recommended period of treatment, e.g. using the traditional methods of treatment. The use of the present compositions and methods of treatments according to the invention may be used to replace such therapy, or also as an alternative therapy to such traditional methods, which often may need to be performed at a doctor's office and which are not as convenient and/or poorly tolerated due to pain during the application of these physical methods.

In another aspect, the compositions for the invention may be used for the treatment of conditions such described in the above embodiments, wherein the patient is non-responsive to treatment with aqueous ophthalmic eye drop composi-tions. In particular, the compositions may be used for the treatment of patients suffering from meibomian gland dys-function and who are non-responsive to treatment with aqueous-based ophthalmic eye drop compositions e.g. emul-sions, or aqueous solutions such as tear supplements or tear substitutes, and who may still have a continuing condition of, a progression of or a recurrence of dry eye disease or MGD, or symptoms thereof, despite a course of therapy with such compositions.

Another advantage of using ophthalmic compositions comprising SFA is that SFAs are capable of forming very small droplets, for example, of about 10-11 µl volume, when dispensed from a conventional dropper such as a conven-tional eye dropper. A drop volume of F6H8 of about 10-11 µl translates to a single dose of 13.5-14.85 mg (with F6H8 density=1.35 g/ml). Without wishing to be bound by theory, it is believed that the small droplet size is a result of an interplay of the SFA's unique properties in terms of their density, viscosity, and surface tension. It is believed that for topical administration into an eye a small drop or volume of administration is highly advantageous as the capability of the lacrimal sac to accept and hold fluid is extremely limited. In fact, it is very common that the administration of a conventional eye drop formulation based on water or oil immediately leads to a discharge of a substantial fraction of the administered medicine as well as some tear fluid. At the same time, there is a risk that some of the administered dose will be taken up systemically via the nasolacrimal duct.

The invention also provides a means of formulating non-aqueous ophthalmic compositions which are microbio-logically stable. Aqueous ophthalmic compositions are prone to bacterial contamination. In comparison, SFAs have bacteriostatic properties and do not support microbial growth. Hence, it is possible to formulate preservative-free ophthalmic compositions which are better tolerable for many patients, in particular patients suffering from kerato-conjunctivitis sicca. Such compositions also do not promote bacterial infection of the eye lid margin in patients who, for example, are suffering from obstructed or blocked Mei-bomian glands.

Ophthalmic tissue includes any surface of the eye anatomy that is, or can be (i.e. by non-surgical means) topically exposed. Optionally, the compositions are admin-istered as a single drop to either the cornea or conjunctiva. Ophthalmic tissue includes, but is not limited to, cornea, conjunctiva (bulbar and palpebral), lacrimal glands (includ-ing lacrimal ducts and lacrimal sacs), the Meibomian glands, and the sclera.

In some embodiments, the compositions of the invention can be used to alleviate or relieve ocular symptoms associ-ated ophthalmic disorders or conditions, including kerato-conjunctivitis sicca and Meibomian gland dysfunction. For example, they may be used in addition to medicines com-prising an active ingredient whose dosing frequency is typically limited by tolerability or safety concerns. The compositions for alleviating or relieving any non-disease related sensation of dryness, irritation, or discomfort of the eye. Said compositions may be used concomitantly or in conjunction with eye compositions with pharmaceutically active ingredients (e.g. immunosuppressant eye drops) that are aimed at curing or treating the root causative pathways of an ophthalmic disease.

In some embodiments, the compositions of the invention may be used as a cleansing solution for the eye or ophthalmic tissue. The compositions are used to cleanse or help remove or wash away any accumulated debris or discharge such as meibum secretions from the eye lid, eye lid margins, eye lashes, or eye crevices. Compared to aqueous formulations, the SFA compositions are able to spread more readily, and thus are able to reach the more difficult to access regions of eye lid anatomy. In a particular embodiment, the compositions for use as a cleansing solution are formulated to be administered as a spray. This can be useful for patients either averse to, or unable to apply the compositions via eye drops.

Optionally the compositions of the invention are highly stable, water-free, preservative-free.

Optionally, one or more further excipients may be used in the SFA compositions. Additional excipients may also, in addition to the SFAs serve to contribute to the deficient tear film and tear film lipid layer in patients with keratoconjunctivitis sicca, related conditions, and symptoms associated therewith. In some embodiments, excipients are biocompatible and are tolerated by the eye, and are liquid and/or soluble and miscible in SFAs. In particular, excipients are optionally selected from lipids, oils, lipophilic vitamins, lubricants, viscosity agents, antioxidants surfactants and mixtures of two or more thereof.

In some embodiments, the composition may also comprise further excipients as required or useful such as acids, bases, electrolytes, buffers, solutes, antioxidants, stabilisers, synergists, and—if required in a particular case—a preservative. The compositions may be formulated to be administered as a liquid solution, gel, or a spray.

They may be prepared by commonly known techniques for the manufacture of said liquid solutions, gels, or sprays.

As used herein, the term "enrichment" refers to the temporary storage of SFA in an ophthalmic tissue which is administered and delivered as a topical ophthalmic composition, without regard to whether the tissue in question previously retained or stored any SFA. Tissues which may be enriched in SFA optionally include the conjunctiva, cornea, lacrimal glands and/or Meibomian glands. As used herein, the weight percent enrichment of the tissue with SFA refers to the weight of SFA measured in a tissue with respect to the total weight of the tissue.

Enrichment of a tissue in SFA is a condition dependent both on the nature of the composition administered, the nature of the tissue to which the composition is administered, and particularly, to the nature of the dosing regimen used to administer the composition. The skilled artisan would recognize that the prior art would not make it obvious that the administration of a liquid topical ophthalmic composition comprising a semifluorinated alkane would result in enrichment of any ophthalmic tissue in such semifluorinated alkane. For example, without being bound by theory, it is expected that if dosing of the ophthalmic composition is too infrequent or too low in volume, insufficient SFA would be delivered to the eye to result in enrichment of an ophthalmic tissue. In addition, other components of the composition, such as surfactants or water, might affect the ability of the SFA to partition into and enrich specific ophthalmic tissues. Furthermore, too large a dose (e.g., too large droplets, for example, with drop volumes greater than 30 µl) could result in unnecessary blinking that could diminish the ability of the SFA to enrich an ophthalmic tissue.

The skilled artisan would also recognize that liquid topical ophthalmic compositions generally have a short residence time in the eye. The glands around the eye continually generate tears and oils that are continually washed off of the cornea via the lacrimal apparatus. Mechanical agitation and blinking may further diminish the residence time of such compositions in contact with ophthalmic tissues. It is for this reason that many common topical ophthalmic treatments require administration many times each day. The enrichment of an ophthalmic tissue by an ophthalmic composition to a sufficient extent to provide continual, delayed release of the active component of the composition back into the surface of the eye alleviates this problem.

All patents, publications, and other references described herein are hereby incorporated by reference in their entireties.

EXAMPLES

Example 1: Pharmacokinetics and Distribution of $^{14}$C—F6H8 Following Topical Ocular Administration to Rabbits The study is conducted to assess the ocular tissue distribution after topical ocular administration of $^{14}$C-1-Perfluorohexyloctane (F6H8, NovaTears®) to Dutch Belted (pigmented) female rabbits.

On the first day of dosing, 5.474 mL of $^{14}$C—F6H8 is combined with 9.526 mL of F6H8. The dose formulation is magnetically stirred and appears to be a colorless solution. The dose formulation is separated into vials to provide one vial per day for dose administration and it is stored at approximately −20° C. One vial per day is thawed prior to dose administration. In between dose administrations, the vial is capped and stored at approximately 5° C. when not in use.

Duplicate weighed aliquots are taken from the dose formulation prior to and following dose administration on Days 1 and 5, and are analyzed by liquid scintillation counting (LSC) to determine the concentration of radioactivity and homogeneity.

Stability of the test article under conditions of administration is demonstrated by analysing pre-dose and post-dose aliquots by HPLC.

Animals are not fasted prior to dose administration. All animals receive single 35 µL-drops of the dose formulation in each eye, with the right eye dosed first. All collection times are based on the time of dosing of the second (left) eye for the last dose, as applicable.

The topical ocular dose is administered to the central or superior part of the cornea via a positive displacement micropipette and allowed to spread across the surface of the eye. After the dose is administered, the eye is allowed to close naturally. Each animal is then restrained for approximately 1 minute to prevent rubbing of the eyes.

Tears and Ocular Tissue Collection: Tears are collected from two animals per group per time point at 0.25, 0.5, 1, 2, 4, 8, and 24 hours post-dose following the single dose or the last dose of the multiple dose scheme. Tears are collected using Tear Flo Test (TFT) strips that were dye free. One strip of paper is used for each eye for each time point. Following collection, the tube containing the strip is placed on dry ice or stored at approximately −70° C. until analysed.

At the time of sacrifice, both eyes are enucleated and ocular tissues including Aqueous humour, Conjunctiva (bulbar), Conjunctiva (palpebral), Lacrimal gland (accessory), Lacrimal gland (main), Meibomian glands (tarsal plate), Choroid-Retinal pigmented epithelium (Choroid-RPE), Cornea, Iris-ciliary body (ICB), Retina, Sclera (anterior), Sclera (posterior), Vitreous humour are collected.

Radioanalysis: All samples are analyzed for radioactivity in a Model 2900TR liquid scintillation counter (Packard Instrument Company) for at least 5 minutes or 100,000 counts, utilizing Ultima Gold XR or Hionic Fluor scintillation cocktails (Perkin Elmer). Each sample is homogenized before radioanalysis, unless the entire sample is used for analysis. All samples are analyzed in duplicate if sample size allows.

For Conjunctiva (bulbar and palpebral), Cornea, Lacrimal gland (main), Meibomian glands, Retina, and Sclera (anterior and posterior), each sample is digested in 2M sodium hydroxide in ethanol (80:20, v:v) and maintained at room temperature or in an oven set no higher than 30° C. until dissolved. Scintillation cocktail is added, and the samples are shaken and analyzed directly by LSC.

For Lacrimal gland (accessory), each sample is digested in 2M sodium hydroxide in ethanol (80:20, v:v) and maintained at room temperature or in an oven set no higher than 30° C. until dissolved. The sample is homogenized by mixing and duplicate weighed aliquots are analyzed directly by LSC.

For Tears, at least 10 mL of Ultima Gold XR scintillation cocktail is added, and the samples are shaken and analyzed by LSC.

Quantitative Autoradiography: Animals are euthanized with sodium pentobarbital and blood is collected via cardiac puncture. Immediately after blood collection, the animals were frozen for quantitative autoradiography. The frozen heads are embedded in chilled carboxymethyl cellulose and frozen into blocks. Appropriate sections are collected on adhesive tape at 40 mm thickness, in a Leica CM 3600 cryomicrotome. Mounted sections are exposed for 4 days on phosphor imaging screens along with fortified blood standards for subsequent calibration of the image analysis software and subsequently scanned using a Typhoon scanner. The autoradiographic standard image data are sampled using InterFocus Imaging Ltd. MCID™ Analysis software to create a calibrated standard curve. Specified tissues and fluids are analysed. Tissue concentrations are interpolated from each standard curve as nanocuries/g and then converted to ng equivalents/g on the basis of the test article specific activity.

Single topical ocular administration, radioanalysis of ocular tissues: The rabbits received a single topical ocular administration in both eyes. The target dose level is 45.6 mg/eye (25 μCi/eye). Following the single topical ocular dose of 35 μl of $^{14}C$—F6H8, two animals per time point are sacrificed at 0.25, 0.5, 1, 2, 4, 8, and 24 hours post-dose in a sparse sampling profile. Ocular tissues (including tears collected prior to sacrifice) are collected from all animals at sacrifice.

TABLE 1

Mean concentrations of radioactivity in ocular tissues (conjunctiva bulbar, conjunctiva palpebral, cornea, sclera anterior, meibomian glands, lacrimal gland accessory, lacrimal gland main, tears) determined by liquid scintillation counting at specified times after a single topical ocular administration of $^{14}C$-F6H8 to female Dutch Belted rabbits:

| | Single Dose ng Equivalents $^{14}C$-F6H8/g Hours | | | | | | |
|---|---|---|---|---|---|---|---|
| | 0.25 | 0.5 | 1 | 2 | 4 | 8 | 24 |
| Conjunctiva (bulbar) | 5450 | 3680 | 3320 | 3050 | 1610 | 1340 | 1090 |
| Conjunctiva (palpebral) | 14200 | 5180 | 5700 | 4230 | 2500 | 1790 | 2270 |
| Cornea | 2040 | 8230 | 6110 | 3230 | 4480 | 6080 | 2730 |
| Lacrimal gland (accessory) | 577 | 0.00 | 255 | 1450 | 4280 | 2110 | 1500 |
| Lacrimal gland (main) | 1670 | 2770 | 641 | 1530 | 4130 | 2120 | 1810 |
| Meibomian glands | 294000 | 102000 | 57600 | 69200 | 29100 | 21100 | 14700 |
| Sclera (anterior) | 1140 | 2270 | 1300 | 767 | 1170 | 1330 | 611 |
| Tears | 2390000 | 995000 | 444000 | 700000 | 207000 | 6660 | 1300 |

The highest concentrations of substance-related $^{14}C$—F6H8 in ocular tissues of female Dutch Belted rabbits (as determined by radioanalysis) are observed in the anterior section of the eye. The highest mean concentrations (>1000 ng equivalents $^{14}C$—F6H8/g) are in the order of tears (2390000)>Meibomian glands (294000)>palpebral conjunctiva (14200)>cornea (8230)>bulbar conjunctiva (5450)>accessory lacrimal gland (4280)>main lacrimal gland (4130)>anterior sclera (2270) between 0.25 and 4 hours post-dose. Concentrations declined over time, especially within 8 hours post-dose in all of these tissues with background levels still detectable at 24 hours post-dose. Low levels of radioactivity are observed in the vitreous humour and retina, indicating some minor distribution of substance-related $^{14}C$—F6H8 into these tissues. No radioactivity is detected in the iris-ciliary body and choroid-RPE. By far, the highest exposure of substance-related $^{14}C$—F6H8 is observed in tears, Meibomian glands, and the anterior tissues.

Single topical ocular administration, quantitative autoradiography of ocular tissues: Analysis of the whole head by autoradiography following a single topical ocular administration of 35 μl of $^{14}C$—F6H8 to female Dutch Belted rabbits shows comparable distribution into ocular tissues as observed after radioanalysis. The highest concentrations (>10000 ng equivalents $^{14}C$—F6H8/g) are found in the anterior tissues in the order eyelid margin (443000)>internal eyelid (171000)>cornea (33500). Other tissues with high concentrations are the external eyelid skin, nasolacrimal duct, and nasal turbinates.

Multiple topical ocular administration: The rabbits receive twice daily doses (approximately 12 hours apart±20 minutes) of 35 μl $^{14}C$—F6H8 administered to both eyes for four consecutive days, and on the fifth day receive a single dose in the morning to both eyes (a total of nine doses). The administered dose level at each dosing occasion is approximately 47 mg/eye, equivalent to 29 mCi/eye. Following the last dose on Study Day 5, two animals per time point are sacrificed at 0.25, 0.5, 1, 2, 4, 8, and 24 hours post-dose in a sparse sampling profile. Ocular tissues (including tears collected prior to sacrifice) are collected from all animals at sacrifice.

TABLE 2

Mean concentrations of radioactivity in ocular tissues (conjunctiva bulbar, conjunctiva palpebral, cornea, sclera anterior, meibomian glands, lacrimal gland accessory, lacrimal gland main, tears) determined by liquid scintillation counting at specified times after multiple topical ocular administration of $^{14}$C-F6H8 to female Dutch Belted rabbits:

| | Multiple Dose ng Equivalents $^{14}$C-F6H8/g Hours | | | | | | |
| | 0.25 | 0.5 | 1 | 2 | 4 | 8 | 24 |
|---|---|---|---|---|---|---|---|
| Conjunctiva (bulbar) | 8290 | 5280 | 4440 | 3970 | 3840 | 2970 | 2750 |
| Conjunctiva (palpebral) | 14000 | 11900 | 11300 | 7510 | 6920 | 5160 | 4410 |
| Cornea | 20600 | 21000 | 27600 | 15900 | 17500 | 22000 | 16200 |
| Lacrimal gland (accessory) | 7120 | 8190 | 4770 | 5140 | 9280 | 5100 | 3480 |
| Lacrimal gland (main) | 7090 | 8140 | 4610 | 5040 | 8890 | 4650 | 3630 |
| Meibomian glands | 222000 | 145000 | 92900 | 100000 | 70300 | 52900 | 45500 |
| Sclera (anterior) | 3550 | 2650 | 3920 | 2080 | 3470 | 2650 | 2410 |
| Tears | 2330000 | 872000 | 742000 | 832000 | 103000 | 32200 | 46800 |

Following multiple topical ocular administration of 35 µl $^{14}$C—F6H8, the highest concentrations in ocular tissues are again observed in the tears, Meibomian glands, bulbar and palpebral conjunctiva, and cornea, showing that exposure and distribution of substance-related $^{14}$C—F6H8 mostly occurs in the anterior section of the eye. The concentrations declined over time, especially within 8 hours post-dose in all of these tissues, but were still detectable at 24 hours post-dose. The highest mean concentrations (>5000 ng equivalents $^{14}$C—F6H8/g) are in the order of tears (2330000)>Meibomian glands (222000)>cornea (27600)>palpebral conjunctiva (14000)>accessory lacrimal gland (9280)>main lacrimal gland (8890)>bulbar conjunctiva (8290) and are observed between 0.25 and 4 hours post-dose. Herein, higher concentrations of $^{14}$C—F6H8 were detected with the multiple topical ocular administration scheme as compared to single topical ocular administration.

Example 2

The study is conducted to evaluate the influence of 1-perfluorohexyl-octane (F6H8, NovaTears®) on tear film thickness in patients with mild to moderate dry eye disease. Herein the administration of 1-perfluorohexyl-octane is compared to Hydrabak (0.9% sodium chloride, Laboratoires Théa).

48 patients (safety population) are randomized (1:1 ratio) to receive either F6H8 or Hydrabak. One drop of F6H8 (droplet volume=10-11 µl) or Hydrabak is instilled in each eye 4 times daily for 30 days. DED relevant clinical measures are recorded at Visit 1 (day 0, baseline), Visit 2 (15±2 days) and Visit 3 (30±3 days). The primary outcome variable includes Tear film thickness (TFT) as measured with high resolution optical coherence tomography (OCT), while secondary outcome variables comprised Lipid Layer Thickness (LLT) of the tear film (with LipiView Interferometer), Non-Invasive Tear Break Up Time (NITFBUT) with Bon Antares Tear Film Topographer, Dynamic Meibomian Gland Imaging (DMI) with LipiView Interferometer, Blink frequency (with LipiView interferometer), Dry Eye Visual Analogue Scale (VAS), Corneal fluorescein staining, Conjunctival lissamine green staining, Schirmer I test, Tear Film Break Up Time (TFBUT), Ocular Surface Disease Index (OSDI), Adverse Events (AEs) and others.

The study meets its primary objective by demonstrating that F6H8 increases tear film thickness (TFT) over saline solution (Hydrabak) in patients with DED. The primary MMRM analysis demonstrates that the relative change (%) in Tear film thickness from baseline is significantly higher with F6H8 than with Hydrabak for the 48 subjects of the safety population.

After a single dose on Visit 1, F6H8 temporarily increased Tear film thickness (TFT) immediately after drop instillation (see Table 3).

TABLE 3

Tear film thickness (TFT) measurements based on relative change to baseline pre-dose measurements after a single dose on Visit 1 of the study comparing F6H8 to Hydrabak. Tear film thickness (TFT) is observed to increase immediately after drop instillation (i.e. 10 min), demonstrating a pronounced early onset of action.

| | Tear Film Thickness at study start (relative change from baseline in %) | |
| timepoint | NovaTears | Hydrabak |
|---|---|---|
| 10 min | 13.39% | 6.98% |
| 20 min | 6.63% | 7.08% |
| 40 min | 4.64% | 5.15% |
| 60 min | 4.03% | 5.04% |
| 120 min | 4.76% | 3.53% |
| 240 min | 3.28% | 3.15% |

After multiple dosing, F6H8 gradually increased Tear film thickness over time with a maximum effect at the end of the study after 4 weeks treatment (Visit 3), which is in line with the mode of action of F6H8 preventing evaporation by supporting the lipid layer. This potential sustained effect was confirmed by the least squares mean differences estimated per visit from the primary efficacy mixed model repeated measurement analysis (MMRM) calculated in a post-hoc analysis. These estimates show more pronounced and gradual thickening of tear films with F6H8 during the study, with 1.29% at Visit 1, 4.33% at Visit 2, and reached significance with 6.42% at Visit 3 for the 48 subjects of the safety population.

TABLE 4

Tear film thickness (TFT) measurements based on relative change compared to baseline pre-dose measurements after multiple dosing of F6H8 compared to Hydrabak. TFT was observed to gradually increase over time with a maximum effect at the end of the study after a period of 4 weeks treatment (Visit 3). The relative change compared to baseline pre-dose measurements is significantly pronounced, compared to those observed for Hydrabak.

Tear Film Thickness
after continuous dosing 4-times daily
(relative change from baseline in %)

| | 2 weeks | | 4 weeks | |
|---|---|---|---|---|
| timepoint | NovaTears | Hydrabak | NovaTears | Hydrabak |
| before | 1.43% | −0.80% | 3.22% | −1.48% |
| 10 min | 8.71% | 3.67% | 9.12% | 1.97% |
| 20 min | 8.57% | 4.28% | 10.35% | 3.09% |

The increased pre-dose Lipid Layer Thickness (LLT) at Visit 2 and 3 in the F6H8 group further substantiates the overall improvement of the tear film in patients with DED. The post hoc MMRM analysis on values recorded before instillation demonstrates that the relative change (%) in LLT from baseline is significantly higher for F6H8 than for Hydrabak, the estimated least square mean difference was 16.34%.

TABLE 5

Lipid Layer Thickness (LLT) measurements, based on relative changes compared to baseline pre-dose measurements determined in the morning before first dosing of the study, of F6H8 or Hydrabak. A pronounced early onset of action was observed when comparing the LLT at 2 weeks in comparison to Hydrabak.

Lipid Layer Thickness
measured in the morning before first daily dosing
(relative change from baseline in %)

| 2 weeks | | 4 weeks | |
|---|---|---|---|
| NovaTears | Hydrabak | NovaTears | Hydrabak |
| 6.83% | −9.08% | 4.10% | −7.50% |

Other signs endpoints (fluorescein corneal staining, TFBUT) as well as symptom endpoints (OSDI, VAS) improved in both treatment groups compared to baseline. The Hydrabak effect in the control arm though is also of a similar magnitude as the F6H8 effect at Visit 3 for most parameters. Corneal Staining tended to be stronger reduced in the F6H8 group. Compared to the Hydrabak group the F6H8 group reveals a more sustainable, improved effect over the entire 4 weeks course of the study.

Overall it can be concluded that the study meets its primary objective by demonstrating that F6H8 increases tear film thickness and the lipid layer thickness. This effect builds up over time and reaches its apparent maximum at the end of the 4 weeks study, which is in line with the mode of action of F6H8 preventing evaporation by supplementing and strengthening the lipid layer. Consistently, the observed increase of LLT in the F6H8 group further substantiates the overall observed improvement of the tear film. F6H8 appears to be safe and well tolerated in patients with DED, as all recorded adverse effects/adverse device effects were mild and occurred with low incidence.

Example 3

A Phase 2, Multi-Center, Randomized, Double-Masked, Saline-Controlled Study to Evaluate the Effect of 1-Perfluorohexyloctane (NOV03; F6H8) at two different dosing regimens on signs and symptoms of Dry Eye Disease (DED). The study was performed at 11 investigational cites in the United States. The study was reviewed and approved by the respective ethics committees and registered at www.clinicaltrials.gov (NCT03333057).

The study is performed to evaluate the safety, efficacy and tolerability of F6H8 at two different dosing regimens compared to saline on signs and symptoms of Dry Eye Disease.

Study subjects receive one of the following treatments over a period of 4 visits on day 1, 15, 30 and 60:

(1) F6H8 (NOV03), 4 times daily (QID);

(2) F6H8 (NOV03), 2 times daily (BID);

(3) Saline solution (0.9% sodium chloride solution), 4 times daily (QID);

(4) Saline Solution (0.9% sodium chloride solution), 2 times daily (BID).

In the BID treatment, study subjects instil bilaterally one drop in each lower eyelid conjunctival fornix two times daily. The instilled drop volume of F6H8 is about 10-12 µl, translating to a single dose of 13.5-16.2 mg (with F6H8 density=1.35 g/ml). At each visit, a broad range of DED relevant clinical measures were assessed, including adverse event query, visual acuity, Meibomian gland assessment, Ocular Surface Disease Index (OSDI), visual analog scale (VAS) for severity of dryness (burning/stinging, sticky feeling, foreign body sensation, itching, blurred vision, sensitivity to light, and pain and frequency for dryness), Tear Film Break-up Time (TFBUT), Fluorescein staining cornea NEI central region, Fluorescein staining cornea NEI inferior region, Lissamine green staining cornea and conjunctiva Oxford, Schirmer's Test I.

It was shown that BID treatment with F6H8—relating to administration of a daily dose of 20-24 µl (BID) of F6H8—resulted in an improvement of signs and/or symptoms of Dry Eye Disease. Furthermore, the 2-times daily schedule (BID) showed a trend towards less adverse effects.

The subject inclusion and exclusion criteria for the 2-times daily treatment was as follows:

Inclusion Criteria:

Subjects must:

Be at least 18 years of age.

Provide written informed consent.

Have a subject reported history of Dry Eye Disease in both eyes for at least 6 months prior to Visit 0.

Have Tear film break-up time (TFBUT)≤5 sec at Visit 0 and Visit 1.

Have total Ocular Surface Disease Index (OSDI)≥25 at Visit 0 and Visit 1.

Have a Schirmer's Test I≥5 mm at Visit 0 and Visit 1.

Have Meibomian Gland Dysfunction (MGD) defined as MGD score≥3 (secretion of 5 central glands on lower eyelid will be evaluated, each will be scored from 0-3; 0=normal, 1=thick/yellow, whitish, particulate 2=paste; 3=none/occluded; total score will range from 0-15) at Visit 0 and Visit 1.

Have a total corneal fluorescein staining score of 4≤X≤11 (i.e. sum of inferior, superior, central, nasal, and temporal) according to the National Eye Institute (NEI) grading at Visit 0 and Visit 1.

Have at least one eye (the same eye) satisfy all criteria for d, f, g, and h above at Visit 0 and Visit 1.

Be able and willing to follow instructions, including participation in all study assessments and visits.

Exclusion Criteria: (Excerpt)

Women who are pregnant, nursing or planning pregnancy

Unwillingness to submit a blood pregnancy test at screening and the last visit (or early termination visit) if of childbearing potential, or unwillingness to use acceptable means of birth control Clinically significant slit-lamp findings or abnormal lid anatomy at screening Ocular/peri-ocular malignancy History of herpetic keratitis Active ocular allergies or ocular allergies that are expected to be active during the study Ongoing ocular or systemic infection Wear contact lenses within 1 month prior to screening or anticipated use of contact lenses during the study Intra-ocular surgery or ocular laser surgery within the previous 6 months, or have planned ocular and/or lid surgeries over the study period Presence of uncontrolled systemic diseases Presence of known allergy and/or sensitivity to the study drug or saline components Use of any topical steroids treatments, topical cyclosporine, lifitegrast, serum tears or topical anti-glaucoma medication within 2 months prior to screening Subjects eligible to be randomized, received one of the following treatments to be administered bilaterally from Visit 1 to Visit 4:

After being trained on how to use the treatments, patients were advised to apply 1 drop of the respective treatment in each of both eyes.

| | |
|---|---|
| Treatment 1: NOV03 (ophthalmic composition essentially consisting of 1-perfluorohexyl-octane); VERUM | 4 times daily (QID) |
| Treatment 2: NOV03 (ophthalmic composition essentially consisting of 1-perfluorohexyl-octane); VERUM | 2 times daily (BID) |
| Treatment 3: Saline solution (0.9% sodium chloride solution); PLACEBO | 4 times daily (QID) |
| Treatment 4: Saline solution (0.9% sodium chloride solution); PLACEBO | 2 times daily (BID) |

The drop volume of a single drop of NOV03 (ophthalmic composition essentially consisting of 1-perfluorohexyl-octane; d=1.35 g/ml) relates to 10-12 μl, translating to 13.5-16.2 mg for a single dose per eye of or to a daily dose of 27-32.4 mg (20-24 μl) per eye for a 2-times daily treatment (BID).

The drop volume of a single drop of the Saline solution (0.9% sodium chloride solution) relates to 35-40 μl, translating to a daily dose of 70-80 μl per eye for a 2-times daily treatment (BID).

In the following, the NOV03 (ophthalmic composition essentially consisting of 1-perfluorohexyl-octane) treatment is also referred to a "Verum", while the Saline (0.9% sodium chloride solution) treatment is also referred to as "Placebo".

Visit Schedule:

This study consisted of two periods: a 14-day screening period and a 57-day treatment period.

Screening (Visit 0); Within 14 days before Visit 1 Subjects were required to sign an Informed Consent before completing any study related procedure. At the screening visit, vital signs will be assessed and the subject will give blood for safety laboratory tests. They were also submitted to a battery of tests to confirm the extent and severity of their symptoms and objective signs of dry eye. At least one eye must qualify with the following objective measures: Tear film break up time ≤5 sec, Schirmer's Test ≥5 mm, and Meibomian gland dysfunction (MGD) defined as MGD score ≥3 inclusive.

Baseline Visit Day 1 (Visit 1): On Day 1 (Visit 1), eligible subjects were evaluated for baseline signs and symptoms of dry eye disease. After randomization subjects at selected sites gave a blood sample to be used for PK. Subjects were given a 14-day supply and self-administered a single drop of the study medication into each eye at the clinic. Each subject was given a diary to record that their doses were taken. Study staff helped the subject to understand how to use the diary and when the remaining doses should be taken.

Visits 2-4; Subjects returned to the clinic on Day 15±1 (Visit 2), 29±2 (Visit 3), and 57±2 (Visit 4) to be evaluated for signs and symptoms of dry eye disease. During this period, subjects dosed NOV03 or the saline solution BID. The unused portion of the study medication was returned to the clinic and a new study medication kit as dispensed. The diary was checked. At Visit 4, vital signs were evaluated and a second blood draw was performed for PK at selected sites. The diary was collected at the clinic during each visit. Subjects were dismissed from the study after all Visit 4 assessments have been completed.

Patients and Examination Parameters 336 patients meeting the inclusion/exclusion criteria were selected by the investigational sites. The study population represented a highly symptomatic dry eye disease (DED) population with significant MGD involvement; this is evidenced for patients in the BID arm at baseline by a low TFBUT (mean TFBUT ~2.9), high total OSDI score (mean total OSDI ~56), high VAS severity of dryness score (mean VAS severity of dryness score ~70) and high MGD Score (mean MGD score ~7.3).

Parameters assessed both at the baseline visit and the following visit included OSDI Questionnaire, 10-item Visual Analog Scale (VAS) Questionnaire, Visual Acuity (ETDRS), Slit-lamp Biomicroscopy, TFBUT, Fluorescein Staining NEI grading, Lissamine Green Staining Oxford scale, Meibomian Gland Assessment (MGD score), Schirmer's Test I (without anesthesia).

323 patients completed the study, thereof 110 (NOV03, QID), 105 (NOV03, BID), 108 (Saline, BID+QID). Statistical analysis of the examination parameters was conducted to identify statistically significant differences between the verum and the placebo arms. Since there was no statistical difference between the Saline BID and Saline QID groups, for certain comparisons these groups were combined.

The parameters assessed in the study were performed according to the following protocols:

(a) Corneal Fluorescein Staining

5 μL of 2% preservative-free sodium fluorescein solution were instilled into the inferior conjunctival cul-de-sac of each eye (a fluorescein strip might be used but only at Visit 0) In order to achieve maximum fluorescence, the evaluation of the fluorescein staining after approximately 2-3 minutes waiting after instillation. A Wratten #12 yellow filter was be used to enhance the ability to grade fluorescein staining. The staining was graded with the NEI (National Eye Institute) Grading Scale. (ref., for example, Sook Chun Y et al., Am J Ophthalmol.2014 May; 157(5):1097 the-1102). Only the staining of the cornea was graded, not taking any staining of the conjunctiva into account. Digital images of fluorescein staining were taken for digital analysis.

Based on the NEI/Industry Workshop Scale grade the ocular surface damage for each eye is scored for each of the five regions of the cornea: central, superior, temporal, nasal and inferior. According to the NEI Grading Scale a standardized grading system of 0-3 is used to define the surface damage for each of the five regions on each cornea (central, superior, temporal, nasal, inferior). Total corneal staining for each eye is defined by the sum of scores for each of the five regions i.e. the sum of scores of central, superior, temporal, nasal and inferior). Grade 0 will be specified when no fluorescein staining is present. The maximum total score for each eye is 15.

(b) Ocular Surface and Disease Index (OSDI)© Questionnaire

The subjects were asked to fill out an OSDI© questionnaire (see for example, Schiffman R M, et al., Arch Ophthalmol. 2000; 118:615-621) consisting of 12 questions, and asked to respond on a scale of 0 to 4, with 0 corresponding to 'none of the time' and 4 corresponding to "all of the time". The questions assess dry eye symptoms experienced by the patient within past week in terms of the following ocular symptoms: sensitivity to light, gritty sensation, pain or sore eyes, blurriness, and poor vision; vision-related function, in terms of problems in: reading, driving at night, working on a computer or bank machine, watching television; and environmental factors or triggers i.e. discomfort during: windy conditions, places with low humidity, and areas with air condition. Subtotals are obtained for all the questions, as well as the number of questions answered. The OSDI index is assessed based on a scale of 0 to 100, with higher scores representing greater disability. It is calculated from the sum of scores multiplied by a factor of 25, over the total number of questions answered.

Typically, a sum of 0-12 usually represents normal (e.g. no dry eye disease), 13 to 22 represents mild dry eye disease, 23 to 32 represents moderate dry eye disease and greater than 33 represents severe dry eye disease. Thus, according to a mean OSDI score of 56 (total OSDI score range: 36 to 74), the patients treated in the study 2-times daily with NOV03 (BID) represent a severe dry eye disease population.

(c) Visual Analog Scale (VAS); Eye Dryness Score

Subjects were asked to rate their ocular symptoms (both eyes simultaneously) due to ocular dryness in a 10-item questionnaire and asked to place a vertical mark with horizontal line starting at the value of 0% and ending at a value of 100%, to indicate the level of discomfort (for example, for the symptom of dryness, a mark at 0 would correspond to "no dryness" and 100% corresponds to "maximal dryness"). Subjects were asked about the severity of the following symptoms of dryness, i.e. dry eye symptoms: severity of dryness, sticky feeling, burning/stinging, foreign body sensation, itching, blurred vision, sensitivity to light, and pain. Subjects will also be asked about their b) awareness of their dry eye symptoms and c) frequency of dryness. For these questions, the value of 0% corresponds to 'never' and a value of 100% corresponds to "all of the time". The assessment line length of the scale is 100 mm (10 cm).

A comparison is made between the values indicated by the patient at each visit, compared to baseline values at Day 1 visit.

According to a mean VAS severity of dryness score of 70 (VAS severity of dryness range 36-74) at baseline, the patients treated in the study 2-times daily with NOV03 (BID) represent a high symptomatic dry eye disease population.

(d) Tear Film Break-Up Time (TFBUT)

5 μL of 2% preservative-free sodium fluorescein solution was instilled into the inferior conjunctival cul-de-sac of each eye (a fluorescein strip might be used but only at Visit 0). To thoroughly mix the fluorescein with the tear film, the subject was instructed to blink several times. In order to achieve maximum fluorescence, approximately 30 seconds of waiting time after instillation elapsed before TFBUT was evaluated.

With the aid of a slit-lamp, the integrity of the tear film was monitored, noting the time it takes to form micelles from the time that the eye is opened. TFBUT was measured in seconds using a stopwatch and a digital image recording system for the right eye followed by the left eye. A Wratten #12 yellow filter was used to enhance the ability to grade TFBUT.

For each eye, two measurements were taken and averaged unless the two measurements are >2 seconds apart and are each <10 seconds, in which case, a third measurement was taken and the two closest of the three were averaged. All values were recorded in the source document.

According to a mean TFBUT of 2.9 seconds (TFBUT range 2-3.8 seconds) at baseline, the patients treated in the study 2-times daily with NOV03 (BID) represent a dry eye disease population, suffering from evaporative dry eye disease, with significant MGD-involvement and strong tear instability.

(e) Meibomian Gland Assessment (MGD Score)

Meibomian gland dysfunction (MGD) is blockage or some other abnormality of the meibomian glands whereby not enough oil or meibum is secreted into the tears. Because the tears then evaporate too quickly, MGD may be a leading cause of dry eye syndrome.

For analysis of the meibum, a Meibomian Gland Evaluator stick (Korb MGE®-Stick; Tear Science, Morrisville, US) was utilized, allowing for a reproducible and a standardized force application (1.25 g/mm2). The MGE-stick was used according to the instructions of the manufacturer.

The assessment was performed as follows: the secretion (meibum) of 5 central Meibomian glands on the lower eyelid was obtained by expressing the glands by standardized force of 1.25 g/mm2 utilizing the MGE-stick and evaluated. The expressed secretion (Meibum) was assessed and scored on a scale from 0 to 3, with 0=normal, 1=thick/yellow, whitish, particulate; 2=paste; 3=none/occluded. Therefore, the MGD-score represents the sum of the scores of the 5 central Meibomian Glands, thus the total score will range from 0-15.

Herein, a MGD score of equal or higher than 6 relates to at least 3 out of 5 central meibomian glands presenting as pasty (thick) matter, or 2 out of 5 central meibomian glands being occluded upon expressing the meibum from said glands by a standardized force of about 1.0-2.0 g/mm2, preferably by a standardized force of about 1.25 g/mm2.

Further, a MGD score of equal or higher than 7 relates to at least 2 out of 5 central meibomian glands presenting as pasty (thick) matter and at least 1 out of 5 central meibomian glands presenting as being occluded upon expressing the meibum from said glands by a standardized force of about 1.0-2.0 g/mm2, preferably by a standardized force of about 1.25 g/mm2.

According to a mean MGD score of 7.3 (MGD score range 3.6-11) at baseline, the patients treated in the study 2-times daily with NOV03 (BID) represent a dry eye disease population, suffering from evaporative dry eye disease, with significant MGD-involvement (abnormal meibum and/or occluded Meibomian glands).

(f) Schirmer's Test I (Without Anesthesia)

Schirmer Tear Test I will be performed according to the following procedure:

Do not blot prior to the test

Using a sterile Schirmer test strip, a bend in the strip will be made in line with the notch in the strip The subject will be instructed to gaze up and in The Schirmer test strip will be placed in the lower temporal lid margin of each eye such that the strip fits tightly. Subjects will be instructed to close their eyes After 5 minutes have elapsed, the Schirmer strip will be removed. The length of the moistened area will be recorded (mm) for each eye Results BID Treatment The examination parameters were compared between 2 times daily treatment (BID) of NOV03 (ophthalmic composition essentially consisting of 1-perfluorohexyl-octane; *Verum*) with Placebo (Saline solution; 0.9% sodium chloride solution; BID).

The study demonstrated relevant and statistically significant improvements in both signs (i.e. reduction of ocular surface damage of corneal region) and symptoms of dryness in a highly symptomatic dry eye disease (DED) population with significant MGD involvement when treated 2 times daily by a single drop of 10-12 µl of an ophthalmic composition essentially consisting of 1-perfluorohexyl-octane to the eye of patient.

The study met its prespecified primary efficacy endpoint of total corneal fluorescein staining demonstrating the reduction of the ocular surface damage of the total corneal region at 8 weeks for the BID dosing regimen.

Additionally, clear improvements were observed for the reduction of the ocular surface damage also for the central corneal region, the nasal corneal region and the temporal corneal region as evidenced by corresponding fluorescein staining and subsequent grading of the central, nasal, temporal, inferior corneal region according to the NEI scale. Notably, the reduction of the ocular surface damage of the central cornea region is highly important, as the central corneal region is in the center of the visual axis and thus improvement in this ocular surface damage parameter is directly linked to an improvement of the visual acuity of the patient. Further, reduction of ocular surface damage of the superior and the inferior corneal region did not show such clear improvement in respect to ocular surface damage [See FIGS. 1(a) to (d)].

The treatment effect relating to the signs, such as reduction of ocular surface damage, started surprisingly early (2 weeks) and was significant throughout the visit (at 4 weeks, 8 weeks).

Furthermore, the study showed highly statistical significant improvement in various symptoms of dryness over the placebo group, determined by the Eye Dryness Score on a visual analog scale (VAS), including "severity of dryness", "frequency of dryness", "awareness of dryness", "blurred vision", "sensitivity to light". The other VAS symptoms did not improve clearly [see FIGS. 2(a)-(e)].

Also here, treatment effect relating to the VAS symptoms of dryness started surprisingly early (2 weeks) and was significant throughout the visit (at 4 weeks, 8 weeks).

Figure 3:
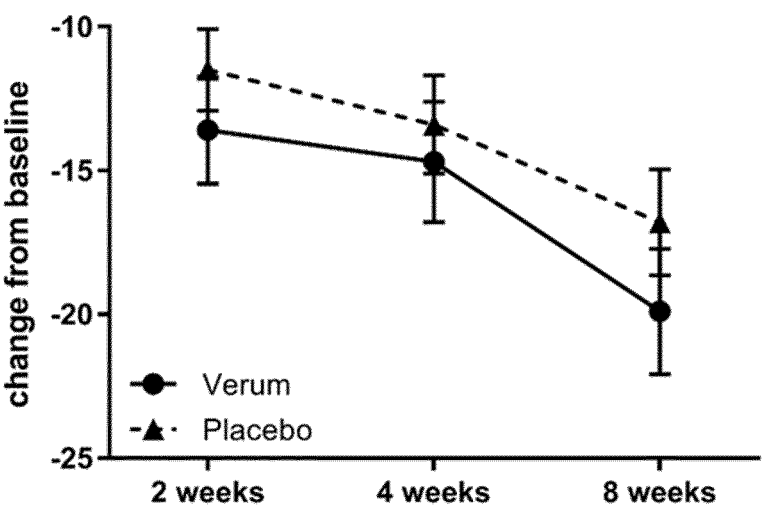
FIG. 3. Total Ocular Surface Disease Index (OSDI)—Depicted is the change from baseline (Visit 1, Day 1) of total OSDI score for Visit 2 (2 weeks), Visit 3 (4 weeks) and Visit 4 (8 weeks), with *Verum* representing the 2-times daily treatment (BID) with NOV03 (ophthalmic composition essentially consisting of 1-perfluorohexyloctane; solid line) and placebo representing the Saline solution (0.9% sodium chloride solution; QID+BID; dotted line). Improvement of the symptoms of dryness determined by the ocular surface disease index (OSDI) score (see experimental section for details on the OSDI questionnaire).

Further, the study showed highly statistical significant improvement in various symptoms of dryness over the placebo group, determined by ocular surface disease index (OSDI) score, including total OSDI score [see FIG. 3].

Also here, the treatment effect relating to the OSDI symptoms of dryness started surprisingly early (2 weeks) and was significant throughout the visit (at 4 weeks, 8 weeks).

Figure 4:
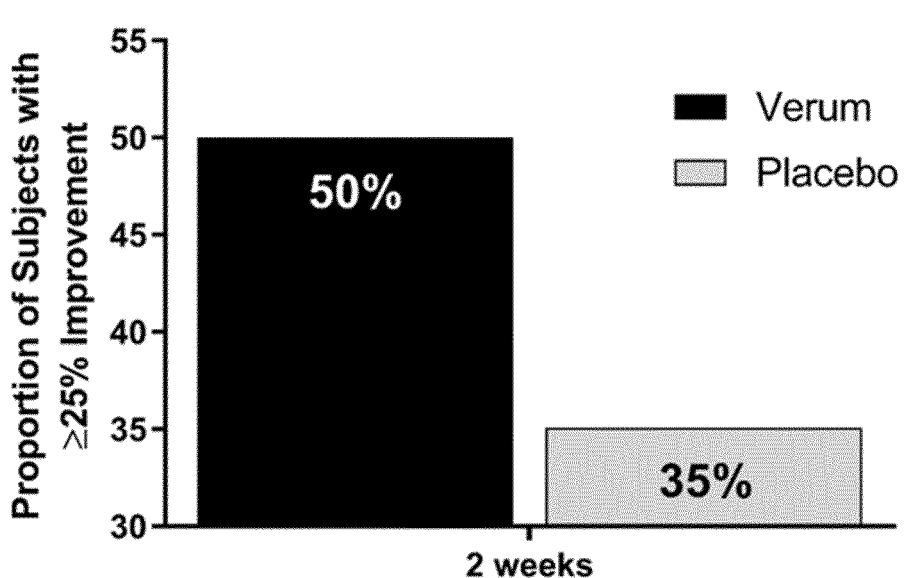
FIG. 4. Response assessment of NOV03-treatment (BID), based on severity of dryness assessment using Eye Dryness Score on an Visual Analog Scale (VAS); depicted is a graph charting the response of the patients in respect to the dryness symptom "severity of dryness" shortly after start of the therapy in subjects treated with NOV03 (ophthalmic composition essentially consisting of 1-perfluorohexyloctane; *verum*; solid line) in comparison to patients treated with Saline ((0.9% sodium chloride solution; QID+BID; placebo; dotted line).

Further, it was found that the response rate to the 2 times daily treatment (BID) with NOV03 was surprisingly high, even at an early point in time after first administration to the patient. When defining the response as a reducing the VAS severity of dryness score by ≥25%, already about 50% of the patient responded positively to the treatment already after 2 weeks (see FIG. 4). Thus, the 2 times daily treatment (BID) with NOV03 results in a quick reduction of symptoms of dryness at a comparable low daily dose of 27-32.4 mg (20-24 µl) of a composition essentially consisting of 1-perfluorohexyl-octane per eye.

The invention claimed is:

1. A method of providing delayed ophthalmic release of a semifluorinated alkane, wherein the method comprises the steps of (a) administering to the eye of a patient in need thereof an amount of an ophthalmic composition consisting of a mixture of $F(CF_2)_6(CH_2)_8H$ and 2-perfluorohexyloctane, wherein the amount is effective to enrich an ophthalmic tissue in $F(CF_2)_6(CH_2)_8H$, and (b) delayed release of $F(CF_2)_6(CH_2)_8H$ from the enriched ophthalmic tissue;

wherein the ophthalmic composition is administered to the surface of the cornea and/or the conjunctiva in the form of liquid drops;

wherein the patient suffers from keratoconjunctivitis sicca (dry eye disease); and wherein the patient is non-responsive to physical methods of treating Meibomian Gland Dysfunction.

2. A method of treating keratoconjunctivitis sicca (dry eye disease) due to Meibomian gland dysfunction, wherein the method comprises the steps of (a) administering to the eye of a patient in need thereof an amount of an ophthalmic composition consisting of a mixture of $F(CF_2)_6(CH_2)_8H$ and 2-perfluorohexyloctane, wherein the amount is effective to enrich an ophthalmic tissue in $F(CF_2)_6(CH_2)_8H$, and optionally (b) delayed release of $F(CF_2)_6(CH_2)_8H$ from the enriched ophthalmic tissue;

wherein the ophthalmic composition is administered to the surface of the cornea and/or the conjunctiva in the form of liquid drops;

wherein the patient suffers from keratoconjunctivitis sicca (dry eye disease); and wherein the patient is non-responsive to physical methods of treating Meibomian Gland Dysfunction.

3. The method according to claim 2, wherein the composition consists of $F(CF_2)_6(CH_2)_8H$ and up to 3 wt % of 2-perfluorohexyloctane, based on the total weight of the composition.

4. The method according to claim 2, wherein the physical methods of treating Meibomian Gland Dysfunction are selected from heat compresses, eye lid massaging, and forced expression of the Meibomian glands.

5. The method according to claim 2, wherein the composition is administered in a dose of a single drop per eye less than four times per day.

6. The method according to claim 2, wherein the composition is administered in a dose of a single drop of 10-12 µl per eye two times per day.

7. The method of claim 2, wherein the patient is characterized by at least 2 of the criteria selected from the group consisting of:

(i) a total ocular surface disease index (OSDI) of higher than 25;

(ii) a total corneal fluorescein staining (NEI scale) between 4 and 11;

(iii) a Schirmer's Test I greater than 5 mm; and (iv) an MGD score of higher than 3.

8. The method according to claim 2, wherein the composition consists of $F(CF_2)_6(CH_2)_8H$ and up to 1 wt % of 2-perfluorohexyloctane, based on the total weight of the composition.

9. A method of treating keratoconjunctivitis sicca (dry eye disease), wherein the method comprises the steps of (a) administering to the eye of a patient in need thereof an amount of an ophthalmic composition consisting of a mixture of $F(CF_2)_6(CH_2)_8H$ and 2-perfluorohexyloctane, wherein the amount is effective to enrich an ophthalmic tissue in $F(CF_2)_6(CH_2)_8H$, and optionally (b) delayed release of $F(CF_2)_6(CH_2)_8H$ from the enriched ophthalmic tissue;

wherein the ophthalmic composition is administered to the surface of the cornea and/or the conjunctiva in the form of liquid drops;

wherein the patient suffers from keratoconjunctivitis sicca (dry eye disease); and wherein the patient is non-responsive to physical methods of treating Meibomian Gland Dysfunction.

10. The method according to claim 9, wherein the composition consists of $F(CF_2)_6(CH_2)_8H$ and up to 3 wt % of 2-perfluorohexyloctane, based on the total weight of the composition.

11. The method according to claim 9, wherein the physical methods of treating Meibomian Gland Dysfunction are selected from heat compresses, eye lid massaging, and forced expression of the Meibomian glands.

12. The method according to claim 9, wherein the composition is administered in a dose of a single drop per eye less than four times per day.

13. The method according to claim 9, wherein the composition is administered in a dose of a single drop of 10-12 µl per eye two times per day.

14. The method of claim 9, wherein the patient is characterized by at least 2 of the criteria selected from the group consisting of:

(i) a total ocular surface disease index (OSDI) of higher than 25;

(ii) a total corneal fluorescein staining (NEI scale) between 4 and 11;

(iii) a Schirmer's Test I greater than 5 mm; and (iv) an MGD score of higher than 3.

15. The method according to claim 9, wherein the composition consists of $F(CF_2)_6(CH_2)_8H$ and up to 1 wt % of 2-perfluorohexyloctane, based on the total weight of the composition.

16. The method according to claim 1, wherein the composition consists of $F(CF_2)_6(CH_2)_8H$ and up to 1 wt % of 2-perfluorohexyloctane, based on the total weight of the composition.

17. The method according to claim 1, wherein the composition consists of $F(CF_2)_6(CH_2)_8H$ and up to 3 wt % of 2-perfluorohexyloctane, based on the total weight of the composition.

18. The method according to claim 1, wherein the physical methods of treating Meibomian Gland Dysfunction are selected from heat compresses, eye lid massaging, and forced expression of the Meibomian glands.

19. The method according to claim 1, wherein the composition is administered in a dose of a single drop per eye less than four times per day.

20. The method according to claim 1, wherein the composition is administered in a dose of a single drop of 10-12 µl per eye two times per day.

21. The method of claim 1, wherein the patient is characterized by at least 2 of the criteria selected from the group consisting of:

(i) a total ocular surface disease index (OSDI) of higher than 25;

(ii) a total corneal fluorescein staining (NEI scale) between 4 and 11;

(iii) a Schirmer's Test I greater than 5 mm; and (iv) an MGD score of higher than 3.

* * * * *